(12) United States Patent
Yu et al.

(10) Patent No.: US 11,033,507 B2
(45) Date of Patent: Jun. 15, 2021

(54) METHOD OF SYNTHESIS OF SILICA VESICLES AND USE THEREOF

(71) Applicant: THE UNIVERSITY OF QUEENSLAND, Brisbane (AU)

(72) Inventors: Chengzhong Yu, Brisbane (AU); Neena Mitter, Brisbane (AU); Jun Zhang, Brisbane (AU)

(73) Assignee: The University of Queensland, Brisbane (AU)

( * ) Notice: Subject to any disclaimer, the term of this patent is extended or adjusted under 35 U.S.C. 154(b) by 371 days.

(21) Appl. No.: 15/106,825

(22) PCT Filed: Dec. 19, 2014

(86) PCT No.: PCT/AU2014/050439
§ 371 (c)(1),
(2) Date: Jun. 20, 2016

(87) PCT Pub. No.: WO2015/089590
PCT Pub. Date: Jun. 25, 2015

(65) Prior Publication Data
US 2018/0193278 A1    Jul. 12, 2018

(30) Foreign Application Priority Data
Dec. 19, 2013 (AU) ................. 2013904973

(51) Int. Cl.
*A61K 9/50* (2006.01)
*A61K 39/12* (2006.01)
(Continued)

(52) U.S. Cl.
CPC ............ *A61K 9/501* (2013.01); *A61K 9/5031* (2013.01); *A61K 9/5115* (2013.01);
(Continued)

(58) Field of Classification Search
CPC .......... A61K 2039/55505; A61K 39/12; A61K 39/39; A61K 9/501; A61K 9/5031;
(Continued)

(56) References Cited

U.S. PATENT DOCUMENTS 6,592,764 B1    7/2003    Stucky et al.
7,176,245 B2    2/2007    Stucky et al.
(Continued)

FOREIGN PATENT DOCUMENTS

CN    1730392 A    2/2006
CN    101289189 A    10/2008
(Continued)

OTHER PUBLICATIONS

Kipkemboi et al., "Triblock Copolymers as Templates in Mesoporous Silica Formation: Structural Dependence on Polymer Chain Length and Synthesis Temperature," Langmuir 2001, 17, 5398-5402. (Year: 2001).*
(Continued)

*Primary Examiner* — Aradhana Sasan
(74) *Attorney, Agent, or Firm* — Nixon & Vanderhye P.C.

(57) ABSTRACT

The invention relates, in part, to a method of producing silica vesicles including under controlled conditions to thereby heavily influence the morphology and characteristics of the vesicles. The vesicles are shown to be effective as delivery agents for chemical and biological agents. They are also shown to be useful in methods of treatment and as components of an immunogenic composition.

9 Claims, 30 Drawing Sheets

(51) Int. Cl.
  *A61K 9/51* (2006.01)
  *A61K 39/39* (2006.01)
  *A61K 39/00* (2006.01)
  *C01B 33/18* (2006.01)
  *B82Y 40/00* (2011.01)
  *B82Y 30/00* (2011.01)
  *B01J 13/10* (2006.01)

(52) U.S. Cl.
  CPC ............ *A61K 9/5146* (2013.01); *A61K 39/12* (2013.01); *A61K 39/39* (2013.01); *B01J 13/10* (2013.01); *B82Y 30/00* (2013.01); *B82Y 40/00* (2013.01); *C01B 33/18* (2013.01); *A61K 2039/55505* (2013.01); *C01P 2004/34* (2013.01); *C01P 2004/64* (2013.01); *C01P 2006/16* (2013.01); *C12N 2770/24034* (2013.01)

(58) Field of Classification Search
  CPC ..... A61K 9/5115; A61K 9/5146; B01J 13/10; B82Y 30/00; B82Y 40/00; C01B 33/18; C01P 2004/34; C01P 2004/64; C01P 2006/16; C12N 2770/24034
  See application file for complete search history.

(56) References Cited

U.S. PATENT DOCUMENTS

| | | | |
|---|---|---|---|
| 7,763,665 | B2 | 7/2010 | Stucky et al. |
| 8,642,258 | B2 | 2/2014 | Pacheco et al. |
| 2003/0205528 | A1 | 11/2003 | Stucky et al. |
| 2004/0144726 | A1 | 7/2004 | Stucky et al. |
| 2007/0256978 | A1 | 11/2007 | Stucky et al. |
| 2010/0254890 | A1 | 10/2010 | Yang et al. |

FOREIGN PATENT DOCUMENTS

| | | |
|---|---|---|
| CN | 101348254 A | 1/2009 |
| CN | 101797387 A | 8/2010 |
| CN | 101837983 A | 9/2010 |
| CN | 102285659 A | 12/2011 |
| CN | 102476803 A | 5/2012 |
| CN | 103012594 A | 4/2013 |
| CN | 103433005 A | 12/2013 |
| JP | 2000012314 A | 1/2000 |
| JP | 2006327849 A | 12/2006 |
| JP | 2009507859 A | 2/2009 |
| JP | 2013237601 A | 11/2013 |
| KR | 10-20120021528 | 10/2013 |
| WO | 2007030901 A1 | 3/2007 |

OTHER PUBLICATIONS

International Search Report for PCT/AU2014/050439, seven pages (dated Mar. 2015).
Written Opinion of ISA for PCT/AU2014/050439, seven pages (dated Mar. 2015).
Zhao et al. "Nonionic Triblock and Star Diblock Copolymer and Oligomeric Surfactant Syntheses of Highly Ordered, Hyrdothermally Stable, Mesopourous Silica Structures" *Journal of the American Chemical Society*, vol. 120, No. 4, pp. 6024-6036 (1998).
Chinese Office Action with English Translation for CN Application No. 201480075307.6, dated Mar. 31, 2020.
Examination Report for India Application No. 201627023776 dated Nov. 14, 2019.
Yu, M. et al., "Preparation of Siliceous Vesicles with Adjustable Sizes, Wall Thickness and Shapes," Chem. Lett., Apr. 4, 2009, vol. 38, No. 5, pp. 442-443, with Supplementary Electronic Supporting Information.
Zhao, D., et al., "Triblock Copolymer Syntheses of Mesoporous Silica with Periodic 50 to 300 Angstrom Pores," Science (1998) 279:548-552.
Matos, J., et al., "Toward the Synthesis of Extra-Large Pore MCM-41 Analogues," Chem. Mater. (2001) 13:1726-1731.
Yu, M., et al., "Self-assembly and structure control of new silica vesicle materials [D]", Journal of Fudan University, 2008, considered only to the extent of the degree of relevance provided by Applicant.
Wang, H., "Preparation and characterization of new vesicles and foam materials [D]", Journal of Fudan University, 2009, considered only to the extent of the degree of relevance provided by Applicant.
Wang, H., et al., "Silceous Unilamellar Vesicles and Foams by Using Block-Copolymer Cooperative Vesicle Templating," Advanced Functional Materialsm vol. 17, No. 4, (2007), pp. 613-617.
Fangquiong, Tang F., et al, "Mesoporous Silica Nanoparticles: Synthesis, Biocompatibility and Drug Delivery," Advanced Materials, vol. 24, No. 12, (2012) pp. 1504-1534.
Nandiyanto ABD et al, "Synthesis of Spherical Mesoporous Silica Nanoparticles with Nanometer-size Controllable Pores and Outer Diameters," Microporous and Mesoporous Materials, vol. 120, No. 3, (2009), pp. 447-453.
Emma M Johansson: "Controlling the Pore Size and Morphology of Mesoporous Silica," Linkoping Studies in Science and Technology Licentiate Thesis No. 1451, Jan. 1, 2010.
Wu, D., et al, "Design and Prepareion of Porous Polymers," Chemical reviews, vol. 112, No. 7, (2012) pp. 3959-4015.
Chinese Office Action for CN Application No. 201480075307.6, dated Jun. 6, 2018.
Japanese Office Action for JP Application No. 2016-540997, dated Jan. 8, 2019.

* cited by examiner a) oE2 (100μg) + Quil A (10μg)
8 weeks after the second injection b) oE2 (100μg)/SV-140 (500μg)
8 weeks after the second injection c) oE2 (100μg) + Quil A (10μg)
12 weeks after the second injection d) oE2 (100μg)/SV-140 (500μg)
12 weeks after the second injection e) oE2 (100μg) + Quil A (10μg)
16 weeks after the second injection f) oE2 (100μg)/SV-140 (500μg)
16 weeks after the second injection g) oE2 (100μg) + Quil A (10μg)
20 weeks after the second injection h) oE2 (100μg)/SV-140 (500μg)
20 weeks after the second injection i) oE2 (100μg) + Quil A (10μg)
24 weeks after the second injection j) oE2 (100μg)/SV-140 (500μg)
24 weeks after the second injection

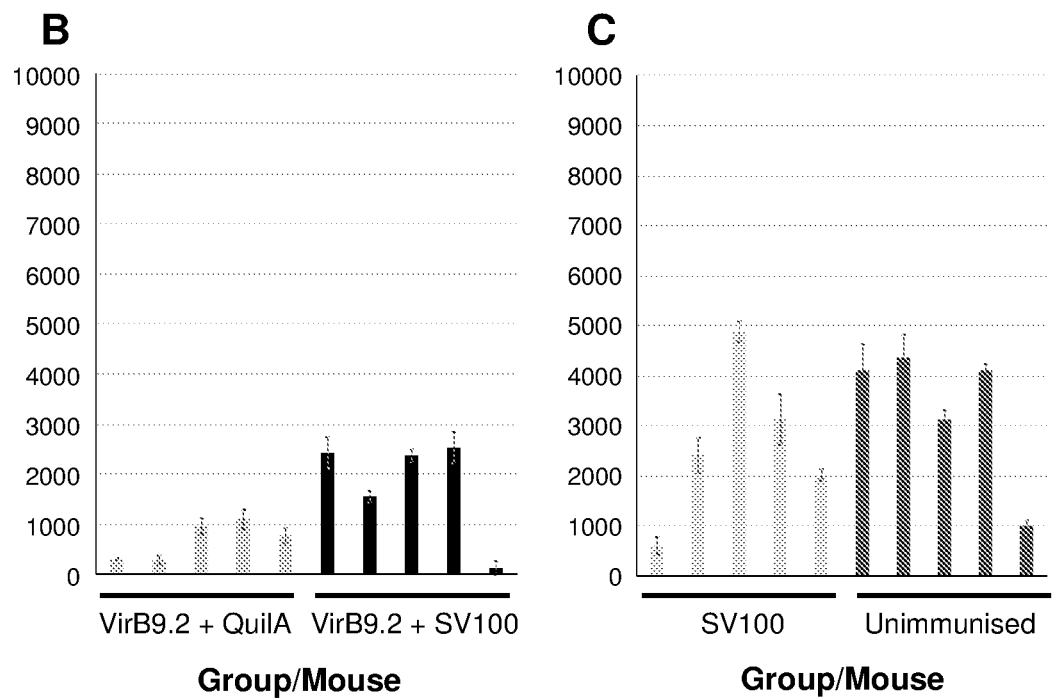
FIG 34 B-C
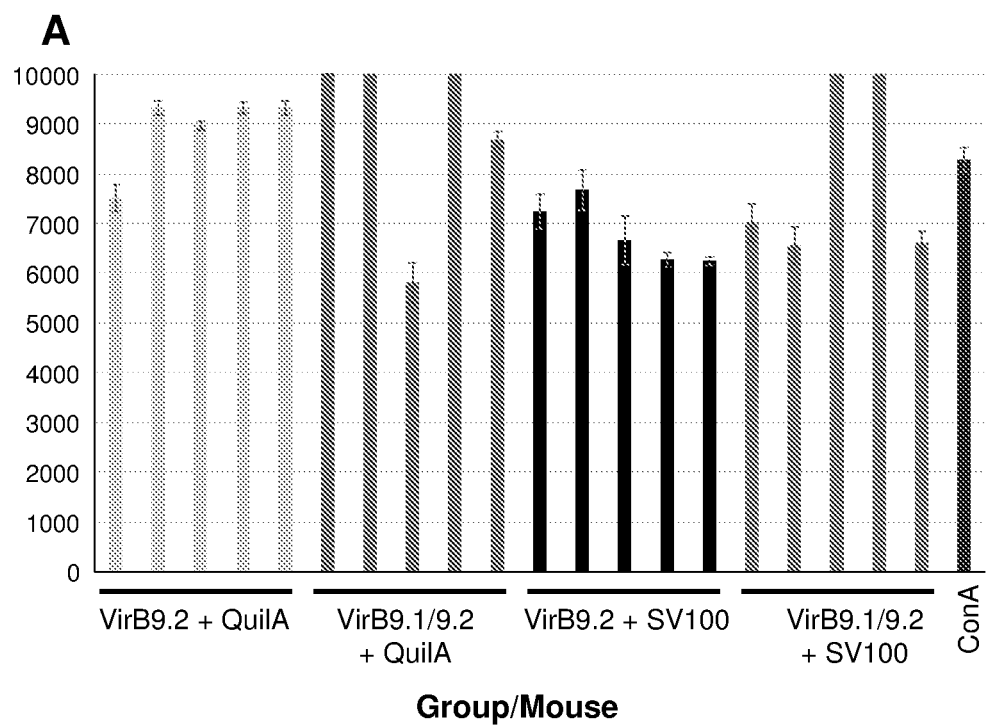
FIG 35 A

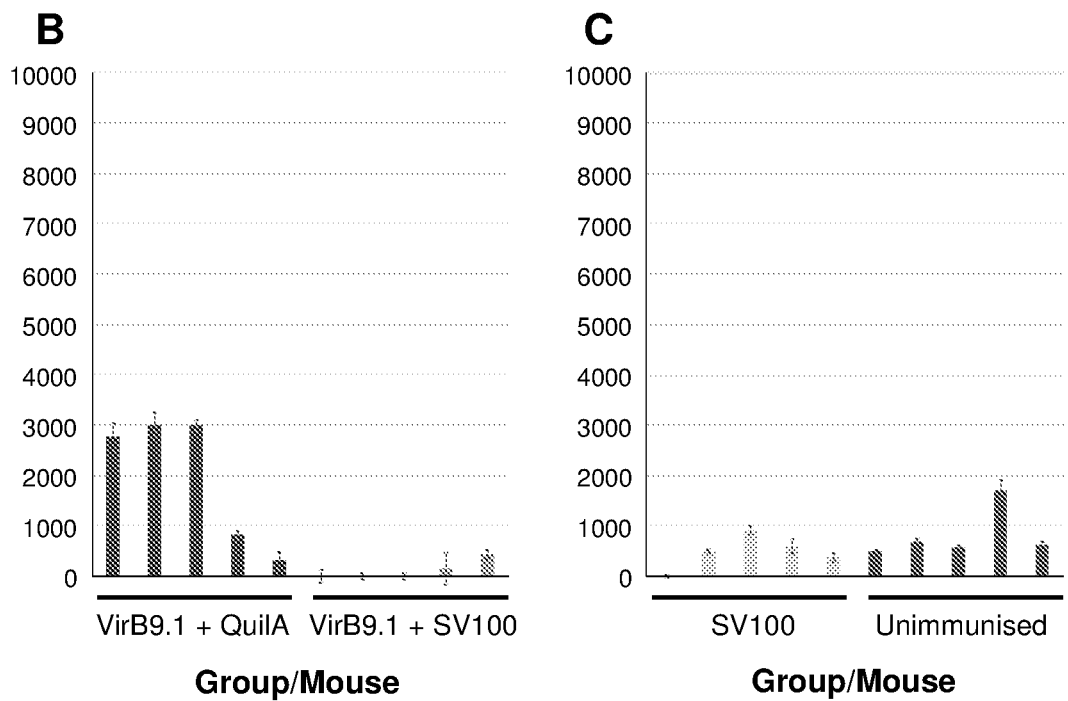
FIG 35 B-C
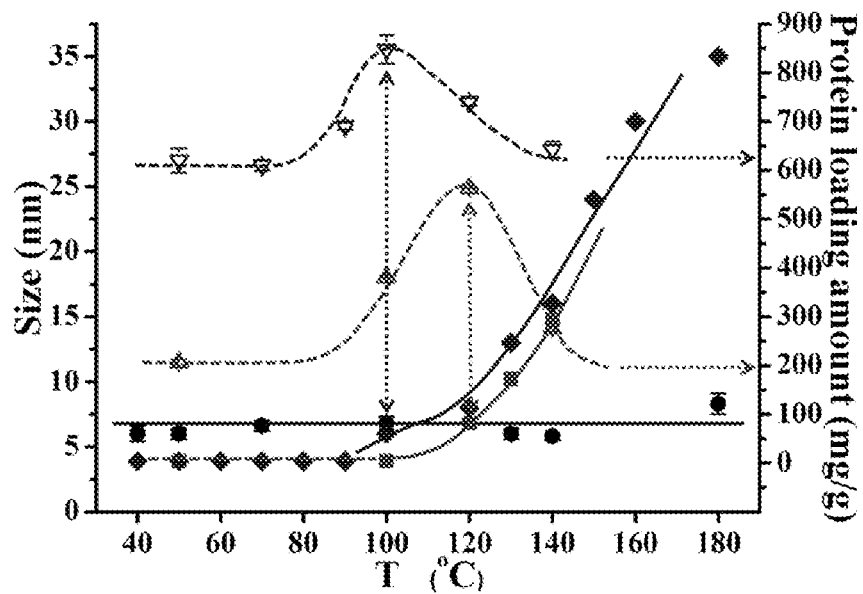
FIG 36

METHOD OF SYNTHESIS OF SILICA VESICLES AND USE THEREOF

CROSS REFERENCE TO RELATED APPLICATIONS

This application is the U.S. national phase of International Application No. PCT/AU2014/050439, filed 19 Dec. 2014, which designated the U.S. and claims priority to Australian Patent Application No. 2013904973, filed 19 Dec. 2013; the entire contents of each of which are hereby incorporated by reference.

FIELD OF THE INVENTION

The invention relates to the field of chemical synthesis. More particularly, this invention relates to a method of synthesising a hollow silica vesicle, the silica vesicle thereby produced and its use in drug delivery and as part of an immunogenic composition.

BACKGROUND TO THE INVENTION

Any reference to background art herein is not to be construed as an admission that such art constitutes common general knowledge in Australia or elsewhere.

Inorganic hollow spheres have attracted considerable attention due to their unique morphology and potential use in a wide range of applications. They show good stability in solvents and body fluids, have excellent thermal properties and also high mechanical strength by comparison with their organic counterparts. These properties have seen them used in applications as varied as catalysis, drug/gene delivery, bio-imaging, as nanoreactors, low-dielectric constant materials and in separation technologies.

Methods have been developed to synthesize inorganic hollow spheres utilizing preformed templates to produce the desired characteristics. Some techniques involve a soft template approach, including micelles, emulsions, microemulsions etc. This approach has a number of drawbacks including the need for a significant amount of chemical based organic solvents or organic additives. A hard template approach, including single crystals and colloid spheres, has also been utilized to produce spheres with the required pore size followed by an etching step to remove the hard template. Such an approach is expensive, time-intensive and environmentally-unfriendly and has been shown to give relatively low yields of product.

Silica vesicles are a type of hollow sphere constructed by supramolecular assembly in the absence of preformed templates. Silica vesicles with small particle sizes (generally smaller than 200 nm in diameter) have potential cell-based and/or animal applications due to their low toxicity and biodegradability. The void space inside the hollow morphology can be used as a reservoir for high-capacity storage of cargo molecules and subsequent controlled release. The wall structure (including wall thickness and porous nature) is crucial for both the immobilisation and release of cargo molecules. However, fine control over the pore size and entrance size within the walls of silica vesicles has proven to be a difficult challenge.

It would be useful to provide silica vesicles (SV) with controlled structures for the delivery of small molecules and larger biomolecules alike which overcomes or circumvents one or more of these problems.

SUMMARY OF INVENTION

According to a first aspect of the invention, there is provided a method of forming a silica vesicle including the steps of:
(a) producing a silica formulation by adding a hydrolysable silica source to an aqueous solution comprising a block copolymer, the silica formulation being maintained at a temperature of less than 20° C., and agitating the formulation until silica-polymer composite vesicles form, followed by step (b) or step (c);
(b) raising the temperature of the silica formulation containing the silica-polymer composite vesicles to be between 25° C. to 100° C. and agitating the mixture to form silica-polymer composite vesicles having spherical structures within the vesicle walls;
(c) exposing the vesicles to a hydrothermal treatment; and
(d) calcining the vesicles,
to thereby produce the silica vesicles.

According to a second aspect of the invention there is provided a silica vesicle having:
(a) a particle diameter of between 30 to 70 nm;
(b) a wall structure perforated by spherical pores; and
(c) an average pore entrance size of between 4 to 40 nm formed in the wall.

Preferably, the particle diameter is between 40 to 60 nm, more preferably about 45 to 55 nm, even more preferably about 50 nm.

A third aspect of the invention resides in a silica vesicle when produced by the method of the first aspect.

According to a fourth aspect of the invention there is provided a drug or chemical delivery system comprising a silica vesicle of the second or third aspects and a drug or chemical agent encapsulated within the vesicle or bound to an outer surface thereof.

Preferably, the drug is an organic drug molecule and the chemical agent is a pesticide.

A fifth aspect of the invention resides in an immunogenic composition comprising one or a plurality of silica vesicles of the second or third aspects and one or a plurality of immunogens and/or antigens.

Preferably, the immunogen is an immunogenic fragment of the bovine viral diarrhoea virus (BVDV). More preferably, the immunogen and/or antigen is the E2 protein, or a fragment thereof, of the BVDV.

A sixth aspect of the invention resides in a method of eliciting an immune response in a subject including the step of administering a therapeutically effective amount of the immunogenic composition of the fifth aspect A seventh aspect of the invention resides in a method of preventing or treating a disease or condition including the step of administering a therapeutically effective amount of the immunogenic composition of the fifth aspect to a subject in need thereof.

In one embodiment, the disease or condition is bovine viral diarrhoea.

An eighth aspect of the invention resides in the use of a silica vesicle of the second or third aspects and an immunogen in the manufacture of a medicament for the treatment of a disease or condition.

A ninth aspect of the invention resides in the use of a silica vesicle of the second or third aspects as an adjuvant.

The various features and embodiments of the present invention, referred to in individual aspects above apply, as appropriate, to other aspects, mutatis mutandis. Consequently features specified in one aspect may be combined with features specified in other aspects, as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein:

FIG. 24 is a graphical representation showing end point titer data of test sera bleeds for the four animals maintained for long-term antibody responses after the second immunisation. Sera of individual animals were diluted from 1:100 to 1:6400. The graph line in the chart represents the four individual animals (M5 to M8) in each group;

FIG. 35 is a graphical representation showing the cell mediated immune response against VirB9.2 protein. The antigen specific IFN-γ secretion by ELISPOT assay of murine splenocytes from 5 individual mice. (A) Mice injected with VirB9.2+Quil-A show comparable results to VirB9.2+SV100 and also to the multivalent injections VirB9.1/9.2+Quil-A and VirB9.1/9.2+SV100. ConA is the internal control. (B) There was minimal response of animals injected with VirB9.1+QuilA and VirB9.1+SV100 and (C) SV100 alone and unimmunised responses;

FIG. 36 is a graphical representation showing correlations of the wall thickness of calcined silica vesicles (circle), entrance size before (diamond) and after (square) hydrophobic modification, the cytochrome c adsorption capacity (upside down triangle) on unmodified silica vesicles and ribonuclease a (lower line, triangle) on modified silica vesicles, as a function of T. T is the temperature of the last synthetic step;

DETAILED DESCRIPTION

Figure 1:
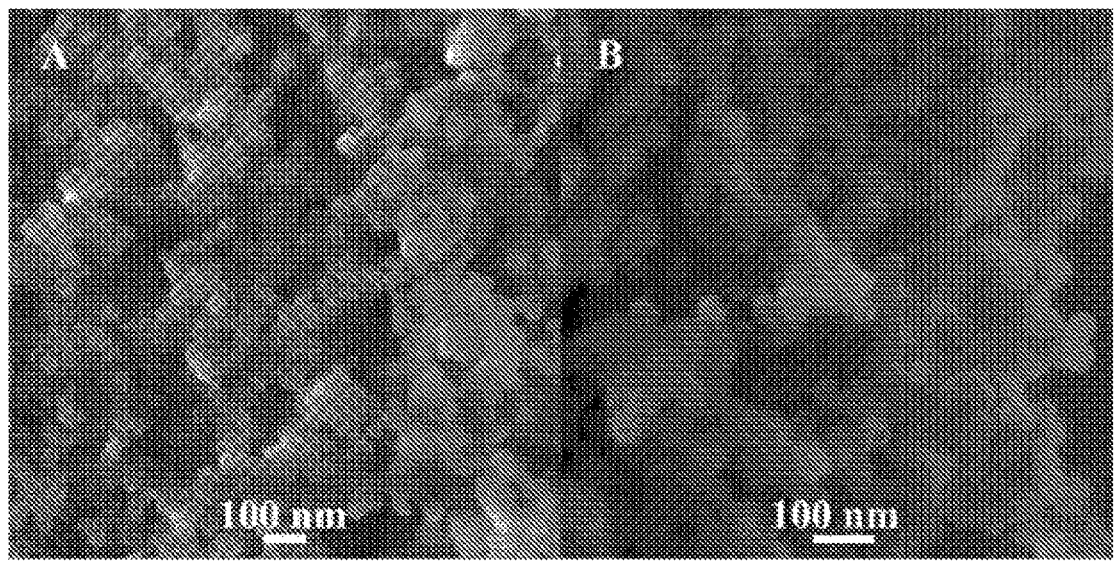
FIG. 1 is a series of FE-SEM images of novel silica vesicles (A) SV-10-50 and (B) SV-10-50-140 after calcinations.

The present invention is predicated, at least in part, on the finding that precise control over the formation of relatively large pore hollow silica vesicles with high purity (>98%) and yield, unique pore wall structure and controllable pore entrance size is achieved by an approach which includes; a first step of cooperative self-assembly at low temperature to form unilamellar vesicles of silica-polymer composites; a second step involving a secondary controlled self-assembly process within the composite walls at a moderate/intermediate temperature to form and shape pore wall structures; and an optional third step being a hydrothermal treatment process at high temperature which allows for further adjustment of the pore entrance sizes, when required. The novel silica vesicles provided have been found to have a number of desirable properties including high protein loading capacity, excellent cell uptake and efficacy as a drug/chemical agent delivery system and as part of an immunogenic composition for vaccine purposes.

In this patent specification, adjectives such as first and second, left and right, front and back, top and bottom, etc., are used solely to define one element or method step from another element or method step without necessarily requiring a specific relative position or sequence that is described by the adjectives unless such is clear from the context.

Unless defined otherwise, all technical and scientific terms used herein have the same meaning as would be commonly understood by those of ordinary skill in the art to which this invention belongs.

As used herein, the terms "silica vesicle" (SV) or "hollow silica vesicle" (HSV) refer generally to a vesicle comprising a silica based wall surrounding an internal cavity. Particularly, the SV's described herein have a cavity in the mesoporous range (i.e. between 2 to 50 nm) and have a unilamellar silica-void-silica wall and can be classified as small unilamellar vesicles (SUVs) as they have a diameter of less than 100 nm. Porosity in the walls of the vesicles is provided by spherical perforations in the vesicle walls. These spherical pores may be interconnected so as to form a continuous pore pathway bridging the inner and outer surfaces of the vesicle walls. In cases where the spherical pores have a diameter similar to the thickness of the wall of the vesicle, a single spherical pore can bridge the inner and outer surfaces of the wall, providing a large pore entrance to the internal cavity of the vesicle.

As used herein, the word "agitation" may refer to any means of causing mixing, perturbation or other dynamic movement of the reagents during the respective reaction.

Stirring is a preferred means of agitating the reaction mixture although, sonication, shaking and other means may be acceptable.

In the experimental work described herein the silica vesicles synthesised are generally denoted by the treatment temperature steps they have undergone during synthesis. For example, SV-T1-T2-T3-n, in which T1, T2 and T3 indicate the temperature for each of the three synthetic steps employed, respectively. The suffix n stands for the specific samples, for example, 'c' stands for after calcination, 'a' stands for amino-modification having been carried out on the sample and 'u' or 'l' inform as to whether the sample was taken from the upper or lower layer in those particular instances where the reaction mixture comprised more than one phase. The letter 'x' indicates the absence of a specific step depending where in the notation the 'x' is placed. For example, SV-10-x-140 represents silica vesicles which were synthesised via a first step at 10° C., the second step was not carried out but instead the vesicles were subjected to a hydrothermal treatment at 140° C. in a third step, as defined herein.

In a first aspect of the invention, there is provided a method of producing hollow silica vesicles including the steps of:
(a) producing a silica formulation by adding a hydrolysable silica source to an aqueous solution comprising a block copolymer, the silica formulation being maintained at a temperature of less than 20° C., and agitating the formulation until silica-polymer composite vesicles form, followed by step (b) or step (c);
(b) raising the temperature of the silica formulation containing the silica-polymer composite vesicles to be between 25° C. to 100° C. and agitating the mixture to form silica-polymer composite vesicles having spherical structures within the vesicle walls;
(c) exposing the vesicles to a hydrothermal treatment; and
(d) calcining the vesicles,
to thereby produce the silica vesicles.

The hydrolysable silica source is suitably of the general formula $[(X_1)(X_2)Si(X_3)(X_4)]$. Each X group is not particularly restricted except that at least two are hydrolysable. Preferably, three of the four X groups are hydrolysable and, more preferably, all of the X groups are hydrolysable. Each X may be different but is an organic group which is selected from the group consisting of a $C_1$-$C_{10}$ alkoxy substituted or unsubstituted, an aryloxy substituted or unsubstituted, a $C_1$-$C_{10}$ alkyl substituted or unsubstituted or aryl substituted or unsubstituted, a $C_1$-$C_{10}$ alkenyl substituted or unsubstituted. Preferably, the alkoxy, alkenyl and alkyl groups referred to are $C_1$-$C_8$ groups inclusive of $C_2$-$C_8$ groups, $C_3$-$C_8$ groups, $C_4$-$C_8$ groups, $C_5$-$C_8$ groups, $C_6$-$C_8$ groups and $C_7$ or $C_8$ groups. More preferably the alkoxy, alkenyl and alkyl groups are $C_1$-$C_6$ groups inclusive of $C_2$-$C_6$ groups, $C_3$-$C_6$ groups, $C_4$-$C_6$ groups and $C_5$ and $C_6$ groups. Even more preferably the alkoxy, alkenyl and alkyl groups are $C_1$-$C_4$ groups inclusive of $C_2$-$C_4$ groups and $C_3$ and $C_4$ groups. Still more preferably the alkoxy, alkenyl and alkyl groups may be $C_1$-$C_3$ inclusive of $C_1$, $C_2$ and $C_3$ groups. Yet still more preferably the alkoxy, alkenyl and alkyl groups may be selected from the group consisting of methyl, ethyl, propyl, isopropyl, butyl, s- and t-butyl groups.

In one preferred embodiment, the hydrolysable silica source is such that all four X groups are $C_1$-$C_6$ alkoxy groups inclusive of $C_2$-$C_6$, $C_3$-$C_6$, $C_4$-$C_6$ and $C_5$ and $C_6$ as well as $C_1$-$C_4$, $C_2$-$C_4$ and $C_3$ and $C_4$ and $C_1$ and $C_2$ groups. Preferably, the hydrolysable silica source is an alkylorthosilicate which may be optionally substituted. Preferably, the alkylorthosilicate is selected from the group consisting of tetramethylorthosilicate, tetrethylorthosilicate, tetrapropylorthosilicate and tetrabutylorthosilicate, all of which may be optionally substituted.

The term "alkyl" refers to optionally substituted linear and branched hydrocarbon groups having 1 to 10 carbon atoms. Where appropriate, the alkyl group may have a specified number of carbon atoms, for example, $C_1$-$C_8$ alkyl or $C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl, tridecyl, tetradecyl, pentadecyl.

The term "alkenyl" refers to optionally substituted unsaturated linear or branched hydrocarbon groups, having 2 to 10 carbon atoms and having at least one carbon-carbon double bond. Where appropriate, the alkenyl group may have a specified number of carbon atoms, for example, $C_2$-$C_8$ alkenyl or $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-I,3-diene, hex-I,3-diene, non-I,3,5-triene and the like.

The term "alkoxy" as used herein means straight or branched chain alkyl groups linked by an oxygen atom (i.e., —O-alkyl) to the silicon atom, wherein alkyl is as described above. The term "aryloxy" as used herein has a similar meaning with an aryl group, as defined below, replacing the alkyl group.

The term "aryl" as used herein means a stable monocyclic, bicyclic, or tricyclic carbon ring of up to 8 members in each ring, wherein at least one ring is aromatic as defined by the Hückel 4n+2 rule.

The term "optionally substituted" includes substitution of the group referred to with one or more groups selected from the group consisting of, but not limited to alkyl, alkenyl, aryl, amine, amino, halide, thio, hydroxy and carboxyl groups. Those skilled in the art will appreciate that other groups may be used for substitution.

By way of non-limiting example only, the hydrolysable silica source may be selected from the group consisting of one or more of: methyltrimethoxysilane, methyltriethoxysilane, methyltri-n-propoxysilane, methyltri-iso-propoxysilane, methyltri-n-butoxysilane, methyltri-sec-butoxysilane, methyltri-tert-butoxysilane, ethyltrimethoxysilane, ethyltriethoxysilane, ethyltri-n-propoxysilane, ethyltri-iso-propoxysilane, ethyltri-n-butoxysilane, ethyltri-sec-butoxysilane, ethyltri-tert-butoxysilane, n-propyltrimethoxysilane, n-propyltriethoxysilane, n-propyltri-n-propoxysilane, n-propyltri-iso-propoxysilane, n-propyltin-n-butoxysilane, n-propyltri-sec-butoxysilane, n-propyltri-tert-butoxysilane, isopropyltrimethoxysilane, isopropyltriethoxysilane, isopropyltri-n-propoxysilane, isopropyltriisopropoxysilane, isopropyltri-n-butoxysilane, isopropyltri-sec-butoxysilane, isopropyltri-tert-butoxysilane, n-butyltrimethoxysilane, n-butyltriethoxysilane, n-butyltri-n-propoxysilane, n-butyltriisopropoxysilane, n-butyltri-n-butoxysilane, n-butyltri-sec-butoxysilane, n-butyltri-tert-butoxysilane, sec-butyltrimethoxysilane, sec-butyltriethoxysilane, sec-butyltri-n-propoxysilane, sec-butyltriisopropoxysilane, sec-butyltri-n-butoxysilane, sec-butyltri-sec-butoxysilane, sec-butyltri-tert-butoxysilane, tert-butyltrimethoxysilane, tert-butyltriethoxysilane, tert-butyltri-n-propoxysilane, tertbutyltriisopropoxysilane, tert-butyltri-n-butoxysilane, tert-butyltri-sec-butoxysilane, tert-butyltri-tert-butoxysilane, isobutyltrimethoxysilane, isobutyltriethoxysilane, isobutyltri-n-propoxysilane, isobutyltriisopropoxysilane, isobutyltri-n-butoxysilane, isobutyltri-sec-butoxysilane, isobutyltri-tert-butoxysilane, n-pentyltrimethoxysilane, n-pentyltriethoxysilane, n-pentyltri-n-propoxysilane, n-pentyltriisopropoxysilane, n-pentyltri-n-butoxysilane, n-pentyltri-sec-butoxysilane, n-pentyltri-tert-butoxysilane, sec-pentyltrimethoxysilane, sec-pentyltriethoxysilane, sec-pentyltri-n-propoxysilane, sec-pentyltriisopropoxysilane, sec-pentyltri-n-butoxysilane, sec-pentyltri-sec-butoxysilane, sec-pentyltri-tert-butoxysilane, tert-pentyltrimethoxysilane, tert-pentyltriethoxysilane, tert-pentyltri-n-propoxysilane, tert-pentyltriisopropoxysilane, tert-pentyltri-n-butoxysilane, tert-pentyltri-sec-butoxysilane, tert-pentyltri-tert-butoxysilane, isopentyltrimethoxysilane, isopentyltriethoxysilane, isopentyltri-n-propoxysilane, isopentyltriisopropoxysilane, isopentyltri-n-butoxysilane, isopentyltri-sec-butoxysilane, isopentyltri-tert-butoxysilane, neo-pentyltrimethoxysilane, neo-pentyltriethoxysilane, neo-pentyltri-n-propoxysilane, neo-pentyltriisopropoxysilane, neo-pentyltri-n-butoxysilane, neo-pentyltri-sec-butoxysilane, neo-pentyltri-neo-butoxysilane, phenyltrimethoxysilane, phenyltriethoxysilane, phenyltri-n-propoxysilane, phenyltriisopropoxysilane, phenyltri-n-butoxysilane, phenyltri-sec-butoxysilane, phenyltri-tert-butoxysilane, dimethyldimethoxysilane, dimethyldiethoxysilane, dimethyldi-n-propoxysilane, dimethyldiisopropoxysilane, dimethyldi-n-butoxysilane, dimethyldi-sec-butoxysilane, dimethyidi-tert-butoxysilane, diethyldimethoxysilane, diethyidiethoxysilane, diethyldi-n-propoxysilane, diethyldiisopropoxysilane, diethyldi-n-butoxysilane, diethyldi-sec-butoxysilane, diethyidi-tert-butoxysilane, di-n-propyldimethoxysilane, di-n-propyldimethoxysilane, di-n-propyidi-n-propoxysilane, di-n-propyldiisopropoxysilane, di-n-propyldi-n-butoxysilane, di-n-propyldi-sec-butoxysilane, di-n-propyidi-tert-butoxysilane, diisopropyldimethoxysilane, diisopropyidiethoxysilane, diisopropyldi-n-propoxysilane, diisopropyldiisopropoxysilane, diisopropyldi-n-butoxysilane, diisopropyldi-sec-butoxysilane, diisopropyidi-tert-butoxysilane, di-n-butyldimethoxysilane, di-n-butyldiethoxysilane, di-n-butyldi-n-propoxysilane, di-n-butyidiisopropoxysilane, di-n-butyldi-n-butoxysilane, di-n-butyldi-sec-butoxysilane, di-n-butyldi-tert-butoxysilane, di-sec-butyldimethoxysilane, di-sec-butyidiethoxysilane, di-sec-butyldi-n-propoxysilane, di-sec-butyidiisopropoxysilane, di-sec-butyldi-n-butoxysilane, di-sec-butyldi-sec-butoxysilane, di-sec-butyidi-tert-butoxysilane, di-tert-butyldimethoxysilane, di-tert-butyidiethoxysilane, di-tert-butyldi-n-propoxysilane, di-tert-butyldiisopropoxysilane, di-tert-butyidi-n-butoxysilane, di-tert-butyidi-sec-butoxysilane, di-tert-butyldi-tert-butoxysilane, diphenyldimethoxysilane, diphenyidiethoxysilane, diphenyldi-n-propoxysilane, diphenyldiisopropoxysilane, diphenyldi-n-butoxysilane, diphenyldi-sec-butoxysilane, diphenyldi-tert-butoxysilane, methyineopentyidimethoxysilane, methylneopentyldiethoxysilane, methyldimethoxysilane, ethyldimethoxysilane, n-propyldimethoxysilane, isopropyldimethoxysilane, n-butyldimethoxysilane, sec-butyldimethoxysilane, tert-butyidimethoxysilane, isobutyidimethoxysilane, n-pentyidimethoxysilane, sec-pentyldimethoxysilane, tert-pentyidimethoxysilane, isopentyidimethoxysilane, neopentyidimethoxysilane, neohexyldimethoxysilane, cyclohexyldimethoxysilane, phenyldimethoxysilane, methyldiethoxysilane, ethyidiethoxysilane, n-propyldiethoxysilane, isopropyldiethoxysilane, n-butyldiethoxysilane, sec-butyidiethoxysilane, tert-butyidiethoxysilane, isobutyldiethoxysilane, n-pentyldiethoxysilane, sec-pentyldiethoxysilane, tert-pentyidiethoxysilane, isopentyldiethoxysilane, neopentyldiethoxysilane, neohexyldiethoxysilane, cyclohexyldiethoxysilane, phenyidiethoxysilane, trimethoxysilane, triethoxysilane, tri-n-propoxysilane, triisopropoxysilane, tri-n-butoxysilane, tri-sec-butoxysilane, tri-tert-butoxysilane. Of the above compounds, the preferred compounds are methyltrimethoxysilane, methyltriethoxysilane, methyltri-n-propoxysilane, methyltriisopropoxysilane, ethyltrimethoxysilane, ethyltriethoxysilane, dimethyldimethoxysilane, dimethyldiethoxysilane, diethyldimethoxysilane and diethyldiethoxysilane.

The hydrolysable silica source may be an oligomer formed by reaction of one or more types of monomer described by the above formula or listed above.

Preferably, the aqueous solution is an aqueous buffer solution.

Suitably, the aqueous buffer solution is an acidic buffer solution. In a preferred embodiment the pH of the aqueous buffer solution is between 3 to 6, or between 3 to 5, preferably 4 to 5. In one preferred embodiment the aqueous buffer solution is a sodium acetate/acetic acid buffer solution.

Preferably, an inorganic salt is also present in the silica formulation. Suitable inorganic salts include sodium and potassium salts. Sodium sulphate and sodium chloride are two examples of preferred salts. It is postulated that a high ionic strength in the formulation improves the stability of larger vesicles and assists in maintaining uniformity. This is based on experimental observations that the vesicles, while still commercially useful, will become relatively small (30 nm) and show reduced uniformity in the absence of salts.

Preferably, the block copolymer is an olefinic block copolymer. A wide range of olefinic block copolymers are commercially available. More preferably, the block copolymer is a triblock copolymer i.e. of the A-B-A configuration. In one embodiment the triblock copolymer is a poly(alkylene$_1$ oxide)-poly(alkylene$_2$ oxide)-poly(alkylene$_1$ oxide) block copolymer wherein the alkylene$_1$ and alkylene$_2$ components may be independently selected from the group consisting of ethylene, propylene, butylene, pentylene, hexylene and derivatives, e.g. glycol derivatives, thereof.

Even more preferably, the block copolymer is a poly(ethylene oxide)-poly(alkylene oxide)-poly(ethylene oxide) block copolymer wherein the alkylene group is as described above for the alkylene$_1$ and alkylene$_2$ components. In preferred embodiments, the block copolymer is a poly(ethylene oxide)-poly(propylene oxide)-poly(ethylene oxide) or a poly(ethylene oxide)-poly(butylene oxide)-poly(ethylene oxide) block copolymer.

Preferably, in step (a), the silica formulation is maintained at a temperature of between 0° C. to 20° C., preferably between 5° C. to 15° C., more preferably at about 10° C. Between 0° C. to 20° C. may include ranges of between 0° C. to 15° C., 0° C. to 12° C., 5° C. to 20° C., 5° C. to 15° C., 7° C. to 13° C. and is inclusive of temperatures of about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C. and 20° C. or of ranges from any one of those values to another one of those values.

Suitably, the agitation of the mixture in step (a) is stirring. Preferably, the stirring until formation of the silica-polymer composite vesicle occurs is continuous stirring for a first predetermined period of time. The first predetermined period of time may be determined experimentally by observation of the reaction mixture by known techniques such as TEM until formation of the silica-polymer composite vesicles is observed. Failure to continuously stir the formulation may lead to phase separation of the formulation into to layers which disrupts formation of the vesicles.

Suitably, the silica formulation is stirred for a significant portion of, preferably the majority of, more preferably a substantial portion of and even more preferably for substantially all of the first predetermined period of time.

By "a significant portion of" it is intended that stirring be continuous for at least the first 20% of the first predetermined period of time. By "the majority of" it is intended that stirring be continuous for at least the first 50% of the first predetermined period of time. By "a substantial portion of" it is intended that stirring be continuous for at least the first 75% of the first predetermined period of time. By "substantially all of" it is intended that stirring be continuous for at least the first 80%, preferably 90% of the first predetermined period of time.

The inventors have surprisingly found that continuous stirring is a critical aspect of at least the first step and it is important that continuous stirring be maintained until the majority of the initial silica-polymer composite vesicles have formed. They have shown experimentally that, with other conditions maintained the same, if the reaction is carried out without stirring then the desired vesicles fail to form and amorphous silica results. This is described in the experimental section.

Preferably, the first predetermined period of time is at least 5 hours, more preferably at least 10 hours, even more preferably at least 15 hours, still more preferably at least 20 hours. In one preferred embodiment, the first predetermined period of time is about 24 hours or more.

Suitably, in step (b), the temperature is raised to be between 30° C. to 90° C., preferably between 30° C. to 85° C., more preferably between 35° C. to 80° C. Between 30° C. to 90° C. may include ranges of between 30° C. to 80° C., 30° C. to 75° C., 30° C. to 70° C., 40° C. to 90° C., 40° C. to 85° C., 40° C. to 80° C., 40° C. to 75° C., 40° C. to 70° C. and is inclusive of temperatures of about 30° C., 35° C., 40° C., 45° C., 50° C., 55° C., 60° C., 65° C., 70° C., 75° C., 80° C., 85° C. and 90° C. or of ranges from any one of those values to another of those values.

Suitably, the agitation of the mixture in step (b) is stirring. Preferably, the stirring is continued until formation of spherical structures are generated inside the walls of the silica-polymer composite vesicles. This formation may occur after continuous stirring for a second predetermined period of time.

Preferably, the second predetermined period of time is between about 0.1 to about 6.0 hours, preferably between about 0.5 to about 5.0 hours, more preferably between about 1.0 to about 4.0 hours, even more preferably between about 2.0 to about 3.0 hours. The second predetermined period of time can also be determined experimentally, as for the first predetermined period of time, and can be taken to be at an end when a suitable percentage of the vesicles with wall spherical structures, for example when greater than 90%, 95% or 98% of said vesicles are formed.

The inventors have found that the heating in step (b) at moderate/intermediate temperature is the period during which pore wall structure formation occurs, i.e. the formation of hollow spherical bodies within the wall structure, and the elevated temperature over that in step (a) is critical to achieve the desired vesicle wall morphology. Without wishing to be limited by theory, the inventors believe that at the completion of step (a) the silica species in the silica-polymer composite vesicle may not be fully hydrolysed, still retaining some of their silica precursor organic groups and consequently a degree of hydrophobicity. Under these conditions, the lamellar structure of the block copolymer is favoured. However with step (b), the degree of hydrolysis of the silica precursor is increased such that the surface of the silica becomes more dominated by the hydroxyl terminated groups typical of silica surfaces, and therefore, more hydrophilic. With this decrease in wall hydrophobicity, the surfactant conformation can change to the more curved structures such as spherical micelles favoured under hydrophilic conditions. This results in the formation of vesicle wall pores with a spherical structure. It will be appreciated by those skilled in the art that depending on the selection of the surfactant, temperature, water content, degree of silica precursor hydrolysis and other factors, curved surfactant structures other than spherical micelles may be formed at step (b) and as such, the porosity of the vesicle walls may take on the shape of these curved surfactant structures. Curved surfactant structures that may form as an alternative to spherical micelles include but are not limited to hexagonal rods and cubic phases including bi-continuous cubic phases. The extent of curved surfactant structures that may be formed will be well understood by those skilled in surfactant liquid crystal behaviour.

However, in one embodiment, the method includes step (a) followed by step (c) prior to calcining the vesicles. Here, it is step (c), the hydrothermal step, that is key in forming the larger spherical pores in the walls of the vesicles. In cases where pore sizes only at the larger end of the range provided by the methods of the present invention are desired, step (b) (which without the following hydrothermal step produces smaller pore sizes) may be omitted from the method.

In one highly preferred embodiment, the method includes step (a) followed by step (b) followed by step (c), prior to calcining the vesicles. That is, the silica formulation of step (a) is exposed to step (b) and it is the silica-polymer composite vesicles having spherical structures within the vesicle walls, as a product of step (b), which are then exposed to step (c).

Preferably, the hydrothermal treatment of step (c), for all embodiments, is carried out at a temperature which is greater than 90° C. and less than 200° C., preferably greater than 90° C. and less than 180° C., more preferably greater than 95° C. and less than 160° C., for example about 100° C. to about 160° C. In certain embodiments the hydrothermal treatment may be carried out at a temperature which is between 100° C. and 200° C., preferably between 100° C. and 180° C., more preferably between 100° C. and 160° C. Temperatures of about 100° C., 105° C., 110° C., 115° C., 120° C., 125° C., 130° C., 135° C., 140° C., 145° C., 150° C., 155° C. and 160° C. are considered useful.

Preferably, the hydrothermal treatment step is carried out for a third predetermined period of time until formation of the silica-polymer composite vesicles with entrances which are formed throughout the siliceous walls.

Preferably, the third period of time is generally equivalent to those periods described for the first period of time.

Suitably, the hydrothermal step (c) is carried out at an elevated pressure. Preferably, the elevated pressure is greater than 0.7 bar and less than 15.5 bar inclusive of 1.1 bar to 15.0 bar, 1.5 bar to 12.0 bar, 1.5 bar to 10.0 bar, 1.5 bar to 8.0 bar, 1.5 bar to 6.0 bar and 1.5 bar to 5.0 bar. In one embodiment the elevated pressure is greater than 0.7 bar and less than 10 bar, more preferably greater than 0.8 bar and less than 6 bar, for example about 1 bar to about 6 bar.

Figure 3:
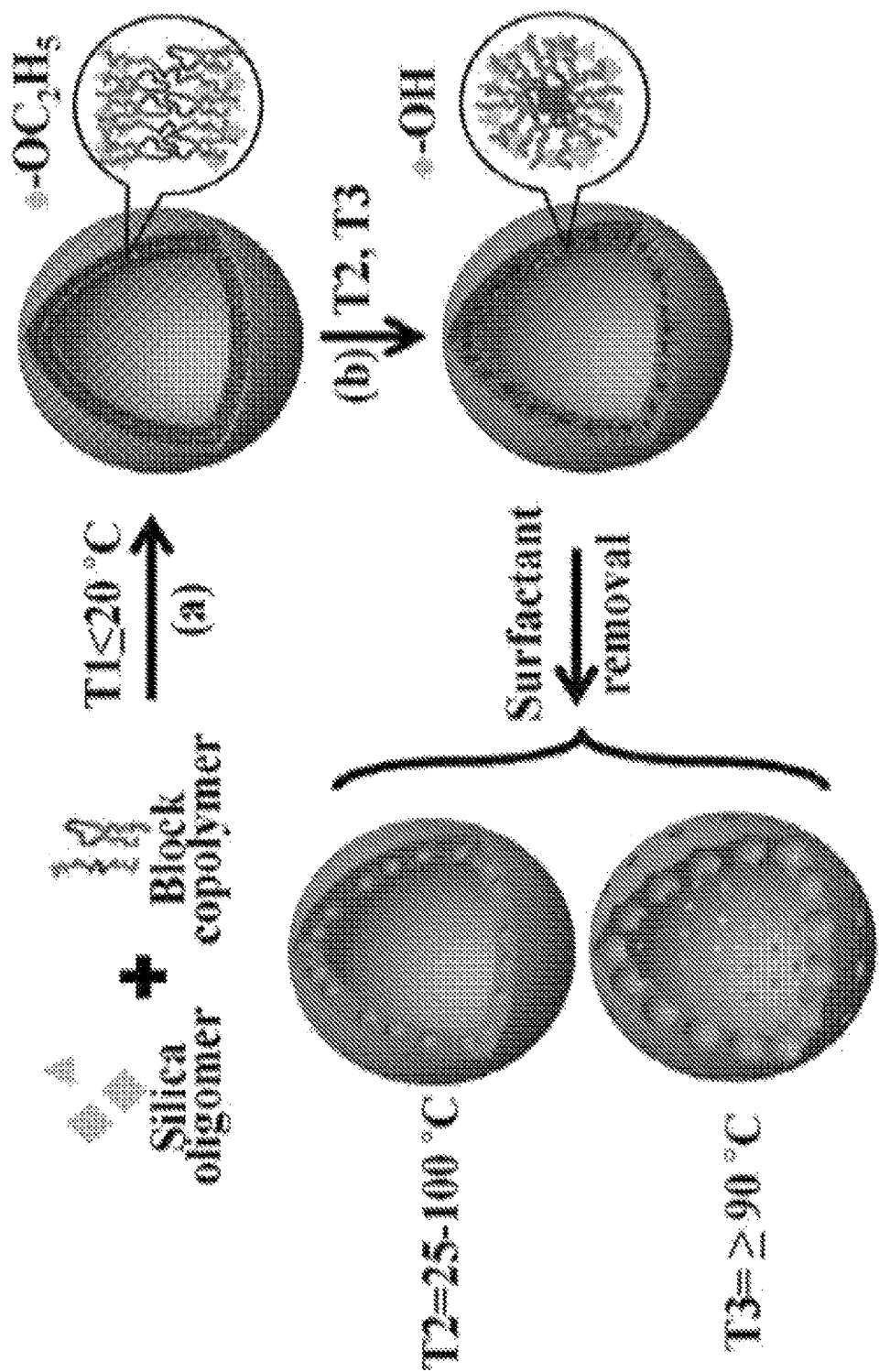
FIG. 3 is a proposed scheme showing the formation of the silica vesicles throughout three synthetic steps.

As indicated in FIG. 3, carrying out step (b) without the additional hydrothermal step may result in the formation of relatively small pores in the vesicle walls, typically with diameters lower than 4 nm. These pores are largely formed by microcracks in the vesicle walls and the microcracks may be associated with small internal spherical cavities in the wall of the vesicle such that these cavities are connected with the internal cavity of the vesicle and the outside of the vesicle, forming a continuous pore path through the vesicle wall. Carrying out the hydrothermal step, with or without the inclusion of step (b) (that is, following step (a) or step (b)) may result in the formation of larger pores in the walls of the vesicles as shown in FIG. 3. Thus, while either step (b) or step (c) may directly follow step (a) and be followed by calcination to produce useful and commercially valuable products it is preferred that step (a) is followed by step (b) which is itself followed by step (c) and then, finally, calcination to produce silica vesicles with fine control over morphology.

Suitably, the calcination is carried out at any temperature suitable to remove the copolymer template and typically would be carried out at greater than 400° C., preferably greater than 500° C., even more preferably about 550° C.

Those skilled in the art will understand that references made to the silica formed at the various stages of the processes of the present invention may refer to silicon-oxygen based materials such as partially condensed and hydrated forms of silicon-oxygen based species since silica of the approximate composition $SiO_2$ would not expect to be fully formed until calcination is carried out. The silicon-oxygen based materials formed at the different stages of the processes of the present invention are well known to those knowledgeable of the formation of silica from the silica precursors described herein using known pathways such as hydrolysis and condensation.

A surface modification of the silica vesicles may be optionally carried out following the calcination step. This typically involves increasing the hydrophobicity of the surface of the silica vesicle which has been found to increase the loadable amount of certain proteins and drug compounds. Surface modification may be applied to the outer or inner surfaces of the silica vesicles, or both. In one highly preferred embodiment, the method includes, after calcination of the silica vesicles, the step of modifying the silica vesicle with appropriate functional groups. Preferably, the surface modification is a hydrophobic modification.

The chemical agent used to modify the silica vesicle surface may be a hydrolysable silica source with the general formula $[(X_1)(X_2)Si(X_3)(X_4)]$. Each X group is not particularly restricted except that at least one is hydrolysable and at least one is a hydrophobic functional group. Each hydrolysable X may be different but is an organic group which is selected from the group consisting of a $C_1$-$C_4$ alkoxy, substituted or unsubstituted, and halogen substituent groups. Preferably, the alkoxy groups referred to are methoxyl and ethoxyl groups. More preferably the alkoxy groups are methoxyl groups. Preferably, the halogen groups referred to are chloride and bromide groups. More preferably the halogen groups are chloride groups. Alternatively, each hydrophobic functional X group may be different but is an organic group which is selected from the group consisting of a $C_1$-$C_{20}$ alkyl substituted or unsubstituted. The hydrolysable silica source used to impart surface modification of the silica vesicles may include, but is not limited to, one or a combination of two or more of the following compounds: methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, hexyltrimethoxysilane, hexyltriethoxysilane, heptanyltrimethoxysilane, heptanyltriethoxysilane, octyltrimethoxysilane, octyltriethoxysilane, nonanyltrimethoxysilane, nonanyltriethoxysilane, decanyltrimethoxysilane, decanyltriethoxysilane, undecyltrimethoxysilane, undecyltriethoxysilane, dodecyltrimethoxysilane, dodecyltriethoxysilane, tridecyltrimethoxysilane, tridecyltriethoxysilane, tetradecyltrimethoxysilane, tetradecyltriethoxysilane, pentadecyltrimethoxysilane, pentadecyltriethoxysilane, cetyltrimethoxysilane, cetyltriethoxysilane, heptadecyltrimethoxysilane, heptadecyltriethoxysilane, octadecyltrimethoxysilane, octadecyltriethoxysilane, phenyltrimethoxysilane, phenyltriethoxysilane, dimethyldimethoxysilane, dimethyldiethoxysilane, diethyldimethoxysilane, diethyldiethoxysilane, dipropyldimethoxysilane, dipropyldiethoxysilane, dibutyldimethoxysilane, dibutyldiethoxysilane, dipentyldimethoxysilane, dipentyldiethoxysilane, dihexyldimethoxysilane, dihexyldiethoxysilane, diheptanyldimethoxysilane, diheptanyldiethoxysilane, dioctyldimethoxysilane, dioctyldiethoxysilane, dinonanyldimethoxysilane, dinonanyldiethoxysilane, didecanyldimethoxysilane, didecanyldiethoxysilane, diundecyldimethoxysilane, diundecyldiethoxysilane, didodecyldimethoxysilane, didodecyldiethoxysilane, ditridecyldimethoxysilane, ditridecyldiethoxysilane, ditetradecyldimethoxysilane, ditetradecyldiethoxysilane, dipentadecyldimethoxysilane, dipentadecyldiethoxysilane, dicetyldimethoxysilane, dicetyldiethoxysilane, diheptadecyldimethoxysilane, diheptadecyldiethoxysilane, dioctadecyldimethoxysilane, dioctadecyldiethoxysilane, diphenyldimethoxysilane, diphenyldiethoxysilane, ethylmethyldimethoxysilane, ethylmethyldiethoxysilane, propylmethyldimethoxysilane, propylmethyldiethoxysilane, butylmethyldimethoxysilane, butylmethyldiethoxysilane, pentylmethyldimethoxysilane, pentylmethyldiethoxysilane, hexylmethyldimethoxysilane, hexylmethyldiethoxysilane, heptanylmethyldimethoxysilane, heptanylmethyldiethoxysilane, octylmethyldimethoxysilane, octylmethyldiethoxysilane, nonanylmethyldimethoxysilane, nonanylmethyldiethoxysilane, decanylmethyldimethoxysilane, decanylmethyldiethoxysilane, undecylmethyldimethoxysilane, undecylmethyldiethoxysilane, dodecylmethyldimethoxysilane, dodecylmethyldiethoxysilane, tridecylmethyldimethoxysilane, tridecylmethyldiethoxysilane, tetradecylmethyldimethoxysilane, tetradecylmethyldiethoxysilane, pentadecylmethyldimethoxysilane, pentadecylmethyldiethoxysilane, cetylmethyldimethoxysilane, cetylmethyldiethoxysilane, heptadecylmethyldimethoxysilane, heptadecylmethyldiethoxysilane, octadecylmethyldimethoxysilane, octadecylmethyldiethoxysilane, phenylmethyldimethoxysilane, phenylmethyldiethoxysilane, trimethyichiorosilane, ethyldimethyichiorosilane, propyldimethyichiorosilane, butyldimethyichiorosilane, pentyldimethyichiorosilane, hexyldimethyichiorosilane, heptanyldimethyichiorosilane, octyldimethylchlorosilane, nonanyldimethylchlorosilane, decanyldimethylchlorosilane, undecyldimethylchlorosilane, dodecyldimethylchlorosilane, tridecyldimethyichiorosilane, tetradecyldimethylchlorosilane, pentadecyldimethyichiorosilane, cetyldimethylchlorosilane, heptadecyldimethylchlorosilane, octadecyldimethylchlorosilane, phenyldimethylchlorosilane, phenethyldimethylchlorosilane, dimethyldichlorosilane, ethylmethyldichlorosilane, propylmethyldichlorosilane, butylmethyldichlorosilane, pentylmethyldichlorosilane, hexyldimethyldichlorosilane, heptanylmethyldichlorosilane, octylmethyldichlorosilane, nonanylmethyldichlorosilane, decanylmethyldichlorosilane, undecylmethyldichlorosilane, dodecylmethyldichlorosilane, tridecylmethyldichlorosilane, tetradecylmethyldichlorosilane, pentadecylmethyldichlorosilane, cetylmethyldichiorosilane, heptadecylmethyldichlorosilane, octadecylmethyldichlorosilane, phenylmethyldichiorosilane, phenethylmethyldichlorosilane, methyltrichlorosilane, ethyltrichlorosilane, propyltrichlorosilane, butyltrichlorosilane, pentyltrichiorosilane, hexyltrichlorosilane, heptanyltrichlorosilane, octyltrichlorosilane, nonanyltrichlorosilane, decanyltrichlorosilane, undecyltrichlorosilane, dodecyltrichlorosilane, tridecyltrichlorosilane, tetradecyltrichlorosilane, pentadecyltrichlorosilane, cetyltrichlorosilane, heptadecyltrichlorosilane, octadecyltrichlorosilane, phenyltrichlorosilane, phenethyltrichlorosilane.

Suitably, surface modification of the silica vesicles is carried out by combining the silica vesicles with the hydrolysable agent used for surface modification in a suitable media to facilitate either a gas phase or liquid phase reaction. In the case where the surface modification is carried out in a liquid phase medium, the silica vesicles are added to an appropriate solvent (for the hydrolysable silica source) and agitation of the mixture containing the silica vesicles may be carried out before and/or after the addition of the hydrolysable agent used for surface modification. Alternatively, the silica vesicles may be added to a solvent already containing the agent to be used to effect the hydrophobic modification. Preferably, the agitation of the mixture in surface modification step is carried out by stirring or ultrasonication. More preferably, the agitation of the mixture in the surface modification step is carried out by stirring.

Suitably, in the surface modification step, the temperature may be raised to be between 80° C. and 120° C., preferably between 100° C. and 120° C., more preferably between 105° C. and 115° C.

Suitably, the surface modification step may be carried out in one or a combination of two or more organic solvents. Solvents that may be used include, but are not limited to one or a combination of two or more of the following: pentane, 2-methylbutane, neopentane, n-hexane, 2-methylpentane, 3-methylpentane, 2,2-dimethylbutane, 2,3-dimethylbutane, n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, octane, 2-methylheptane, 3-methylheptane, 4-methylheptane, 3-ethylhexan, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2,2,3-trimethylpentane, 2,2,4-trimethylpentane, 2,3,3-trimethylpentane, 2,3,4-trimethylpentane, tetramethylbutane, nonane, decane, undecane, dodecane, ethanol, propan-1-ol, isopropyl alcohol, butyl alcohol, pentanol, hexan-1-ol, heptan-1-ol, octan-1-ol, nonan-1-ol, decan-1-ol, undecan-1-ol, dodecan-1-ol, benzene, toluene, ethylbenzene, 1,2-dimethylbenzene, 1,3-dimethylbenzene, 1,4-dimethylbenzene, n-propylbenzene, 1,2,3-trimethylbenzene, 1,3,5-trimethylbenzene, 1,2,4-trimethylbenzene, benzyl alcohol. Preferably, the solvents are $C_5$-$C_{16}$ alkanes substituted or unsubstituted, $C_2$-$C_{12}$ alcohols or aromatic compounds which are $C_1$-$C_3$ substituted or unsubstituted. More preferably, the solvents are $C_2$-$C_8$ alcohols or aromatic compounds which are $C_1$-$C_3$ substituted, even more preferably $C_2$-$C_5$ alcohols or $C_1$-$C_3$ substituted benzene. The solvent is preferably octane, ethanol, propan-1-ol, isopropyl alcohol or toluene or a combination of one or more of these.

Figure 8:
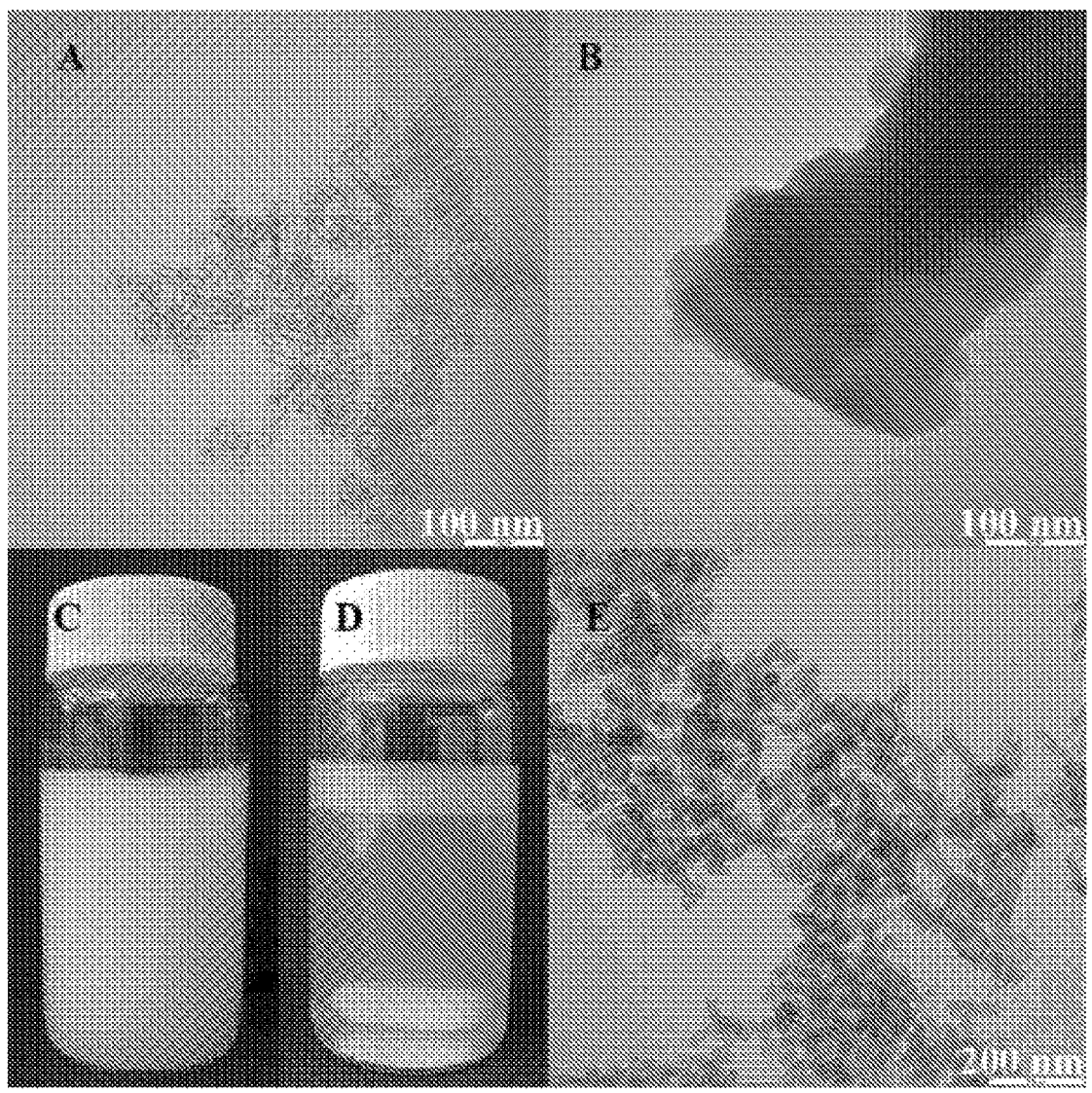
FIG. 8 is a series of TEM images of (A) SV-10-x-100-l (aqueous layer), (B) SV-10-x-100-u (TEOS layer) and (E) SV-20-x-100 after calcinations and (C, D) are images of the reaction mixture after step 1 with continuous stirring (C) or with only 10 min stirring and 24 h of static conditions (D)

For the formation of the silica vesicles the results presented in the experimental section, and particularly those shown in FIG. 8, clearly indicate that continuous stirring, until the silica-polymer vesicles are formed, and low temperature are two key parameters for the formation of vesicular structure and high yield.

In the self-assembly of surfactants, the structure of supramolecular aggregates is predicted mainly by the g factor of organic surfactant molecules. The inventors have demonstrated that in PEO—PBO-PEO type block copolymer templating systems, cooperatively self-organized block copolymer/silicate composite structures can be influenced by the hydrophobicity/hydrophilicity of silica precursors. Specifically, the inventors postulate that temperature, in this instance the relatively low temperature of the first step, will influence the hydrolysis rate of TEOS which in turn influences the hydrophobicity/hydrophilicity of the forming silica oligomer and so influences the self-assembly of the vesicular structure. In synthesis step (a) higher temperatures lead to a faster hydrolysis rate of TEOS, which gives rise to hydrophilic silica oligomers and hence undesired generation of tubular and amorphous silica structures whereas lower temperatures, as previously defined, can produced the desired vesicle structure. Although high temperature hydrothermal treatment can alter the pore entrance size, direct hydrothermal treatment after step (a) prohibits the formation of spherical bodies within the pore wall structure thereby producing a still commercially useful but less preferred vesicle structure. At moderate or 'intermediate' temperature, as in step (b), a sandwich-like silica/surfactant composite structure gives direct evidence that TEOS deposits on both sides of the surfactant layer to thereby give the silica-void-silica wall structure upon later removal of the polymer during calcination.

Figure 9:
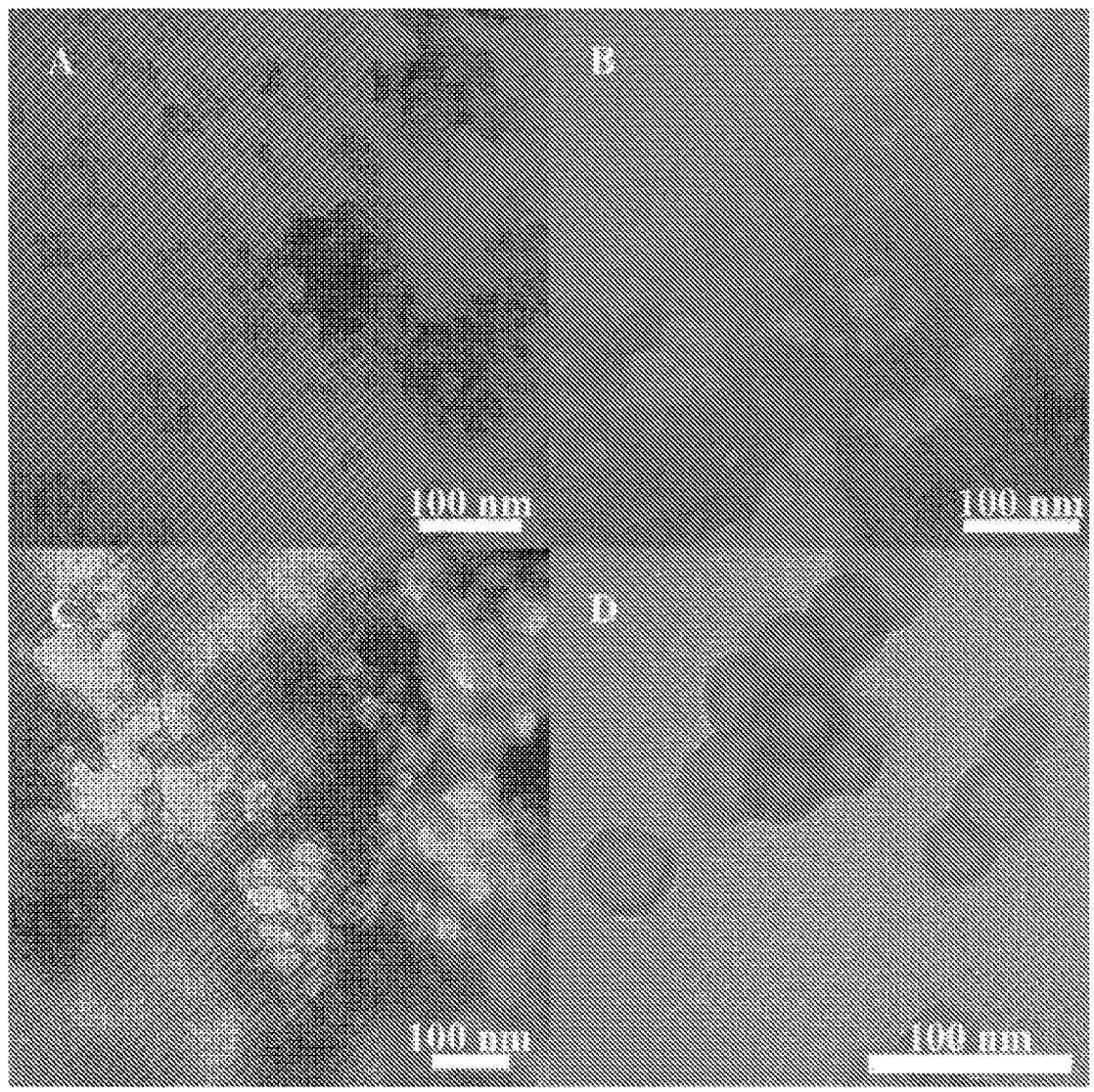
FIG. 9 is a series of cryo-TEM images of reaction solution at 10° C. (A) before adding TEOS and (B-D) after adding TEOS and after 12, 15 and 24 h, respectively.

In order to visualise the SV formation mechanism, Cryo-TEM was used to investigate the forming vesicle structure at different times throughout the process. As indicated in FIG. 9A, the block copolymer surfactant is in micelle form with a diameter less than 10 nm, before adding the silica source (TEOS). This shows that the present method does not use a pre-formed vesicular template in the synthesis but rather the formation of silica vesicles is a cooperative self-assembly of surfactant and silica oligomers. 15 h after adding the TEOS, self-assembled silica-surfactant vesicles can be observed (FIG. 9C), however, no pore wall structure is observed at the end of step 1 (FIG. 9D). It is also clear that the spherical bodies in the pore wall structure are formed only in a post treatment at moderate temperature i.e. step (b) or T2 (as represented in FIG. 3).

According to a second aspect of the invention there is provided a silica vesicle having:
  (a) a particle diameter of between 30 to 70 nm;
  (b) a wall structure perforated by spherical pores; and
  (c) an average pore entrance size of between 4 to 40 nm formed in the wall.

Preferably, the particle diameter is between 40 to 60 nm, more preferably about 45 to 55 nm, even more preferably about 50 nm. This is an ideal size to promote cellular uptake of the vesicle, and accompanying chemical or biological agents, via endocytosis.

Suitably, the average pore entrance size is between 5 to 38 nm, more preferably between about 6 to about 34 nm. The preferred pore entrance size will depend on the size of the protein or other drug or biomolecule to be accommodated. For example, for cytochrome C and ribonuclease A which both have a size of approximately 3 nm, an SV with an average pore entrance size of about 6 nm will be preferred. For applications where larger molecules need to be accommodated then SVs with an average pore entrance size of 8, 12, 16, 24 or 34 nm may be more appropriate.

The silica vesicle is a hollow silica vesicle.

Preferably, the hollow silica vesicle has a wall thickness of between 4 to 15 nm, more preferably between 5 to 14 nm, even more preferably between 7 to 13 nm.

A third aspect of the invention resides in a silica vesicle when produced by the method of the first aspect. The silica vesicles will have the physical characteristics already outlined for those of the second aspect.

According to a fourth aspect of the invention there is provided a drug or chemical delivery system comprising a silica vesicle of the second or third aspects and a drug or chemical agent encapsulated within the vesicle or bound to an outer surface thereof.

Preferably, the drug is an organic molecule and may include "biologic" molecules such as proteins and peptides and fragments thereof.

Preferably, the chemical agent is a pesticide such as a termiticide.

The drug or chemical agent may be adsorbed or bound onto the outer surface of the hollow silica vesicle, captured within the pores or encapsulated within the vesicle cavity. It may be covalently bonded but is preferably releasably bound such as by ionic attraction or electrostatic interactions or simply physically entrapped within the pore structure to thereby provide slow release characteristics.

A fifth aspect of the invention resides in an immunogenic composition comprising one or a plurality of silica vesicles of the second or third aspects and one or a plurality of immunogens and/or antigens.

The immunogen may be any molecule, protein, peptide, nucleic acid, carbohydrate, lipid or a fragment of any of these species which can, upon administration to a subject, elicits an immune response in the subject. In some embodiments, the immune response may be a protective immune response. The immunogen may be derived from a pathogen, cell, tissue or organ, may be a purified antigen, cell lysate or culture filtrate, or may be of recombinant or synthetic origin.

In one embodiment, the immunogen or antigen may be a combination of immunogens or antigens.

In one embodiment, the immunogenic composition is a vaccine composition.

In one embodiment, the immunogenic vaccine composition is a multi-valent vaccine composition.

In one embodiment, the immunogen is derived from a pathogenic virus, bacterium or other organism. Suitably, the pathogen from which the immunogen is derived is a single-stranded RNA virus. Preferably, the virus is selected from the group consisting of the families Flaviviridae, Hepacivirus, Pegivirus, Ephemerovirus, Rhabdoviridae and Pestivirus. In one preferred embodiment the virus is a pestivirus.

When the virus is a Ephemerovirus or Rhabdoviridae virus then it may be a bovine ephemeral fever-causing virus. Bovine ephemeral fever (BEF) is also known as Three Day Sickness in cattle. It is an arthropod vector-borne disease of cattle. The BEF virus is a negative, single stranded RNA genome with a lipid envelope and 5 structural proteins. The envelope glycoprotein G contains type-specific and neutralizing antigenic sites.

In certain embodiments, the immunogen may be derived from a species of the genus *Babesia*. Such a parasitic organism may be, for example, *Babesia bovis* or *Babesia bigemina.*

In certain embodiments, the immunogen may be derived from a species of the order Rickettsiales. The species may be of the genus *Anaplasma*, for example, *Anaplasma marginale*. Infection of cattle with *Anaplasma marginate* leads to a disease generally referred to as anaplasmosis.

It will be appreciated that the immunogenic composition of the present invention is not limited in the type of immunogen/antigen that it may be used with. Examples of antigens that may be used with the HSV drug delivery system include, but are not limited to, those used in the treatment or prophylaxis of adenovirus Type 4 and Type 7, anthrax, tuberculosis, diphtheria and tetanus, pertussis, Hepatitis B, poliovirus, *Haemophilus*, meningococcal disease, Hepatitis A, human papillomavirus, influenza, Japanese encephalitis, measles, mumps and rubella, pneumococcal disease, rabies, rotavirus, smallpox, typhoid, varicella, yellow fever, porcine circovirus, classical swine fever virus, equine influenza virus, foot and mouth disease virus, Newcastle disease virus, respiratory syncitial virus, parainfluenza virus 3, equine influenza virus, rabies virus, canine distemper virus, porcine contagious pleuropneumonia (caused by *Actinobacillus pleuropneumoniae*), canine babesiosis and canine visceral leishmaniasis.

In any one formulation of a product using the silica vesicles of the present invention, or any composition or aspect described herein relating to the use of the silica vesicles, more than one drug molecule or immunogen may be present. Here, combinations of different immunogens, combinations of different drug molecules or combinations of immunogens and drugs may be used in a single formulation. This enables the development of multi-valent vaccines, multi-drug combinations and drug vaccine combinations. Multi-drug combinations, multi-valent vaccines and drug vaccine combinations may be constructed by either mixing the pharmaceutically active molecules (that is, the drug molecules, immunogens or other molecules) together and then loading these into the silica vesicles such that individual vesicles may contain more than one type of active molecule, or alternatively, active molecules of a single type may be separately adsorbed (loaded) into separate lots of the silica vesicles and then the silica vesicles loaded with different active molecules may be combined into a single formulation. This latter approach allows different silica vesicle designs to be used with the different active molecules such that the release of each active molecule in a formulation may be independently tailored with respect to the release characteristics of the other active molecules in the formulation. For example, in a single formulation, silica vesicles with large pore entrance openings may be used for loading a large molecule such as a protein while small organic drug molecules in the same formulation may be accommodated within silica vesicles with smaller pore entrance openings to better moderate the controlled release of these small molecules, if desired. As another example, a multi-valent vaccine formulation may be constructed using hydrophobically-modified silica vesicles to maximise the loading of protein immunogens that have a strong hydrophobic character, while un-modified vesicles may be used to accommodate more hydrophilic immunogensin the same formulation. As an alternative strategy to constructing combination products, the silica vesicles may be sequentially loaded with different active molecules.

In one embodiment, the immunogenic composition comprises a plurality of silica vesicles which are of substantially the same character presenting or encapsulating plurality of immunogens which are of a different structural and/or functional character from one another.

In one embodiment, the immunogenic composition comprises a plurality of silica vesicles of a different structural character which are presenting or encapsulating immunogens which are of substantially the same structural and/or functional character.

It will be further appreciated by those skilled in the art that the immunogenic composition of the present invention may be formulated using any number or combination of excipient materials. These excipient materials may be included in a formulation for any number of reasons well known to those skilled in the art including, but not limited to, provide a stable formulation, improve flowability, adjust pH, allow easy reconstitution, stabilise antigen species, minimise adverse toxicological responses, improve manufacturability, increase stability or lifetime or allow easier administration, storage or transportation. Excipients that could be used to formulate a drug product containing the immunogenic composition of the present invention include, but are not limited to, acetone, alcohol, anhydrous lactose, castor oil, cellulose acetate phthalate, dextrose, D-fructose, D-mannose, FD&C Yellow #6 aluminium lake dye, fetal bovine serum, human serum albumin, magnesium stearate, micro-crystalline cellulose, plasdone C, polacrilin potassium, sodium bicarbonate, sucrose, aluminium hydroxide, amino acids, benzethonium chloride, formaldehyde, inorganic salts and sugars, vitamins, asparagine, citric acid, lactose, glycerin, iron ammonium citrate, magnesium sulfate, potassium phosphate, aluminium phosphate, formaldehyde, glutaraldehyde, 2-phenoxyethanol, glutaraidhyde, polysorbate 80, aluminium potassium sulfate, ammonium sulfate, bovine extract, gelatin, peptone, sodium phosphate, thimerosal, calf serum, glutaraldehyde, lactalbumin hydrolysate, neomycin sulfate, polymyxin B, lactalbumin hydrolysate, yeast extract, MRC-5 cellular protein, neomycin, polymyxin B sulphate, aluminium hydroxyphosphate sulphate, hemin chloride, mineral salts, nicotinamide adenine dinucleotide, potassium aluminium sulfate, sodium borate, soy peptone, phosphate buffers, polsorbate 20, sodium borate, lipids, sodium dihydrogen phosphate dehydrate, carbohydrates, L-histidine, Beta-propiolactone, calcium chloride, dibasic sodium phosphate, egg protein, monobasic potassium phosphate, monobasic sodium phosphate, polymyxin B, potassium chloride, sodium taurodeoxychoalate, gentamicin sulfate, hydrocortisone, octoxynol-10, a-tocopheryl hydrogen succinate, sodium deoxycholate, ovalbumin, nonylphenol ethoxylate, octylphenol ethoxylate (Triton X-100), arginine, dibasic potassium phosphate, egg protein, ethylene diamine tetraacetic acid, gentamicin sulfate, hydrolyzed porcine gelatin, monobasic potassium phosphate monosodium glutamate, protamine sulfate, sodium metabisulphite, phenol, casamino acid, sodium citrate, sodium phosphate monobasic monohydrate, sodium hydroxide, calcium carbonate, dextran, sorbitol, trehalose, sugar alcohols, polysaccharides, glucosamine, mannitol, polymers and xanthan.

Preferably, the immunogen is an immunogenic fragment of the bovine viral diarrhoea virus (BVDV). More preferably, the immunogen is the E2 protein, or a fragment thereof, of the BVDV. The structural envelope glycoprotein, E2, is a major immunogenic determinant, and is an ideal candidate as a subunit vaccine as immunisation with E2 evokes the production of neutralising antibodies. The neutralising antibodies produced by E2 after natural infection or vaccination is considered as the most important protective mediator against subsequent BVDV infection. Preferably, the E2 protein used in the immunogenic composition is a soluble, endotoxin free E2 generated using $E.\ coli$ expression. The E2 protein expressed in this way has been shown to be immunogenic in mice and sheep and was detectable by several BVDV-E2 specific antibodies. It is referred to herein as OptiE2 protein.

Bovine viral diarrhoea (BVD) is a prevalent cattle disease that causes serious mucosal lesions and clinical disorders such as reproductive, congenital defects and persistent infections. BVDV, commonly known as bovine pestivirus, is a single-stranded RNA virus which infects mostly cattle and some sheep. A major concern regarding pestivirus is not only limited to the substantial economic losses incurred but also to the fact that these viruses are not host specific signifying that they can easily spread amongst livestock such as sheep, pigs and goats. It has been well established that sheep and goats can be infected with BVDV and then transmit the virus back to cattle. BVDV has also been found in native bison and water buffalo populations.

Currently the available live and inactivated BVDV vaccines are relatively effective at preventing the majority of clinical diseases associated with acute infections, however these vaccines fail to completely protect against transmission by persistently infected animals. To date, Pestigard® (Pfizer) is the only BVDV vaccine approved for use in Australia. It is an inactivated viral vaccine with two antigenetically different Type 1 strains of BVDV, which have been isolated in Australia—Trangie and Bega. This vaccine needs to be administered as two doses, 6-8 weeks apart, with an annual booster injection required thereafter. Once opened the vaccine has a short shelflife of only one month and needs refrigeration. BVDV vaccine Bovilis BVD (Merck) is available in the UK and comprises of inactivated BVDV antigen of strain C-86. It protects the foetus against transplacental infection with BVDV and animals require an annual booster dose for protection. It has a shelf life of 18 months at +2° C. to +8° C. Once opened the vaccine shelf life is reduced to 10 hours.

Subunit vaccines are comprised of highly purified recombinant antigens such as proteins and peptides, these vaccines are more stable and have better safety profiles compared to the conventional vaccines. However, subunit vaccines can have poor immunogenicity and are often unable to cross intestinal mucosal tissues due to degradation by metabolic enzymes. To improve the immunogenicity of subunit vaccines, adjuvants are often added to the formulation. Adjuvants are defined as compounds that are added to the vaccine formulations in order to enhance the activation of the dendritic cells (DC) and generate strong antigen specific immune responses.

The silica vesicles of the present invention are also suitable for use with DNA vaccines. While DNA vaccines are capable of eliciting a strong immune response and high specificity, they often suffer from low efficiency of transfection of cell in vivo. Due to their ability to efficiently penetrate cell walls by endocytosis and release a biologically active payload, the immunogenic compositions of the present invention may be used to develop effective DNA vaccines with high transfection efficiency.

QuilA saponin-based adjuvant is known to stimulate Th1 immune response and production of cytotoxic T-lymphocytes against antigens, making it ideal for use in subunit vaccines for infectious diseases and cancer immunotherapy. However, disadvantages like pain at the site of injection, severe local reactions and toxicity profile of these adjuvants make them unsuitable for human use.

Figure 18:
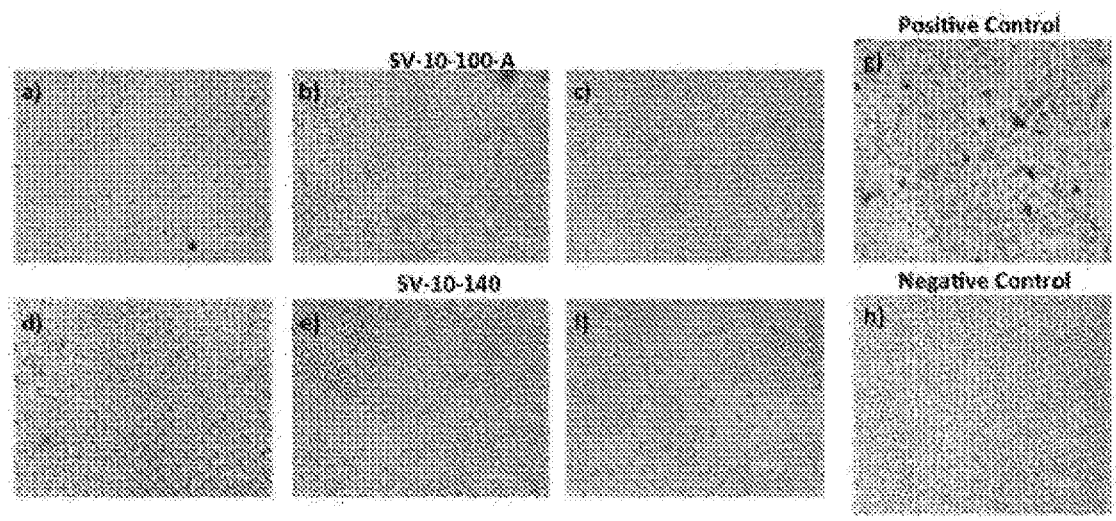
FIG. 18 is a series of images showing the results of a semi-quantitative assay to determine the cytotoxicity of hollow silica vesicles using trypan blue Staining (0.2%) of MDBK cells; (a) 0.5 mg/ml SV-10-x-100-A; (b) 0.1 mg/ml SV-10-x-100-A; (c) 0.01 mg/ml SV-10-x-100-A; (d) 0.5 mg/ml SV-10-x-140; (e) 0.1 mg/ml SV-10-x-140; (f) 0.01 mg/ml SV-10-x-140; (g) 0.5 mg/ml MCM-41 as synthesised vesicles (h) MDBK cells alone without silica vesicles.

In the experimental section the use of the present hollow silica vesicles SV-10-x-140 (being unmodified silica vesicles) and SV-10-x-100-A (being amino-modified silica vesicles) to test in vitro cytotoxicity to MDBK cells is set out as a prelude to testing their use as delivery agents in a nanovaccine formulation. In the cell culture study it was found that the amino functionalised SV-10-x-100-A at a concentration of 0.5 mg/ml was toxic compared to the unfunctionalised SV-10-x-140 (FIG. 18). However, at a lower concentration of 0.1 mg/ml and 0.01 mg/ml both SV-10-x-140 and SV-10-x-100-A were found to be of low toxicity. Hence, based on the in vitro cytotoxicity results, both SV-10-x-140 and SV-10-x-100-A were selected for further investigation. The concentration of the OptiE2 protein loaded SV-10-x-140 and SV-10-x-100-A was 200 µg protein/mg of silica vesicles after overnight adsorption as determined by protein assay. This represents an excellent level of loading of the antigenic component and is an advantageous feature of the present hollow silica vesicles.

The in vitro desorption studies on the OptiE2 loaded SVs at 37° C. in different buffers indicates that protein once bound to the present SVs does not dissociate easily which is further advantageous. OptiE2 protein did not dissociate when the experiment was performed with 0.1N HCL and citrate buffer pH 4.0, however, minimal desorption of the protein occurred in 0.1% SLS.

To determine the optimal characteristics required of unfunctionalised and amino functionalised vesicles such as pore size, surface area and functionalisation, both were investigated in an in vivo animal study. The treatment groups injected with OptiE2 (50 µg) loaded SV-10-x-140 (250 µg) and OptiE2 (50 µg) loaded SV-10-x-100-A (250 µg) immunogenic composition induced excellent antibody response, which was comparable to the positive control group administered with OptiE2 (50 µg) plus Quil A (10 µg). However, co-administration of traditional adjuvant Quil A did not enhance the total IgG titre and the IFN-γ response to OptiE2, as treatment groups injected with Quil A plus the HSV nanovaccine looked similar to the positive control group and the OptiE2 protein loaded HSV groups. Adjuvants act like immunostimulators or as antigen delivery vehicles, Quil A is known to initiate T-cell mediated immune response and the inventors have demonstrated that silica vesicles have the ability to induce both antibody and T-cell mediated responses. The assumption that co-administration of adjuvant and nanoparticles will elicit a strong immune response was based on the immunostimulatory effects and the 'depot effect' slow release of the antigen, where Quil A would potentiate the immune response and antigen loaded nanoparticles would act as delivery vehicles and immunostimulants. However, the results obtained from this experiment indicate that the co-administration of silica HSVs along with traditional adjuvant Quil A, did not induce a robust immune response.

This highlights the adjuvancy properties of the present silica vesicles as they act as excellent immunostimulators as well as antigen delivery vehicles, the groups administered protein plus SV nanoformulations induced a better IFN-γ response to OptiE2 epitope compared to the positive control group. Both antigen loaded SV-10-x-140 and SV-10-x-100-A elicited good antibody and cell-mediated immune responses. The mice remained healthy throughout the trial and there were no visible local responses at the injection sites. Addition of traditional adjuvant Quil A to the protein/nanoparticle formulation did not enhance the immune response. This showed that the SVs themselves act as excellent adjuvants and so present a number of advantages when employed as part of a nanovaccine or immunogenic composition.

The excellent binding properties, low toxicity, relatively high cellular uptake levels and pore wall structure result in a HSV which has highly advantageous properties as part of an immunogenic composition. These properties, in particular, the pore wall structure in combination with the large internal cavity of the HSVs make this delivery system especially suitable for the development and manufacture of single-dose vaccine products. More specifically, the large internal cavity of the HSVs allows a large amount of drug to be loaded into the HSVs and a larger than normal dose of drug to be delivered to a patient or subject. Since the pore wall structure of the HSVs provides for a limited rate of release of drug from the HSV, this large dose does not become bioavailable all at once, preventing an overdose from occurring. Rather, the drug is released slowly such that an immune response may be elicited over an extended period of time. In this way, drugs that are conventionally delivered using a multiple dose regimen (such as a prime-boost regimen) could, by using the HSVs in a formulation as described herein, be developed to be single-dose drugs. The conversion of a drug's dosing regimen from multiple dose to single dose has a number of advantages including lower administration costs and potentially higher compliance since the real world efficacy of some drugs delivered in multiple doses is limited by poor compliance to multiple dose regimens.

Further, vaccine immunogens/antigens, and proteins more generally, have long suffered from poor thermal stability, requiring refrigeration from the point of production through to use in the field (the "cold chain") to avoid degradation of the vaccine antigens or proteins and reduction in performance. A major goal in pharmaceutical research has been to improve thermal stability as this would greatly improve the usability and lower the cost of vaccines and protein therapeutics, particularly in remote areas such as on some farms and in developing countries. The present inventors have found that proteins which are contained within the silica vesicles of the present invention have significantly improved thermal stability such that the proteins, housed within the silica vesicles, may be exposed to temperatures well above room temperature without significantly denaturing the protein and affecting its biological activity. Exposure to elevated temperatures may be carried out while the silica vesicle/protein system is in a liquid carrier or in the form of a dried powder. The latter is possible since the protein-containing silica vesicles may be dried out and reconstituted (re-suspended) into a liquid carrier if desired.

The inventors have also found that encapsulating proteins within the silica vesicles of the present invention improves the resistance of the protein to breakdown by acids. This is a particularly useful feature for situations in which the silica vesicles may be used for the delivery of protein or other acid-sensitive molecules by the oral delivery route. Proteins are difficult to deliver by the oral route as they are typically broken down in the stomach due to the highly acidic environment, rendering them less pharmaceutically effective. The inventors have surprisingly found that protein contained within the silica vesicles is not significantly denatured by exposure to acidic conditions that simulate the environment of the stomach. As such, it may be feasible to use the silica vesicles in the development of oral dosage forms where acid-sensitive molecules such as proteins are desired to be delivered. Similar protection is also offered from trypsin and other digestive agents.

A sixth aspect of the invention resides in a method of eliciting an immune response in a subject including the step of administering a therapeutically effective amount of the immunogenic composition of the fifth aspect.

It will be appreciated that the immunogenic composition of the present invention is not limited in the type of disease that it is used to prevent (in the case of prophylactic vaccines) or treat (in the case of vaccines used for treatment). Examples of diseases that could be treated or prevented using the immunogenic composition of the present invention include, but are not limited to, Adenovirus Type 4 and Type 7, anthrax, tuberculosis, diphtheria and tetanus, pertussis, Hepatitis B, poliovirus, *haemophilus*, meningococcal disease, hepatitis A, human papillomavirus, influenza, Japanese encephalitis, measles, mumps and rubella, pneumococcal disease, rabies, rotavirus, smallpox, typhoid, varicella and yellow fever.

The immune response may be a cell-mediated immune response or antibody immune response.

A seventh aspect of the invention resides in a method of preventing or treating a disease or condition in a subject including the step of administering a therapeutically effective amount of the immunogenic composition of the fifth aspect.

In one embodiment, the disease or condition may be bovine viral diarrhoea, bovine ephemeral fever, anaplasmosis, human papilloma virus (HPV), Hepatitis B virus and influenza and those diseases or conditions listed in relation to the fifth and sixth aspects, above.

As used herein, the terms "subject" or "individual" or "patient" may refer to any subject, particularly a vertebrate subject, and even more particularly a mammalian or fish subject, for whom therapy or prophylaxis is desired. Suitable vertebrate animals include, but are not restricted to, primates, avians, livestock animals (e.g., sheep, cows, horses, donkeys, pigs, fish), laboratory test animals (e.g., rabbits, mice, rats, guinea pigs, hamsters), companion animals (e.g., cats, dogs) and captive wild animals (e.g., foxes, deer, dingoes). A preferred subject is a livestock animal selected from the group consisting of a cow, sheep, pig, fish or goat.

An eighth aspect of the invention resides in the use of a silica vesicle of the second or third aspects and an immunogen in the manufacture of a medicament for the treatment of a disease or condition.

The disease or condition may be any one or more of those described above in relation to the fifth to seventh aspects of the invention.

A ninth aspect of the invention resides in the use of a silica vesicle of the second or third aspects as an adjuvant.

All components of the sixth, seventh, eighth and ninth aspects including the immunogen, silica vesicles, diseases or conditions for treatment and the like may be as previously described in any of the first to the fifth aspects.

As discussed above, it has been demonstrated experimentally that the silica vesicles synthesised by the method described herein act as excellent immunostimulators as well as antigen delivery vehicles. An improved IFN-γ response to the OptiE2 epitope has been shown in the presence of the SVs.

EXPERIMENTAL

Materials

Block copolymer $EO_{39}BO_{47}EO_{39}$, commercial name B50-6600, [EO is poly(ethylene oxide) and BO is poly(butylene oxide)] was purchased from Dow Company. Tetraethyl orthosilicate (TEOS, ≥98%), (3-aminopropyl)triethoxysilane (APTES) and fluorescein-5-isothiocyanate (FITC) were all purchased from Sigma-Aldrich. The other reagents were of analytical reagent grade.

Analysis

The morphologies of the HSVs were observed using a JEOL JSM 7800F field emission scanning electron microscope (FE-SEM) operated at 1.5 kV. For FE-SEM measurements samples were prepared by dispersing powdered samples in ethanol, after which they were dropped onto aluminium foil pieces and attached to conductive carbon film on SEM mounts.

Transmission electron microscopy (TEM) images were obtained with a JEOL 2100 and JEOL 1010 operated at 200 kV and 100 kV, respectively. For TEM measurements samples were prepared by dispersing powdered samples in ethanol on carbon film on a Cu grid and drying.

Nitrogen adsorption/desorption isotherms were measured at 77 K using a Micromeritics Tristar II system. The samples were degassed at 453 K overnight on a vacuum line. The pore volume and cavity size distribution curves were derived from the adsorption branches of the isotherms using the Broekhoff and de Boer (BdB) model. The Barrett-Joyner-Halanda (BJH) method was utilized to calculate the entrance size from the desorption branch, and the Brunauer-Emmett-Teller (BET) method was utilized to calculate the specific surface areas. The total pore volume was calculated from the amount adsorbed at a maximum relative pressure $(P/P_0)$ of 0.99.

Fourier transform infrared (FTIR) spectra were collected on a ThermoNicolet Nexus 6700 FTIR spectrometer equipped with a Diamond ATR (attenuated total reflection) crystal. For each spectrum, 32 scans were collected at a resolution of 4 $cm^{-1}$ over the range 400-4000 $cm^{-1}$.

Cryo-TEM and ATR-FTIR of the reaction mixtures were performed at different reaction times to enable real time monitoring of the formation of the silica vesicles. For Cryo-TEM sample preparation, one drop of reaction mixture was dropped onto the carbon film on Cu TEM grids, before and after adding TEOS to the buffer solution containing the block copolymer and subsequently samples were analysed at 15 and 24 hours. The TEM grids were treated with liquid nitrogen for 10 min then freeze dried for at least 2 days.

For the ATR-FTIR studies, a series of ATR-FTIR spectra were collected at different reaction times (3, 6, 9, 12, 15 and 24 h) after the addition of TEOS into the buffer solution in step 1. Each spectrum was obtained against a background measured using the same buffer solution with an equal amount of $Na_2SO_4$. A further two analyses were carried out for reaction mixture in step 2 which was being performed at 70° C. The analysis was carried out at 3 and 6 h, respectively.

Preparation of Hollow Silica Vesicles

Step 1: 0.5 g of $EO39B047EO_{39}$ was dissolved in 30 g of pH=4.7 NaAc-HAc buffer solution ([NaAc]=[HAc]=0.40 M) with the addition of 0.852 g of $Na_2SO_4$ (0.20 M) to form a homogenous solution under stirring at 10° C. To this solution 3.33 g of TEOS was added with continuous stirring for 24 h.

In order to investigate the influence of temperature in step 1, a second experiment was carried out at 20° C. with all other parameters kept the same.

Yet a further experiment was carried out to investigate the influence of stirring in step 1 with all other parameters kept the same but only 10 min of stirring followed by 24 h of the reaction mixture sitting under static conditions. The different phases of reaction mixture which appear without stirring will be separated into different containers to take forward to the next steps.

Step 2; In step 2, the reaction mixtures from step 1 were taken up to a moderate temperature (40, 50, 60 or 70° C. were all trialed in separate experiments) with continuous stirring for a further 24 h.

Step 3: Reaction mixtures from step 2 were separately exposed to a hydrothermal treatment (HT) at different temperatures. To achieve this the appropriate samples were removed from their reaction vessels and placed into autoclaves and hydrothermally treated at one of 100, 120, 130, 140, 150, 170 or 180° C. for a further 24 h, at a pressure of 1, 2, 2.5, 3.5, 5, 8 and 10 bar, respectively. After this treatment step the precipitates were filtered off, repeatedly washed with water to remove the added salts, and then dried in air (referred to herein as the 'as-synthesized sample'). The final product was obtained by calcination of the as-synthesized sample at 550° C. in air for 5 h. To indicate the viability of the hollow silica vesicles after step 2 a number of those samples had the precipitate filtered off, washed and calcined ready for analysis without having being subjected to step 3.

Amino- and FITC Modification of HSVs

In the HSV amino-modification process, 1.5 g of calcined SV-10-50 and SV-10-50-140 were added into separate flasks. 60 ml toluene was added into each flask and the reaction was stirred for 6 h before adding 1.0 ml APTES. After stirring at 110° C. for 12 h, the HSVs were washed extensively with toluene and ethanol before being dried in a fume-hood at room temperature. The amino-modified samples were denoted SV-10-50-A or SV-10-50-140-A, accordingly.

To modify the HSVs with FITC, free —$NH_2$ moieties were utilized for labelling with FITC. The functional group of FITC, thiocyanate, is highly aminoreactive. 20 mg of powdered SV-As i.e. amino-modified silica vesicles, were dispersed in 3 ml deionized water and mixed with 5 ml of an FITC ethanol solution (0.3 mg/ml). After stirring in the dark at room temperature for 6 h, the SVs were centrifuged and washed with ethanol three times until the supernatant became colorless. The FITC labelled SVs were used for confocal microscopy observations after use in SCC25 cell uptake experiments.

Hydrophobic Modification of HSVs

To achieve hydrophobic modification of the SVs, 48 mg calcined SV-10-50 and SV-10-50-140 were added separately to two 50 ml three-neck flasks. Each sample was taken up in 6 ml of toluene and the reactant mixtures were stirred for 6 h before adding 0.12 ml (2% v/v) of n-octadecyltrimethoxylsilane (n-ODMS). After stirring at 110° C. for 12 h, the hydrophobically modified SVs were extensively washed with toluene and ethanol before being dried in a fume-hood at room temperature. The hydrophobically modified SV products were denoted SV-10-50-C18 or SV-10-50-140-C18, accordingly.

Cell Culture and Uptake

SCC25 cells were maintained in Dulbecco's Modified Eagle Medium (DMEM) and supplemented with fetal calf serum (10%, Sigma, MO), L-glutamine (1%), penicillin (1%) and streptomycin (1%) in 5% $CO_2$ at 37° C. The medium was routinely changed on alternate days and the cells were separated by trypsinisation before reaching confluency. SCC25 cells were seeded on glass cover slip in a 6-well plate ($5 \times 10^5$ cells per well) and incubated for 24 h. After washing twice with PBS, the cells were incubated with 1 ug/ml FITC labelled SV-10-50 or SV-10-50-140 in 2 ml of the serum supplemented DMEM medium for 24 h. Subsequently, the cells were washed twice with PBS to remove the remaining SVs and dead cells. The cells were then fixed with 2 ml of 4% PFA solution for 30 min at 4° C., and their nuclei were stained with DAPI and mounted on glass slide. Finally, the cells were viewed under a confocal microscope (LSM Zeiss 710) and images were captured.

Loading of Cytochrome C and Staining 0.5 ml PBS solution containing 1 mg SV-10-50 or SV-10-50-140 after calcination or following amino-modification was mixed with 0.5 ml cytochrome c-PBS solution (2 mg/ml). After incubation at 25° C. for a range of different times (5, 15, 30 min, 1, 2, 3, 8 and 12 h), the mixtures were centrifuged. To evaluate the cytochrome c loading efficiency, the supernatant was collected and the residual cytochrome c content measured using a UV-2450 (UV-Vis spectrophotometer, Shimadzu) at a wavelength of 480 nm. The loading amount of cytochrome c can be calculated based on the original and residual cytochrome c concentrations and volumes. The cytochrome c loaded SVs were re-dispersed into 1 ml. One drop of this suspension can be dropped onto the carbon film on Cu TEM grids and dried in air. The TEM grids were then treated with the staining agent 5% uranyl acetate (UAT) in 50% ethanol solution at 60° C. for 6 min. The stained TEM grids were washed with deionized water and dried in air.

Loading of Ribonuclease A and Staining 0.5 ml of phosphate buffered saline (PBS) solution containing 1 mg of either SV-10-50-C18 or SV-10-50-140-C18 was prepared as a suspension using an ultrasonic bath. Each suspension was mixed with 0.5 ml of ribonuclease A (RNase A)-PBS solution (2 mg/ml). After shaking at 200 rpm in a 25° C. incubator for 18 h, the mixtures were centrifuged. To evaluate the RNase A loading efficiency, the supernatant was collected through a 200 nm filter and the residual RNase A content was measured using a UV-2450 (UV-Vis spectrophotometer, Shimadzu) at a wavelength of 277.5 nm. The loading amount of RNase A can be calculated based on the original and residual RNase A concentrations and volumes. The RNase A loaded SVs were re-dispersed into 1 ml. One drop of this suspension was dropped onto the carbon film on Cu TEM grids and dried in air. The TEM grids were then treated with the staining agent 5% uranyl acetate (UAT) in 50% ethanol solution at 60° C. for 6 min. The stained TEM grids were washed with deionized water and dried in air.

Cell Toxicity and RNase A Denaturation

SCC25 cells were seeded in a 96-well plate at a density of $2 \times 10^4$ cells per well and cultured in 5% $CO_2$ at 37° C. for 24 h. Then, free RNase A, SVs, RNase A loaded SVs and corresponding denatured samples were added to the cells in DMEM medium at an RNase A dosage of 4-16 µg/ml, and the cells were incubated in 5% $CO_2$ at 37° C. for 24 and 72 h. Subsequently, MTT reagent (10 µl/well volume from 5 mg/ml solution in PBS) was added to each well, shaken for 10 seconds and then incubated at 37° C. for 4 h. The precipitants were collected following centrifugation for the above cell toxicity experiments after the removal of the supernatant. Then DMSO (100 µl) was added to each well to dissolve the formazan crystals and the optical density (OD) was recorded at 570 nm using a microplate reader (SpectraMax M5, Bio-Strategy, Ltd). Cells incubated in the absence of SVs and RNase A were used as the control. All the experiments were performed in triplicate for each group.

Another series of control groups was prepared after heat and acid denaturation of RNase A, including both free RNase A and RNase A loaded SVs. In the denaturation process, 50 µl of HCl (0.01M, pH 2.0) solution was added in to 1 mg of free RNase A or 6-9 mg of SVs (loaded with 1 mg RNase A). The mixtures were incubated at 65° C. for 40 min, cooled and centrifuged. NaOH (0.01M) solution was added dropwise into the mixtures until the pH reached ~7, indicated by precise pH paper and used as a denatured RNase A group in the present experiment.

Hollow Silica Vesicles as Vaccine Delivery Systems
HSV Characteristics

The SVs used in the 'nanovaccine' experiments were both unmodified SV-10-x-140' and amino-modified 'SV-10-x-100-A' versions with the characteristics as shown in table 1 below.

TABLE 1

Characterisation of the SV-10-x-140 and SV-10-x-100-A

| SV-10-x-140 | SV-10-x-100-A |
|---|---|
| Nanoparticle size: 50 nm | Nanoparticle size: 50 nm |
| Nanoparticle surface area BET: 209 $m^2/g$ | Nanoparticle surface area BET: 431 $m^2/g$ |
| Nanoparticle BdB pore size: 63 | Nanoparticle BdB pore size: 48 |
| Pore entrance size: 18.4 | Pore entrance size: 5.9 |
| Pore volume: 0.72 $cm^3/g$ | Pore volume: 1.22 $cm^3/g$ |

Trypan Blue Staining for In Vitro Cytotoxicity Assay

Madin-Darby bovine kidney (MDBK) cells (ATCC) were seeded at 80-90% confluency onto glass coverslips in a 24 well plate and allowed to adhere overnight in a 37° C., 5% $CO_2$ incubator. To investigate the effect of nanoparticle concentration on the cells a dilution range (0.5 mg/ml, 0.1 mg/ml and 0.01 mg/ml) of SV-10-x-140 and SV-10-x-100-A particles in Earle's Minimum Essential Media (containing 5% foetal bovine serum (Life Technologies) were prepared and gently added drop wise to the adherent cells. The cells were incubated in the presence of unfunctionalised SV-10-x-140, SV-10-x-100-A and MCM-41 (commercially available mesoporous silica) as synthesised nanoparticles at 37° C., 5% $CO_2$ for 20 h. Media was carefully removed and the wells were gently washed three times with PBS to remove the SVs/nanoparticles. To determine cell viability 0.2% trypan blue stain (Life Technologies) was added for 2 minutes. Trypan blue stain was carefully removed and the wells were washed once with PBS. Cells were fixed in 4% paraformaldehyde (PFA) pH 7.4 for 15 minutes, and then washed three times with PBS. Coverslips were mounted with 5 µl of MOWIOL (Sigma). Cell viability was determined by imaging on a Zeiss HAL100 microscope under bright field.

OptiE2 Adsorption to SV and SV-A Nanoparticles

Adsorption reactions used 1.5 mg of SV-10-x-140 and SV-10-x-100-A particles with 300 µg of OptiE2 in sterile Tris buffer at 2.5 mg/ml in a 2 ml final volume. This particle-protein slurry was placed in a shaker at room temperature (RT), after 24 h a sample of particle-protein slurry (50 µl) was removed and centrifuged at 16.2 g for 1 minute. The amount of unbound OptiE2 protein was assessed by electrophoresis of the supernatants on SDS-PAGE gels.

Desorption Studies

The OptiE2 loaded SV-10-x-140 and SV-10-x-100-A nanoparticle pellets were resuspended in 1000 µl of PBS plus 0.1% SLS (sodium laureth sulfate), or 0.1N HCL or citrate buffer with pH 4.0 and the samples were left on shaker at room temperature for 120 min at 200 rpm. The supernatant was assessed for desorbed protein by electrophoresis on SDS-PAGE gels.

Protein Assay

The supernatant of the adsorbed samples were quantified by protein assay (BioRad DC kit) following the manufacturer's instructions.

Polyacryalamide Gel Electrophoresis (PAGE)

Silica vesicle/nanoparticle samples were resuspended in 15 µl of PBS and 5 µl SRB (SDS Reducing Buffer consisting of 62.5 mM Tris-HCl (pH 6.8), 117 mM DTT, 10% Glycerol, 2% SDS, 0.02% Bromophenol blue), incubated at 85° C. for 2 min then subjected to electrophoresis on 10% Tris-Glycine gels (Invitrogen). The gels were visualised by staining in 50% methanol, 10% acetic acid, 0.25% Coomassie Blue R250 for 30 min, followed by destaining in 30% methanol, 10% acetic acid for three 30 min washes.

Immunization Studies Conducted in Mice

C57BL/6J mice were purchased from and housed in the Biological Resource Facility, The University of Queensland, Brisbane, Australia under specific pathogen-free conditions. Eight week old female mice were housed in HEPA-filtered cages with 4 animals per group in an environmentally controlled area with a cycle of 12 hours of light and 12 hours of darkness. Food and water were given ad libitum. All procedures were approved by The University of Queensland Ethics Committee. Animals were closely monitored throughout the study. All the animals remained in good health for the duration of the study with no visible deleterious health effects. Pre-immunisation blood samples were collected by retro-orbital bleeds using heparin coated hematocrit tubes (Hirschmann Laborgeräte, Heilbronn, Germany). Pre-immunisation blood samples collected prior to the first immunisation were referred to as the preimmune (PI) samples. Table 2 below shows the different treatment groups in the study. Adsorption reactions were prepared aseptically as described above. QuilA (Superfos Biosector, Vedback, Denmark) was resuspended at 2 mg/ml in sterile injectable water (Pfizer, Brooklyn, USA). The injectable doses were administered into the tail base by four subcutaneous injections to investigate the difference between the immune responses produced by the OptiE2 loaded SV-10-x-140, OptiE2 loaded SV-10-x-140 µlus QuilA, OptiE2 loaded SV-10-x-100-A, and OptiE2 loaded SV-10-x-100-A plus QuilA. The positive control group of mice received 50 µg OptiE2 protein and 10 µg QuilA. The negative control group received injections of SV-10-x-140 and SV-10-x-100-A (250 µg) vesicles plus Quil A (10 µg). Dose volumes of 100 µl (in 0.9% saline, Pfizer) were administered by subcutaneous injection at the tail base using a sterile 27 gauge needle (Terumo, Tokyo, Japan). Three injections were administered at 2 week intervals to all the treatment groups except for the unimmunised group and mice were sacrificed 14 days after the final immunisation. The OptiE2-specific antibody responses were studied using the Enzyme-Linked ImmunoSorbent Assay (ELISA) assay and the cell-mediated response was studies using ELISOPT assay.

TABLE 2

Immunization groups in mice trial. All doses were administered at the tail base.

| Group | Prototype Vaccine | Injection Dose |
|---|---|---|
| 1 Positive control | OptiE2 + QuilA | OptiE2 (50 µg) + QuilA (10 µg) |
| 2 | OptiE2 (50 µg) bound SV-10-x-140 | OptiE2 (50 µg) + SV-10-x-140 (250 µg) |
| 3 | OptiE2 (50 µg) bound SV-10-x-140 + QuilA | OptiE2 (50 µg) + SV-10-x-140 (250 µg) + Quil A (10 µg) |
| 4 | OptiE2 (50 µg) bound SV-10-x-100-A | OptiE2 (50 µg) + SV-10-x-100-A (250 µg) |

TABLE 2-continued Immunization groups in mice trial. All doses were administered at the tail base.

| Group | Prototype Vaccine | Injection Dose |
|---|---|---|
| 5 | OptiE2 (50 µg) bound SV-10-x-100-A + Quil A (10 µg) | OptiE2 (50 µg) + SV-10-x-100-A (250 µg) + Quil A (10 µg) |
| 6 | SV-10-x-100-A + Quil A (10 µg) | SV-10-x-100-A (250 µg) + Quil A (10 µg) |
| 7 | SV-10-x-140 + Quil A (10 µg) | SV-10-x-140 (250 µg) + Quil A (10 µg) |
| 8 | Unimmunised | — |

ELISA Protocol

Detection of OptiE2-specific antibody responses: Enzyme-Linked ImmunoSorbent Assay (ELISA) for the detection of OptiE2-specific antibodies were performed by coating microtitre plates (96 well, Nunc, Maxisorb, Roskilde, Denmark) with OptiE2 antigen solution (2 ng pL-1, 50 pL) in PBS overnight at 4° C. The coating solution was removed and the plates were washed once with PBS-T (PBS (1×), Tween-20 (0.1%), Sigma-Aldrich) and blocked with Bovine Serum Albumin (BSA, 5%, Sigma-Aldrich) and skim milk (5%, Fonterra, Auckland, New Zealand) in PBS (200 pL) for 1 h with gentle shaking at RT. Plates were washed three times with PBS-T. Mouse sera samples were diluted from 1:100 to 1:6400 in PBS (50 pL) and each dilution was added to the wells of the blocked plates followed by incubation for 2 h at RT. To detect mouse antibodies HRP conjugated polyclonal sheep anti-mouse IgG antibodies (Chemicon Australia, Melbourne, VIC, Australia) diluted in PBS to 1:1000 were added to each well and incubated for 1 h at room temperature with gentle shaking. Plates were washed three times in PBS-T. TMB substrate (100 pL, Sigma-Aldrich) was added to each well and incubated for 15 min at room temperature; HCl (1N, 100 pL) was added to wells to stop the chromogenic reaction. The plates were read at 450 nm on a Labsystems Multiskan RC plate scanner.

Isolation of Murine Splenocytes and ELISPOT Assay

Spleens were aseptically removed following euthanasia and placed into ice cold DMEM media (5 mL) supplemented with fetal bovine serum (FBS, 10%), Hepes (20 mM, pH 7.3), sodium pyruvate (1 M), Glutamax (1 M), penicillin G, streptomycin, Fungizone (calculate final amounts of each). Spleens were gently disrupted and passed through a nylon mesh (100 mm, Becton Dickinson, Franklin Lakes, N.J.) using a syringe plunger. Cells were washed with DMEM (5 mL) and centrifuged (800 g, 5 min, 4° C.) and then resuspended in lysis buffer (NH$_4$Cl (0.15 M), KHCO$_3$ (10 mM), Na$_2$-EDTA (0.1 mM), 1 mL) for 5 min at room temperature. Repeat wash steps twice with DMEM (9 mL and 5 mL) each time. Cell pellets were resuspended in DMEM (2 mL) and cell numbers determined by staining with trypan blue (0.2%). Cells from each mouse spleen were seeded at 1.0-1.5×10$^5$ cells/well in triplicate into Polyvinylidene fluoride (PVDF) ELISPOT plates precoated with monoclonal interferon-g (IFN-γ) (Mabtech) capture antibody. Cells were incubated in complete DMEM medium at 37° C. and 5% CO$_2$ for 40 h in the presence or absence of OptiE2 antigen (1 mg/mL, SIINFEKL, Auspep, Parkville, VIC, Australia) or the polyclonal activator concavalin A (Con A, 1 mg/mL, Sigma Aldrich) as a positive control. IFN-γ ELISPOT assays were performed according to the manufacturer's specifications. The ELISPOT plates were read on an ELISPOT reader (Autoimmun Diagnostika, Strassburg, Germany).

Results

Characteristics of SVs

Figure 2:
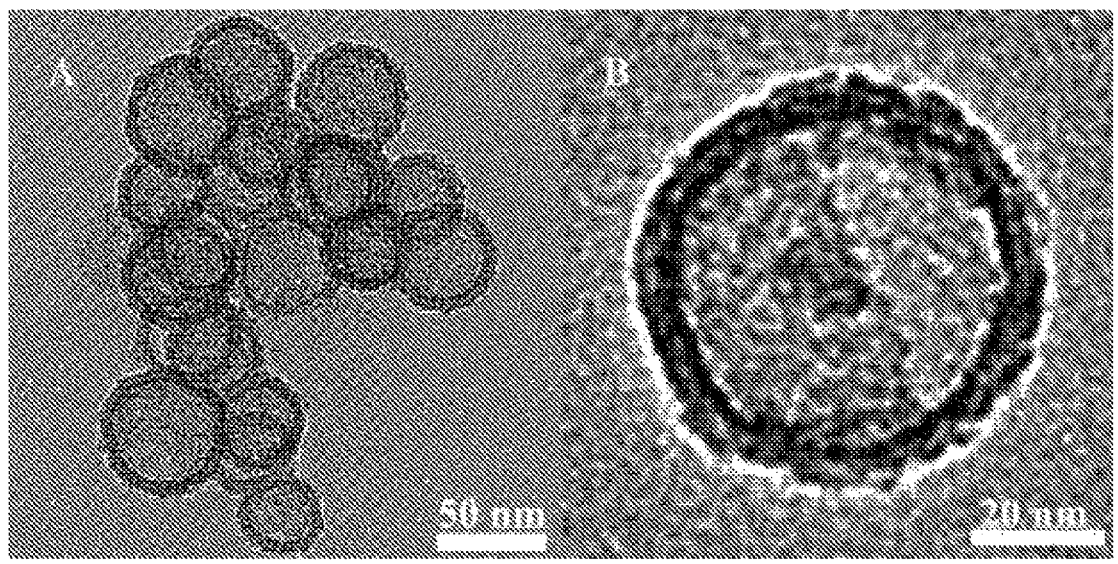
FIG. 2A-B shows a series of TEM images of as-synthesized SV-10-x-100 before calcinations.
Figure 4:
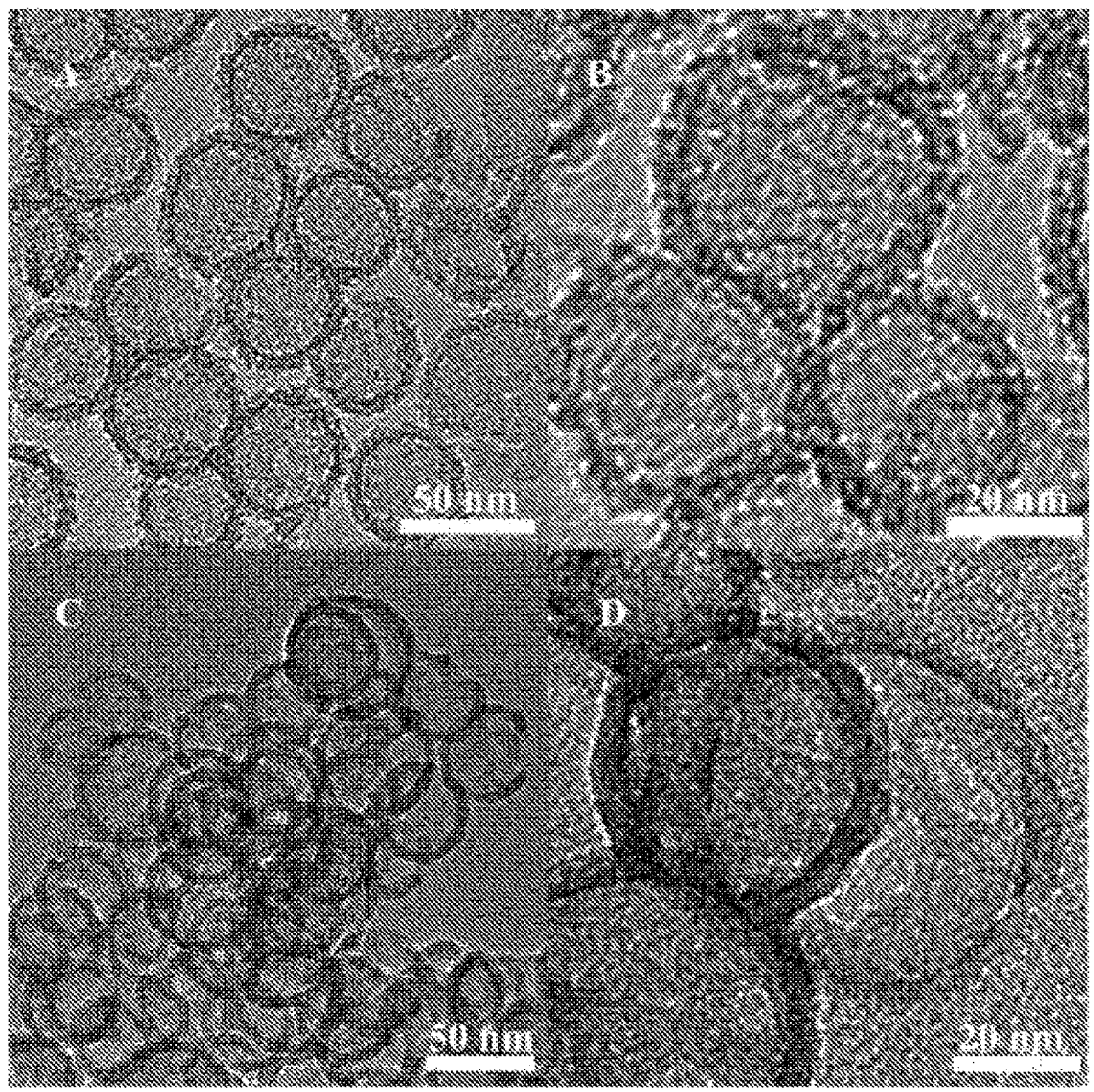
FIG. 4A-D shows a series of TEM images of (A, B) SV-10-50 and (C, D) SV-10-50-140 after calcinations.

FIG. 1 shows two field emission SEM images (A and B) showing that both SV-10-50 (image A) and SV-10-50-140 (image B) possess a spherical morphology with a uniform particle size under 100 nm. Looking to FIG. 2 the TEM images of as-synthesized SV-10-x-100 show unilamellar vesicles with a diameter of approximately 50 nm and a wall thickness of about 5 nm (FIG. 2A). From the higher magnification TEM image (FIG. 2B), it can be seen that a sandwich-like unilamellar structure of silica-void-silica is formed in the vesicle walls, indicating the existence of a silica-surfactant composite as represented in FIG. 3. After calcination, SV-10-50 maintains a unilamellar vesicle structure, as seen in FIG. 4A, and the spherical bodies can be clearly observed inside the vesicle walls indicating that the silica vesicles possess a porous wall structure which is made up of these spherical bodies, being bubble-like voids within the siliceous wall, which may be separate from one another or may be interconnected to form a pathway from the exterior to the interior cavity of the SV. This is best seen in FIG. 4B. SV-10-50-140 also maintains a unilamellar vesicle structure (FIG. 4C), and an entrance size of 15 nm can be observed on the wall as shown in FIG. 4D.

Figure 5:
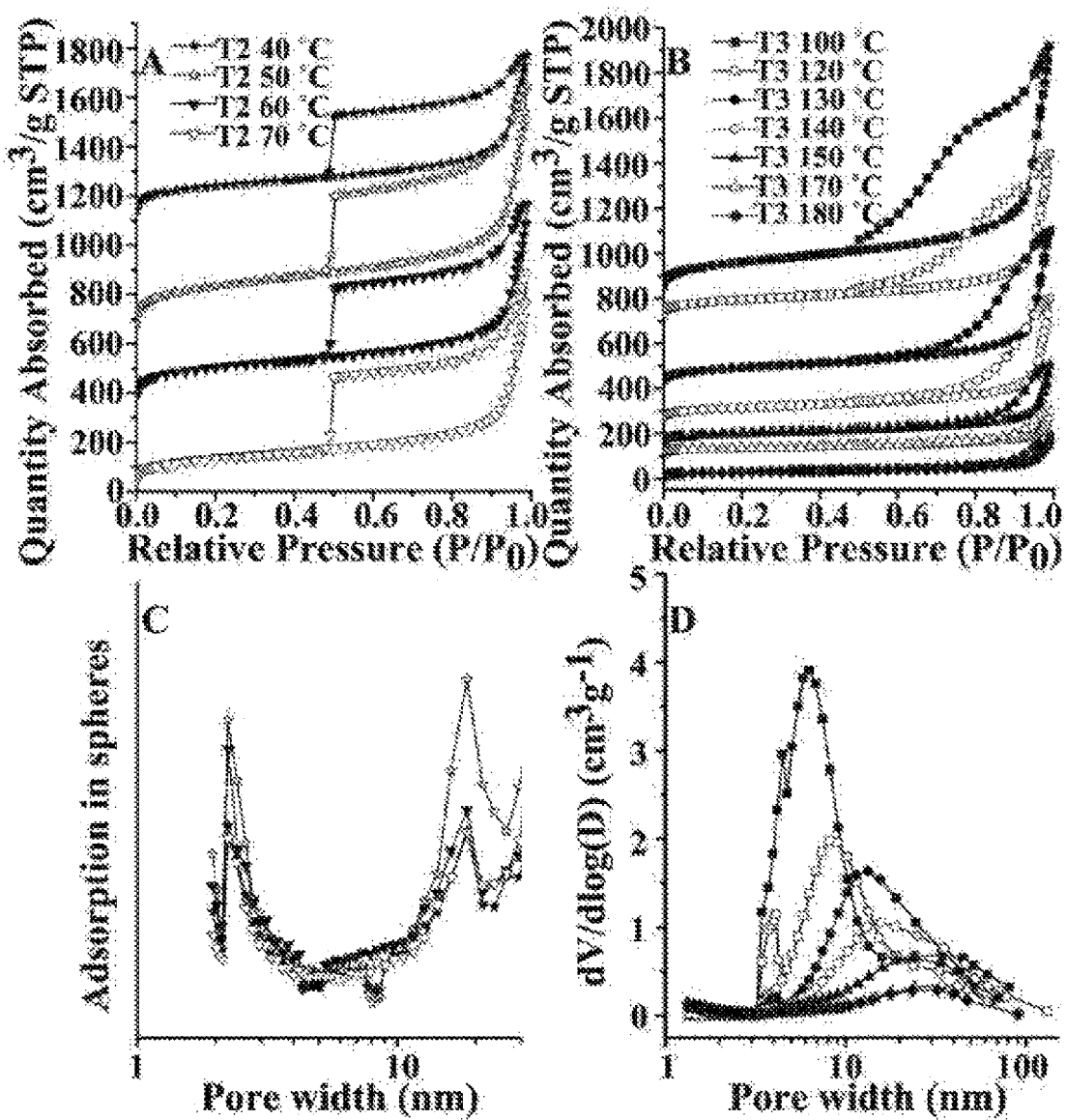
FIG. 5 shows nitrogen sorption isotherm plots of SV-10-T2 (A) and SV-10-x-T3 (B) after calcinations, pore size distribution plots calculated from $N_2$ sorption isotherms (C) BdB pore size distribution curves of SV-10-T2 from adsorption branch in the range of 1-30 nm, (D) BJH pore size distribution curves of SV-10-x-T3 from desorption branch.

The existence of a void in the silica vesicle walls is further confirmed by N$_2$ sorption analysis. FIG. 5A illustrates the nitrogen adsorption-desorption isotherms of SV samples at 40-70° C. heat treatment in step (b), which all show type IV isotherms with a type H2 hysteresis loop, indicating these four samples, having been exposed to an 'intermediate' temperature treatment in the second step, show similar pore structures. More structural information from the N$_2$ sorption results are shown in Table 1. FIG. 5B shows the nitrogen adsorption isotherms of SV samples which had been exposed to hydrothermal treatment temperatures of 120, 130, 140, 150, 170 and 180° C., at pressures of 2, 2.5, 3.5, 5, 8 and 10 bar, and these are seen to be typical type IV isotherms with desorption branch shifting to higher relative pressure as the hydrothermal treatment temperature increases. A BdB method is used to calculate the cavity size from the adsorption branch of nitrogen adsorption isotherms, and the entrance size is calculated using a BJH method from the desorption branch. The BdB pore size distribution curves in FIG. 5C show a peak centred at approximately 2 and 15 nm in SV samples with step (b) performed at 40-70° C., and for SV samples subjected to a hydrothermal treatment temperature of 100-180° C., at pressures of 1-10 bar, the BJH pore size distribution curves calculated from desorption branch, as seen in FIG. 5D, show peaks shifting to the right with increasing temperature, indicating increasing entrance sizes.

Figure 6:
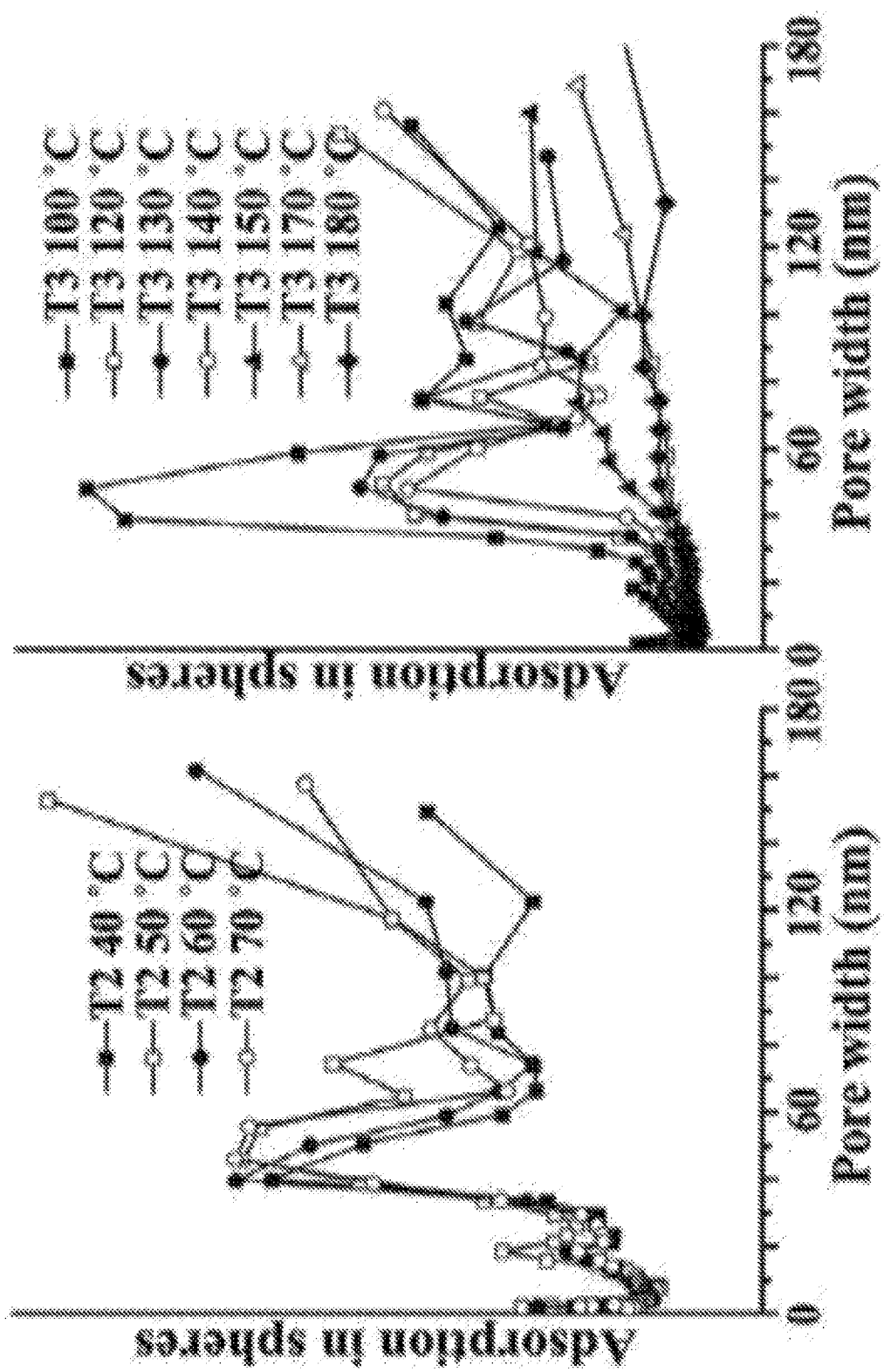
FIG. 6 is BdB pore size distribution from adsorption branch in the range of 1-180 nm of SV-10-T2 (A) and SV-10-x-T3 (B) after calcinations.

It is noted that all SV samples show a BdB calculated inner cavity size of 40-50 nm (FIG. 6), which indicates that all SV samples have similar cavity sizes within this range. As summarized in Table 3, below, the pore entrance size of the SVs could be adjusted in the range of 6-16 nm.

TABLE 3

Structural information from N$_2$ sorption results

| Sample Name | BdB Pore Size (nm) | Entrance Size (nm) | $V_p$ (cm$^3$g$^{-1}$) | $S_{BET}$ (m$^2$g$^{-1}$) |
|---|---|---|---|---|
| SV-10-40 | 40 | <3.9 | 1.117 | 630 |
| SV-10-50 | 40 | <3.9 | 1.158 | 645 |
| SV-10-60 | 40 | <3.9 | 1.340 | 670 |
| SV-10-70 | 46 | <3.9 | 1.238 | 590 |

TABLE 3-continued

Structural information from $N_2$ sorption results

| Sample Name | BdB Pore Size (nm) | Entrance Size (nm) | $V_P$ (cm³g⁻¹) | $S_{BET}$ (m²g⁻¹) |
|---|---|---|---|---|
| SV-10-x-100 | 48 | 6 | 1.729 | 549 |
| SV-10-x-120 | 50 | 8 | 1.141 | 321 |
| SV-10-x-130 | 48 | 13 | 0.946 | 312 |
| SV-10-x-140 | 62 | 16 | 0.934 | 209 |
| SV-10-x-150 | 74 | 24 | 0.544 | 175 | x: samples with direct hydrothermal treatment after continuous stirring at 10° C., $V_p$: total pore volume; $S_{BET}$: BET surface area.

Figure 7:
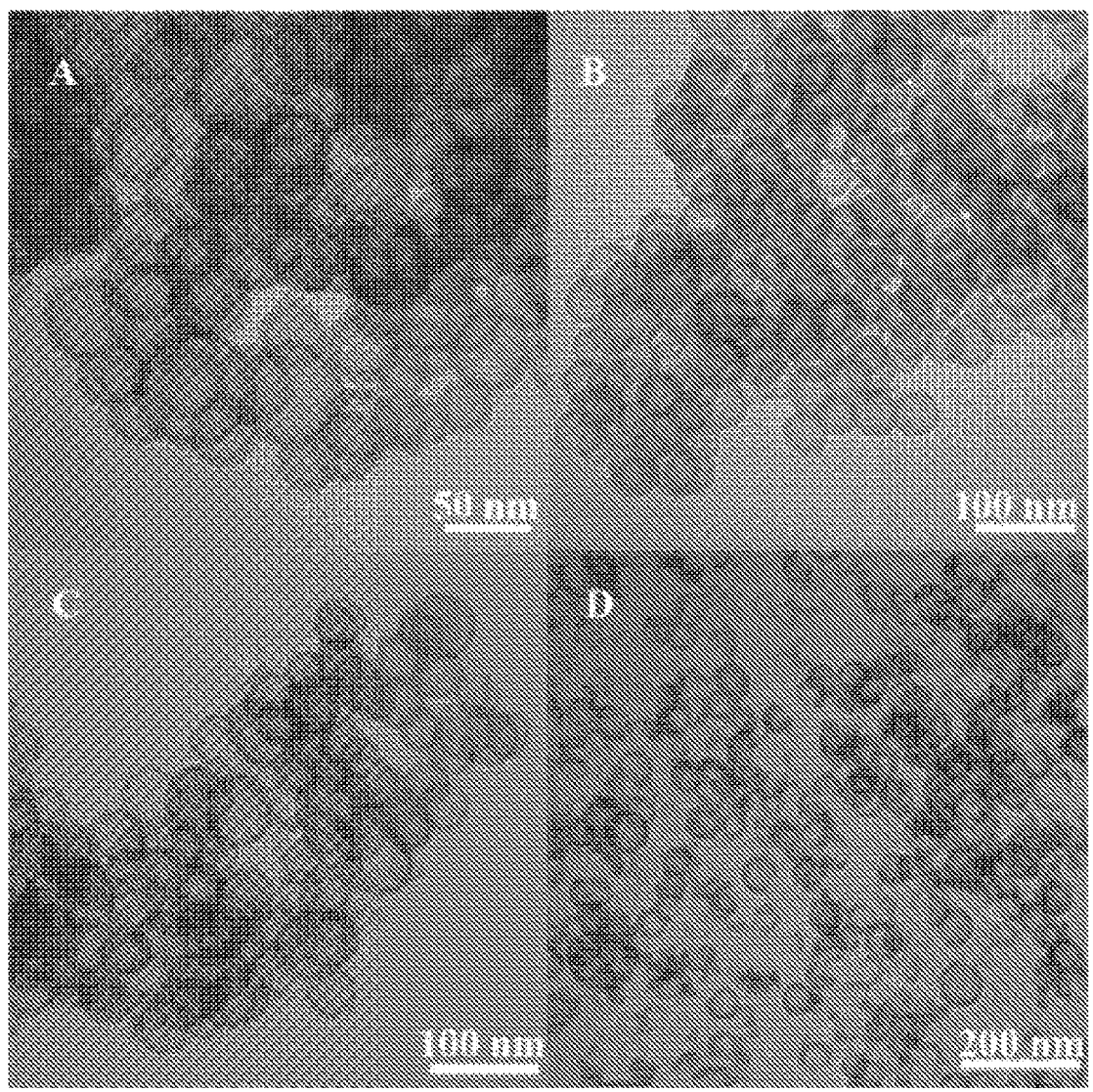
FIG. 7 is a series of TEM images of (A) SV-10-70, (B) SV-10-x-100, (C) SV-10-x-130, (D) SV-10-x-180 after calcinations, respectively.

TEM images of SV-10-70 after calcination (FIG. 7A) show similar vesicular structure with a pore wall structure in line with that already observed for SV-10-50. In contrast, no pore wall structure can be observed in the TEM images of SV-10-x-100, SV-10-x-130 and SV-x-180 after calcination (FIG. 7B-D) indicating the second step of treatment at moderate or intermediate temperature is essential for proper pore wall structure formation. Pore entrances with sizes of approximately 10 and 30 nm can also be observed (FIGS. 7C and D), respectively, which is in accordance with the $N_2$ sorption results.

In comparison, the TEM images of SV samples which were generated with only 10 min of stirring followed by 24 h static treatment show no vesicular structure. Instead short tubular structures and amorphous silica structures are observed as shown in FIGS. 8A and B, respectively. Compared to the uniform white reaction mixture achieved with continuous stirring, shown in FIG. 8C, the reaction mixture without continuous stirring separates into a transparent lower phase and white gel-like upper phase, shown in FIG. 8D. The TEM image of SV-20-x-100 shows a mixture of vesicular and tubular structures, FIG. 8E. It is clear from this result that some form of agitation is crucial for formation of the desired vesicular morphology.

Cryo-TEM and ATR-FTIR Observations

In order to understand the SV formation mechanism, Cryo-TEM was utilized to investigate the developing vesicle structure at different time points during step (a) (T1 in FIG. 3). As indicated in FIG. 9A, block copolymer B50-6600 surfactant is in micelle form with a diameter less than 20 nm, before addition of the silica source (TEOS). This shows no pre-formed vesicular template is used in the synthesis at 12 h (FIG. 9B), and the formation of SVs is a cooperative self-assembly of surfactant and silica oligomers. 15 h later after adding TEOS, self-assembled silica-surfactant vesicles can be observed (FIG. 9C), however, no pore wall structure can be observed at the end of step 1 (FIG. 9D). It is therefore apparent that the pore wall structure is formed only in a post treatment at moderate temperature.

Figure 10:
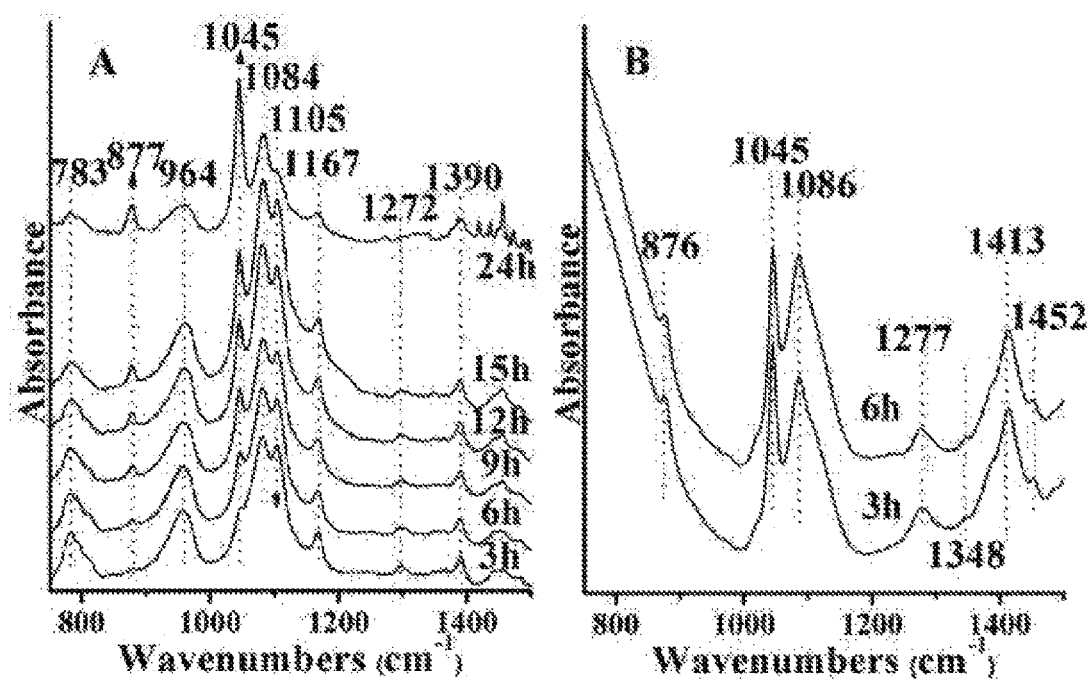
FIG. 10A is an ATR-FTIR spectra of the reaction mixture at 10° C. after adding TEOS in step (a)
FIG. 10B is an ATR-FTIR spectra of the precipitates in the subsequent 70° C. treatment in step (b), in the SV-10-70 reaction system as a function of time.

ATR-FTIR spectroscopy, in addition to the Cryo-TEM discussed above, was used to monitor the chemical species forming in the reaction mixtures. The ATR-FTIR spectra of reaction mixtures at different reaction times (3, 6, 9, 12, 15 and 24 h) in step (a) or T1, as denoted in FIG. 3, were measured. FIG. 10A shows three characteristic peaks appearing at 877, 1045 and 1272 cm⁻¹ which can be attributed to EtOH (ν(C—O)+ν(C—C)) and (ρ'(CH₃)+ρ(CH₂)), respectively. The weak and broad band observed at 964 cm⁻¹ is associated with the Si—O stretching of Si—OH groups. The vibration of Si—O—Si in condensed silica exhibits a broad peak in the region of 1050-1200 cm⁻¹, the assignment of which is complex. All the spectra from step one show the same characteristic bands at 783, 960 (ρ(CH₃)), 1084 (ν(C—O)/(C—O)+(C—C)), 1105 (ρ'(CH₃)), 1167 (ρ(CH₃)), 1272 (τ(CH₂)), 1396 (δs(CH₃)) cm⁻¹, which can be assigned to the —Si—OCH₂CH₃ groups.

The presence of —Si—OCH₂CH₃ groups throughout the 24 h reaction period in step (a) or T1, as denoted in FIG. 3, shows that the hydrolysis rate of TEOS is slow, which can be attributed to the steric effect of the alkoxy groups. The intensity of the bands at 878 and 1045 cm⁻¹ (both attributed to ethanol) increases slowly with the reaction time, indicating that the hydrolysis rate of TEOS is slow and the hydrolysis reaction of ethoxy groups continues in the time window in step (a) or T1. It is noted that the silanol groups derived from the hydrolysis of ethxoy groups should also exhibit a characteristic band at around 960 cm⁻¹ (Si—O stretching). However, considering the limited amount of ethanols released and thus a small amount of silanols generated, the peak for silanols can be overlapped with the band associated with SiOCH₂CH₃ and so may not be observed. Moreover, by comparing the characteristic peaks in the range of 1050-1200 cm⁻¹, no obvious broadening of bands in this region (which indicates the formation of —Si—O—Si) is observed in the TEOS system, i.e. the condensation rate of TEOS is also slow. As a result, the dominant siliceous species in step (a) or T1 are both partially hydrolyzed silanols and unreacted hydrophobic ethoxy groups. The hydrophobic silica oligomer in step (a) or T1 leads to a high g factor of silica/surfactant composite. The formation of vesicles is assumed to be from the bending and closure of a composite layer, which is similar to the formation of surfactant vesicles.

The ATR-FTIR spectra of the reaction products at 3 and 6 h in step (b) or T2, as denoted in FIG. 3, were also measured and are shown in FIG. 10B. All characteristic peaks (876, 1045, 1086, 1277, 1348, 1413 and 1452 cm⁻¹) can be attributed to EtOH (ν(C—O)+ν(C—C)) and (ρ'(CH₃)+ρ(CH₂)), respectively. No peak can be assigned to the —Si—OCH₂CH₃ groups, indicating TEOS has a much faster hydrolysis rate in this step and a low condensation rate at a moderate temperature from —Si—OCH₂CH₃ groups to silanol in step (b) within the silica vesicle-surfactant composites. This hydrophilic silica oligomer in step (b) leads to a lower g factor of silica/surfactant composite, which gives rise to high curvation change of the silica/surfactant composite without changing the vesicular skeleton to form a pore wall structure within the siliceous walls. The proposed formation mechanism of these silica vesicles is described in FIG. 3.

Loading of Cytochrome C and Staining

Figure 11:
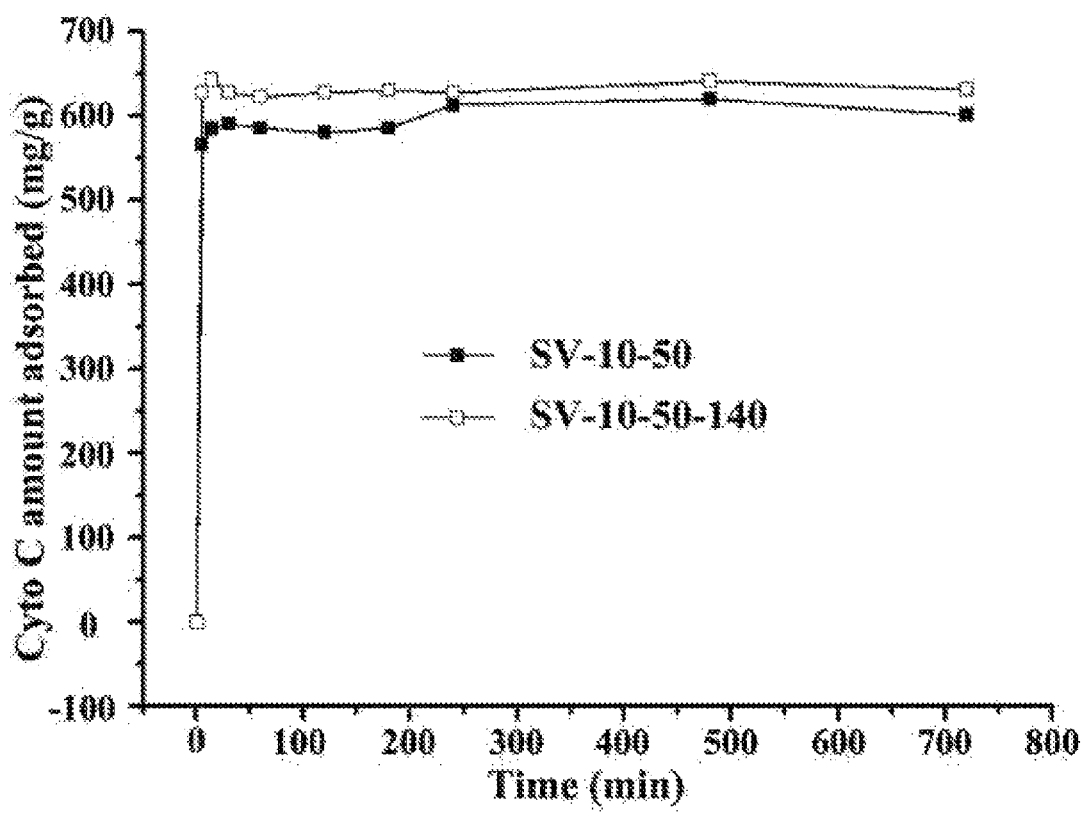
FIG. 11 is a graphical representation of the amount of adsorption of cytochrome c in the silica vesicles after calcination as a function of time (T=25° C.)

FIG. 11 shows high adsorption amounts of cytochrome c at 5 min in the hollow silica vesicles tested which indicates very fast adsorption for both SV-10-50 and SV-10-50-140 after calcinations. The adsorption level remains relatively steady after 5 min indicating the maximum adsorption amount has already been reached in this short space of time. The amount of loaded cytochrome c was 620, 642 mg/g for SV-10-50, SV-10-50-140, respectively.

Figure 12:
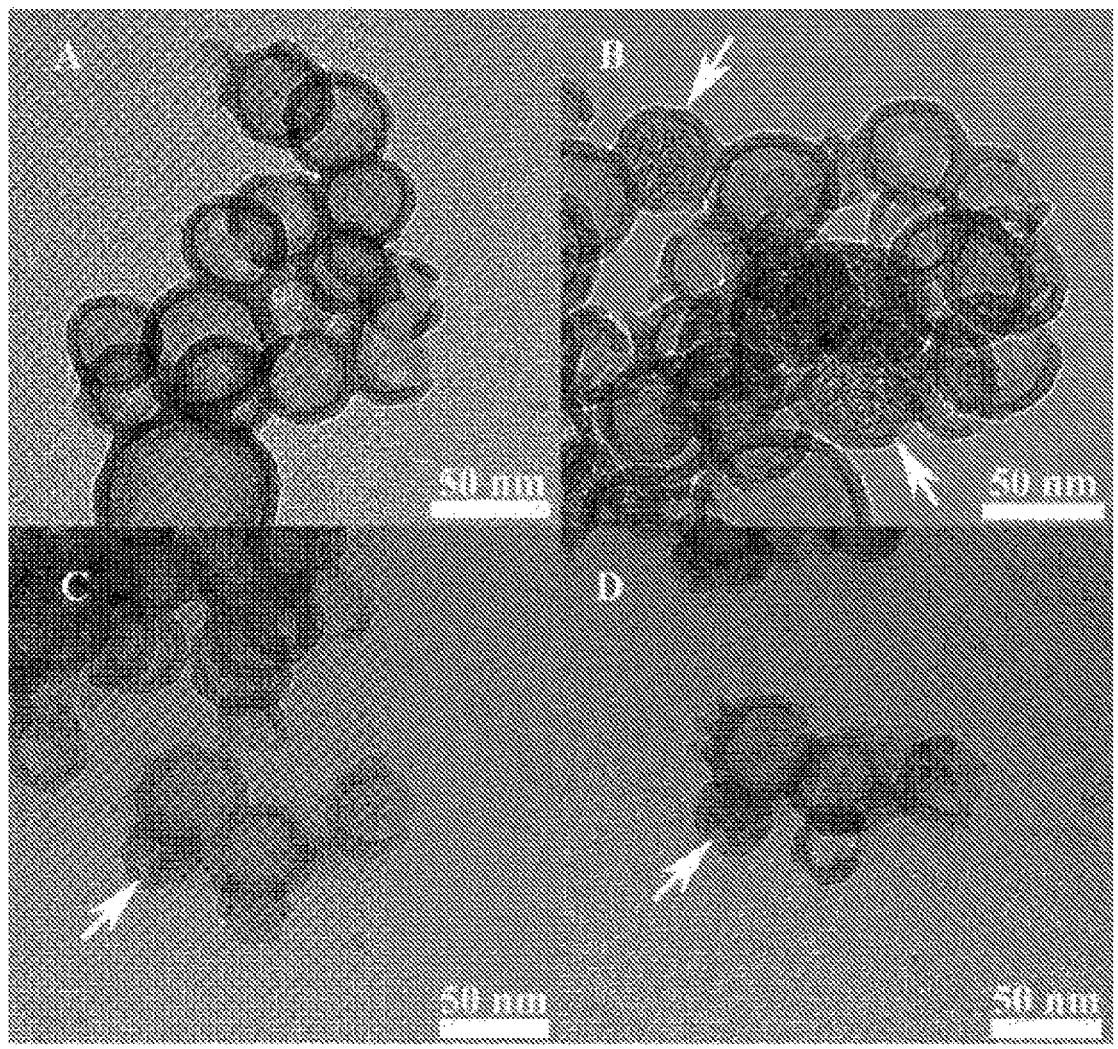
FIG. 12 is a series of TEM images of (A) pure SV-10-50-140 after calcination and (B-D) SV-10-50-140 loading of cytochrome c without tilting (B), with single tilting angle in x axis of +50° (C) and −50° (D), respectively.
Figure 13:
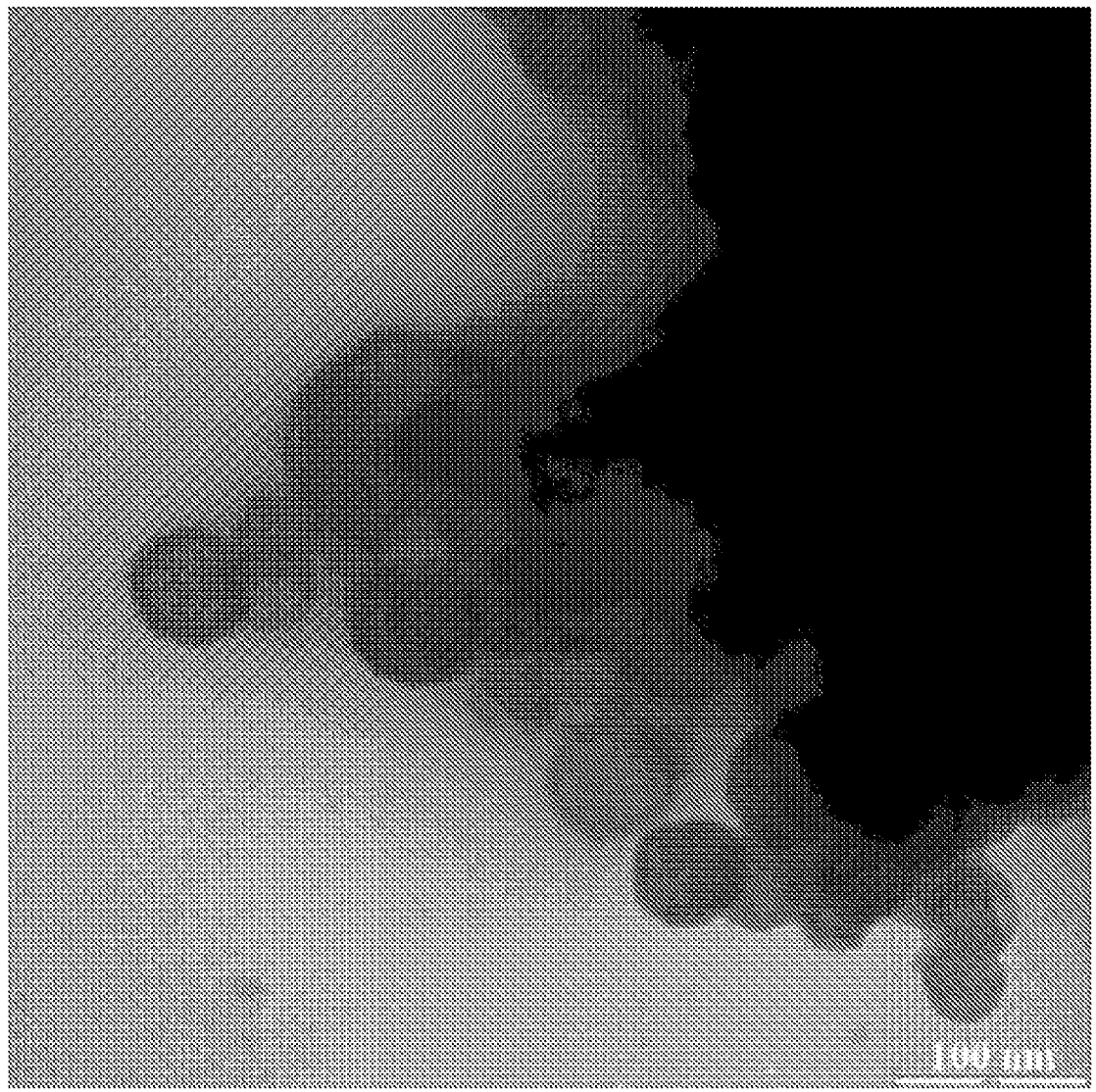
FIG. 13 is a TEM image of SV-10-50 loading of cytochrome c.

5% UAT in 50% ethanol solution was utilized as the staining agent for cytochrome c loaded in HSVs. The same staining method was applied to pure SV-10-50-140-C, i.e. after calcination, as a control, and the TEM image shown in FIG. 12A is similar to that of a HSV which has not been stained, indicating that the siliceous materials will not be stained by UAT. FIG. 12B shows several silica vesicles having a cavity with higher contrast (darker cavity, indicated by white arrows), which is stained cytochrome c. The high contrast of the cavity remains average with high tilting angles, as seen in FIGS. 12C and D, which indicate cytochrome c is uniformly adsorbed by the HSVs. This staining method has also been applied to SV-10-50 vesicles (FIG. 13).

Loading of Ribonuclease A and Staining

Figure 14:
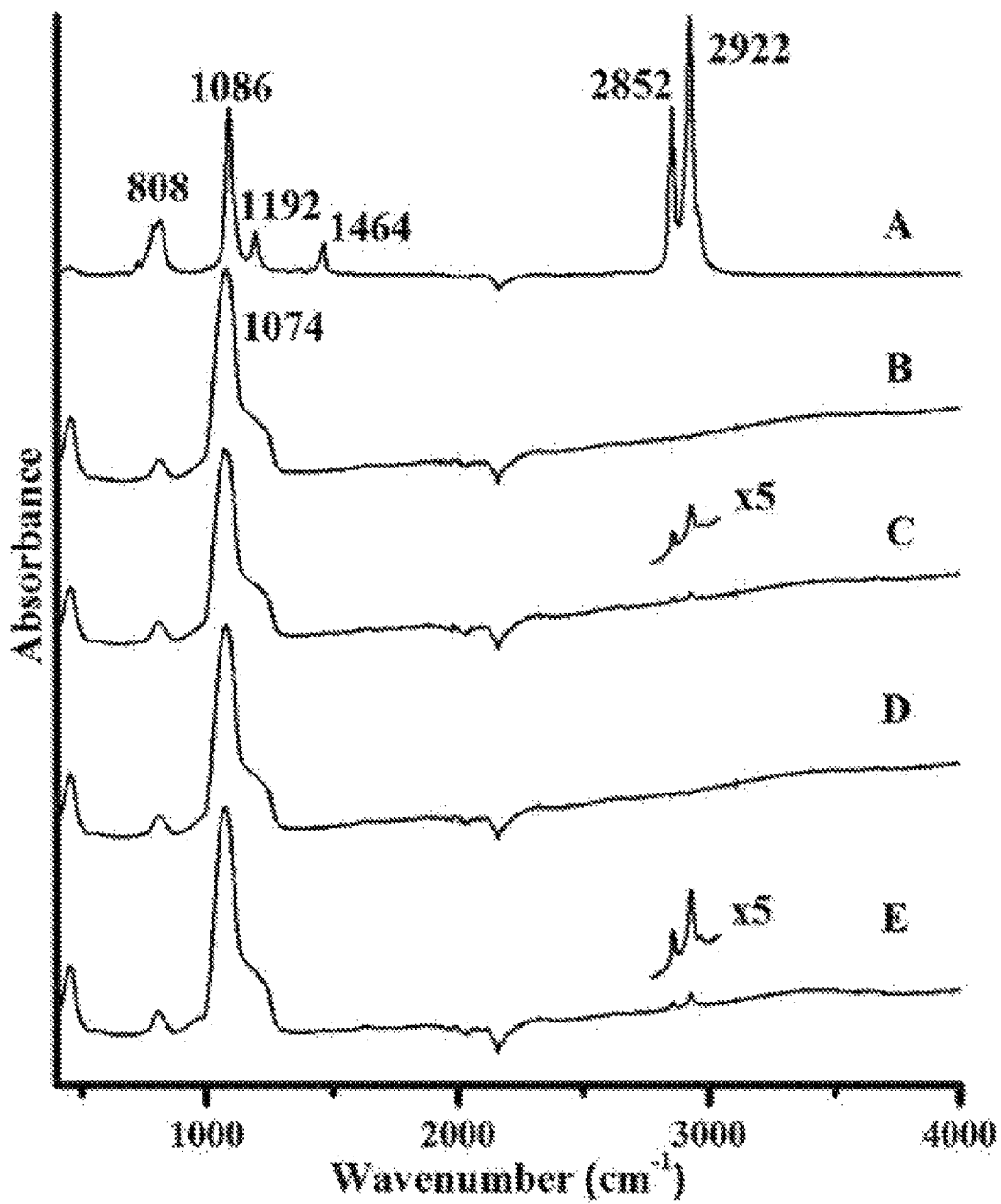
FIG. 14 is FTIR spectra of (A) pure liquid n-ODMS, (B and C) SV-10-50 and (D and E) SV-10-50-140 after calcinations (B and D) or after hydrophobic modification (C and E), respectively.
Figure 15:
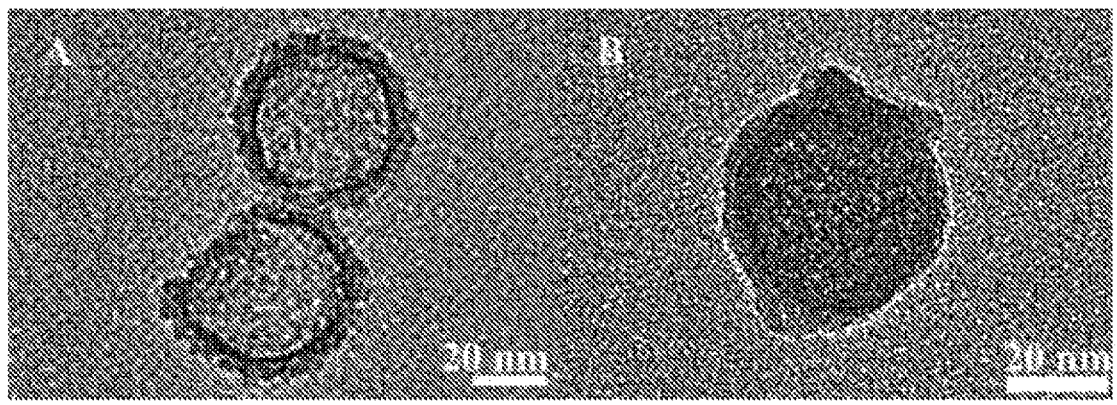
FIG. 15 is a series of TEM images of pure SV-10-50 after hydrophobic modification, before (A) and after (B) loading of ribonuclease A.

The FTIR spectra seen in FIG. 14 show the characteristic peaks of octadecyl groups on the vesicles after hydrophobic modification, indicating successful grafting of the hydrophobic groups onto the silica vesicles. The adsorption amount of RNase A for SV-10-50 and SV-10-50-140 after hydrophobic modification at 18 h is 206±6 and 276±8 mg/g, respectively. 5% UAT in 50% ethanol solution was utilized as the staining agent toward cytochrome c loaded in the SVs. The same method was applied to pure SV-10-50 after hydrophobic modification, and the TEM image (FIG. 15) is similar to that of the SV without staining, indicating the siliceous materials will not be stained by UAT. FIG. 15B shows a single silica vesicle possessing a cavity with higher contrast (darker cavity), which is considered to represent stained RNase A. RNase A has been shown to be uniformly adsorbed by the SVs.

Cell Culture and Uptake

Figure 16:
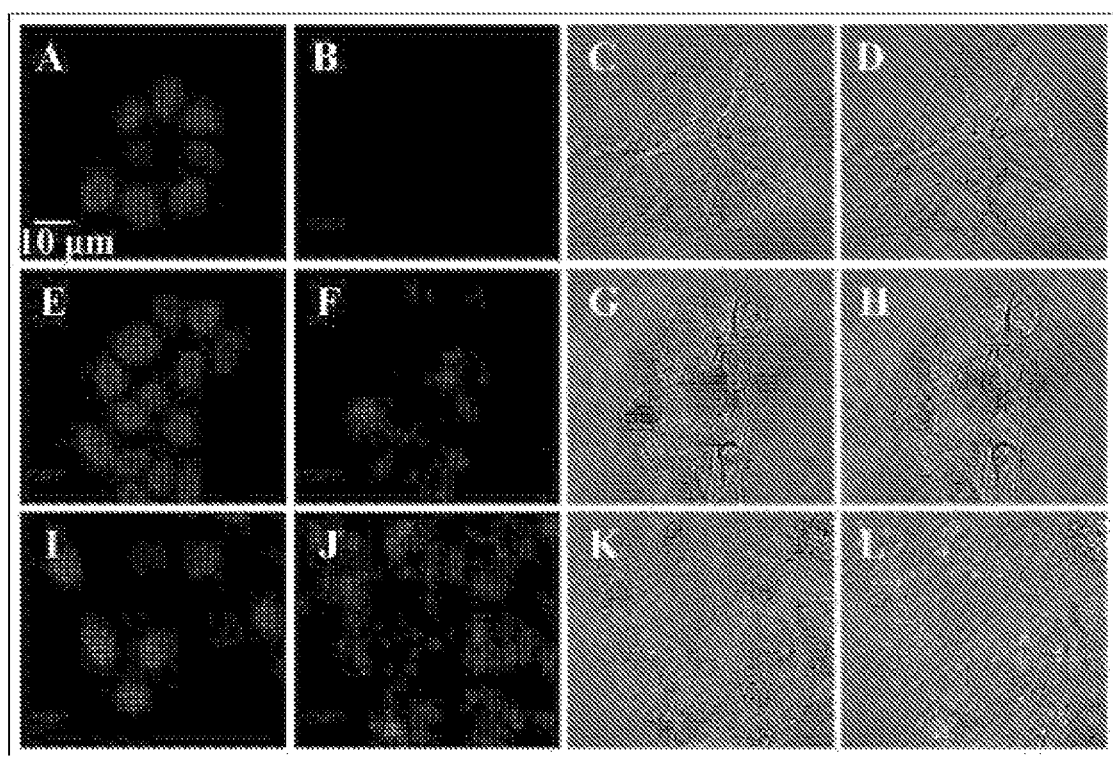
FIG. 16 is a series of confocal microscopy images of SCC25 cells which are either in a control group (A-D), have been treated with FITC labelled SV-10-50 (E-H) or with SV-10-50-140 (I-L) with 25 ug/ml in 24 h.

Silica vesicles which had been labelled with FITC, as described above, were studied by confocal microscopy to visualize the cellular uptake. As shown in FIG. 16, when the cells are incubated with FITC labelled SV-10-50 and SV-10-50-140, strong green fluorescent signals originating from FITC are detected inside the cells, indicating that the HSVs are readily taken up by SCC25 cancer cells (FIGS. 16H and L). FITC labelled SV-10-50-140 shows a stronger signal suggesting an increased amount of SV-10-50-140 internalized by SCC25 cells.

Cell Toxicity

RNase A is regarded as a strong protein synthesis disruptor which can degrade mRNA and tRNA to influence cell viability. It has been reported that heat-denaturation of RNase A reduced cell toxicity in MCF-7 cell lines where RNase A was conjugated on the outer surface of the dense silica nanoparticles. The anti-cancer effects of free RNase A, RNase A loaded SVs, SVs and corresponding denatured samples were investigated in human skin cancer SCC25 cells. Cells were treated with free RNase A, RNase A-SVs, denatured RNase A or denatured RNase A-SVs with the same concentration of RNase A. The SV concentrations were calculated from the adsorption amount of RNase A in SVs.

Figure 17:
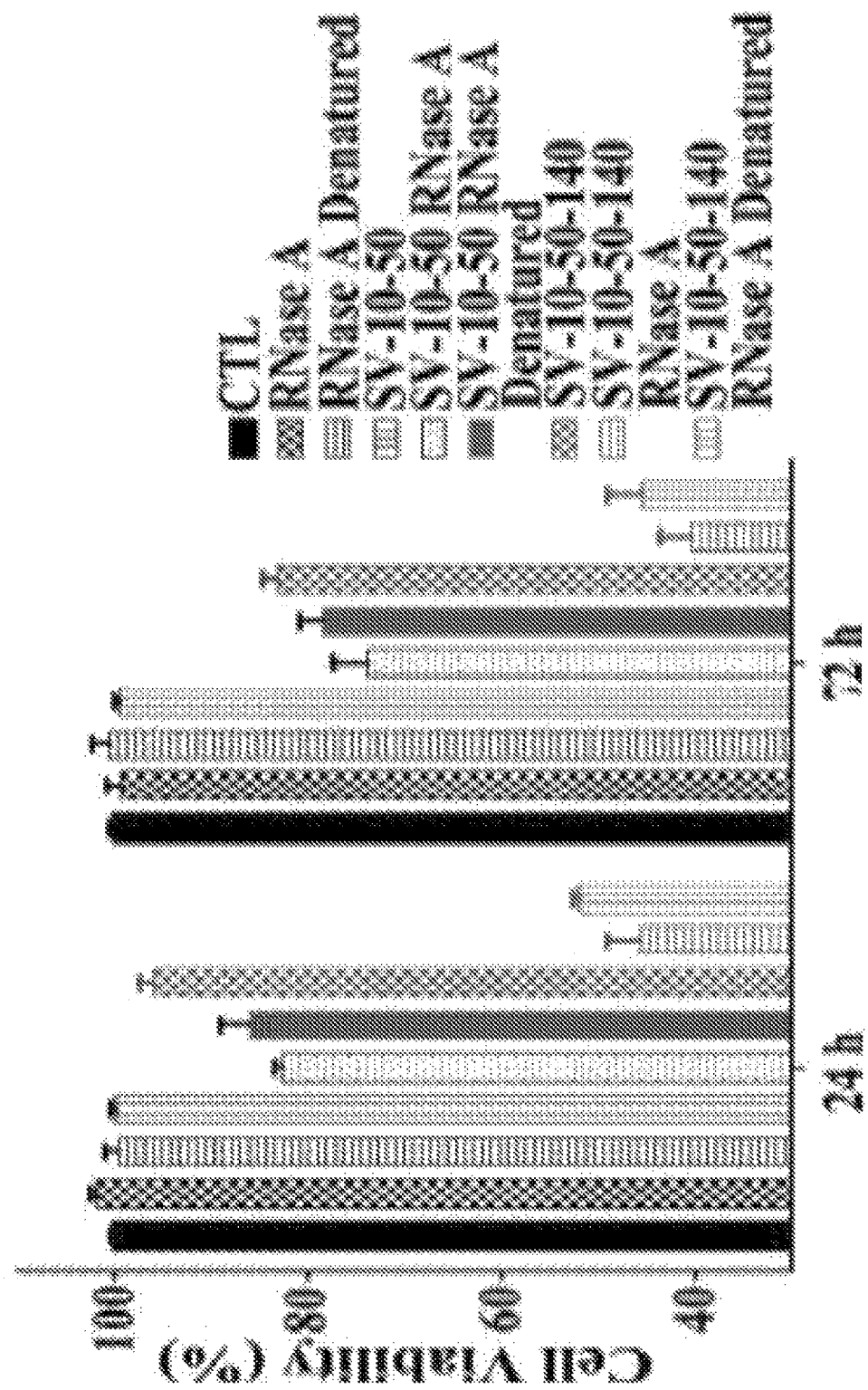
FIG. 17 is a graphical representation of cell viability in an SCC25 cell line with a ribonuclease A dosage of 16 µg at 24 h and 72 h.

The results in FIG. 17 reveal that both SV-10-50 and SV-10-50-140 showed almost no toxicity to SCC25 cells at 24 h at the concentration of 78 and 58 µg/ml, respectively. SV-10-50-140 shows low toxicity at 72 h (17% inhibition), indicating both SV species are biocompatible nano-carriers. Free RNase A and free RNase A after denaturation exhibit no cytotoxicity to SCC25 cells. Compared to free RNase A, RNase A loaded SV-10-50 and SV-10-50-140 after hydrophobic modification showed the highest cytotoxicity over a long time range (inhibition of 17%, 26% at 24 h and 54%, 43% at 72 h, respectively). Interestingly, RNase A loaded SVs after heat and strong acid denaturation showed high cytotoxicity to SCC25 cells compared to free RNase A with an inhibition of 14%, 22% at 24 h and 48%, 38% at 72 h for SV-10-50 and SV-10-140, respectively. RNase A-SVs after denaturation show slightly lower cell toxicity than RNase A-SVs without denaturation. These results demonstrate that the present SVs can provide protection to RNase A, which is proved to be adsorbed within the silica vesicles, from harsh conditions. RNase A loaded in SV-10-50-140 showed higher cytotoxicity due to its higher efficiency of cell internalization.

Vaccine Delivery System Related Results

In Vitro Cytotoxicity Studies

The in vitro cytotoxicity of the SV-10-x-140 and SV-10-x-100-A vesicles was determined by trypan blue dye exclusion staining of MDBK cells. The cells were treated with different concentrations (0.5, 0.1 and 0.01 mg/ml) of SV-10-x-140 and SV-10-x-100-A vesicles. Dead cells exhibited a blue colour due to the uptake of the dye via permeabilised cell membranes whereas viable cells remain intact and do not take up the stain. SV-10-x-140 and SV-10-x-100-A at 0.1 mg/ml and 0.01 mg/ml did not show any toxic effect on cell viability (FIG. 18, b, c, e and f). However, the SV-10-x-100-A at 0.5 mg/ml had a toxic effect on the MDBK cells (FIG. 18a) after 20 hours incubation. The cells incubated with lower concentrations of SV-10-x-140 and SV-10-x-100-A vesicles looked comparable to the cells incubated alone without vesicles, hence all further experimental investigations were carried out using both SV-10-x-140 and SV-10-x-100-A vesicles.

Adsorption and Desorption Analysis

OptiE2 protein was loaded onto the SV-10-x-140 and SV-10-x-100-A vesicles, as described above. The molecular weight of OptiE2 is 42 kDa. SDS-PAGE analysis was used to determine whether there was adsorption to the particles. Protein assays of the binding supernatants and application of a mass balance equation were used to determine the amount of OptiE2 adsorption to SV-10-x-140 and SV-10-x-100-A vesicles. 200 µg of OptiE2 bound to 1 mg of SV-10-x-140 and SV-10-x-100-A vesicles as determined by protein assay. Desorption studies were performed on the OptiE2 loaded SV-10-x-140 and SV-10-x-100-A.

To investigate the desorption the OptiE2 loaded vesicles pellets were resuspended in different buffers which included 0.1N HCL, 0.1% SLS and citrate buffer at pH 4.0. The samples were incubated at 37° C. on a shaker for 120 minutes. Gel analysis on the desorbed supernatant and particle fractions showed that in the presence of 0.1N HCL and citrate buffer pH 4.0, the protein remained strongly bound to the vesicles and it did not desorb from both SV-10-x-140 and SV-10-x-100-A (FIG. 19).

Figure 19:
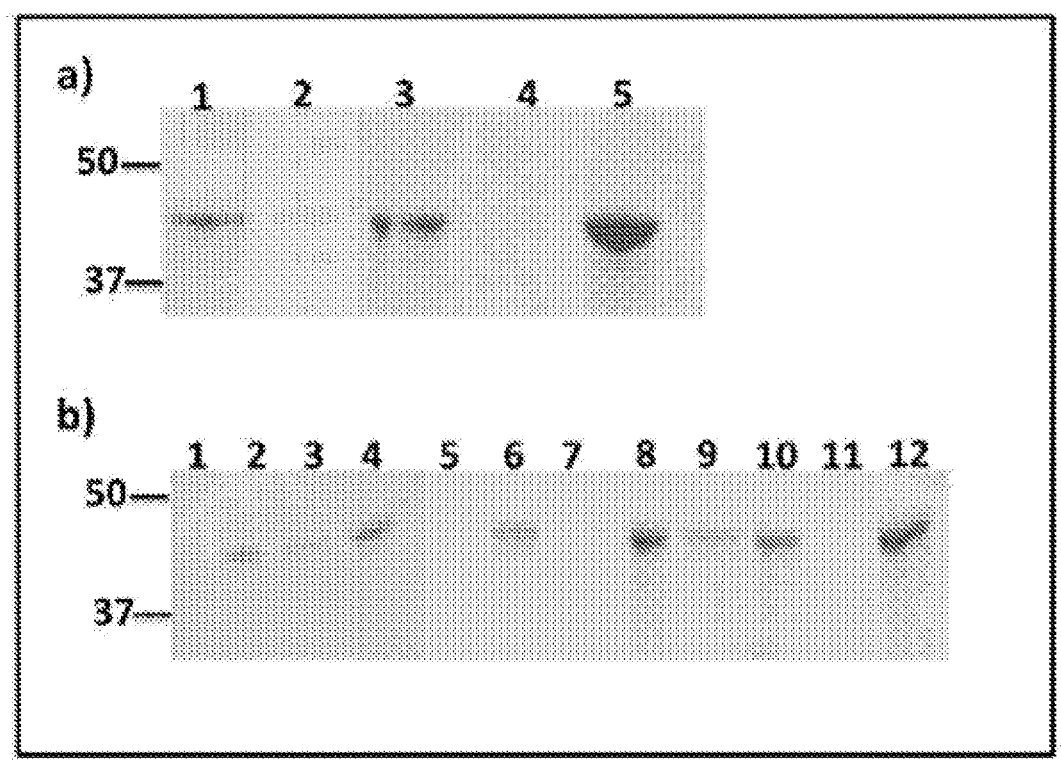
FIG. 19 is a gel analysis of the adsorption and desorption characteristics of the silica vesicles.
Figure 20:
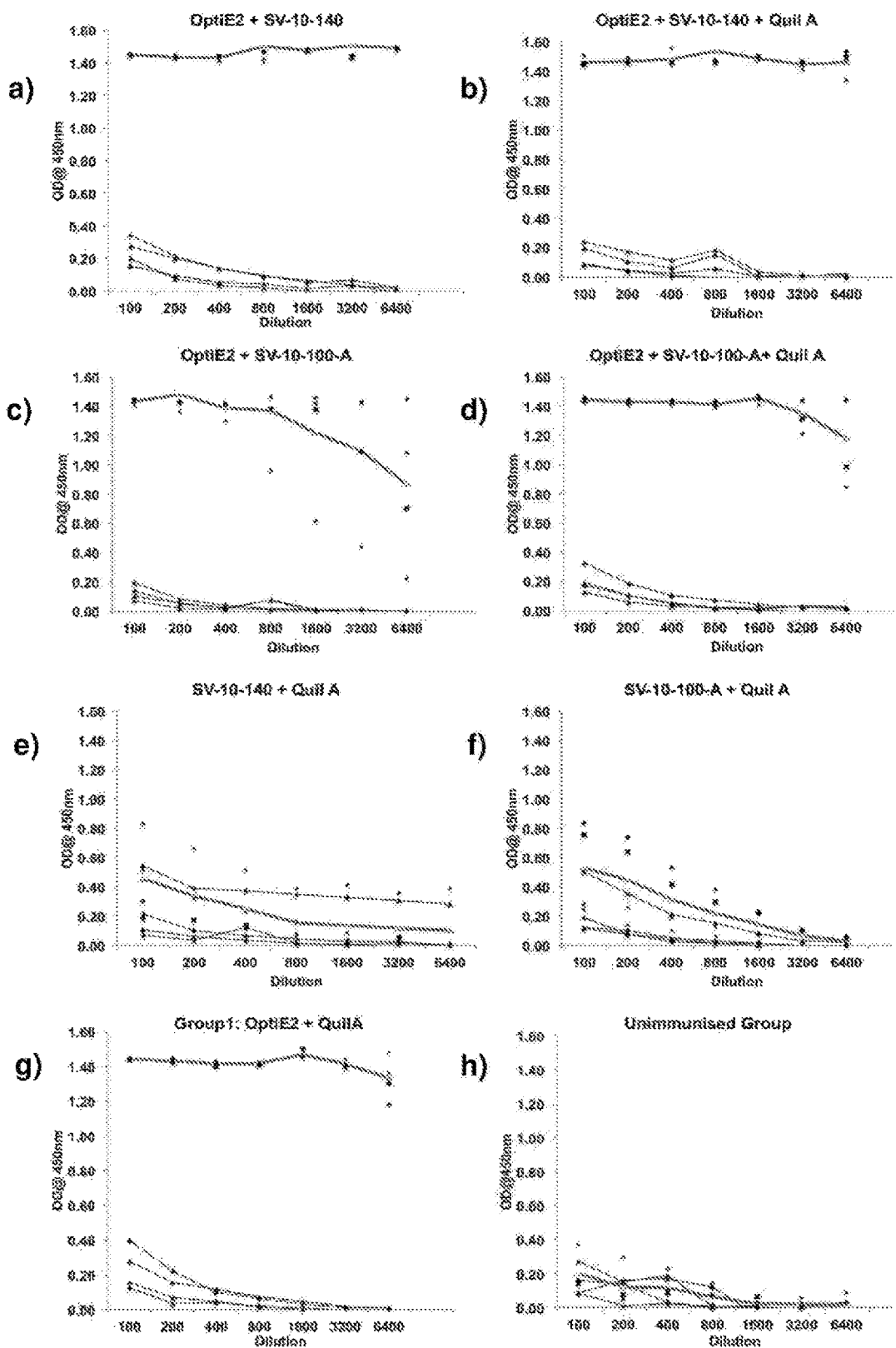
FIG. 20 is a graphical representation of the results of a series of ELISA assays indicating response of mice to injections of potential immunogenic compositions.
Figure 21:
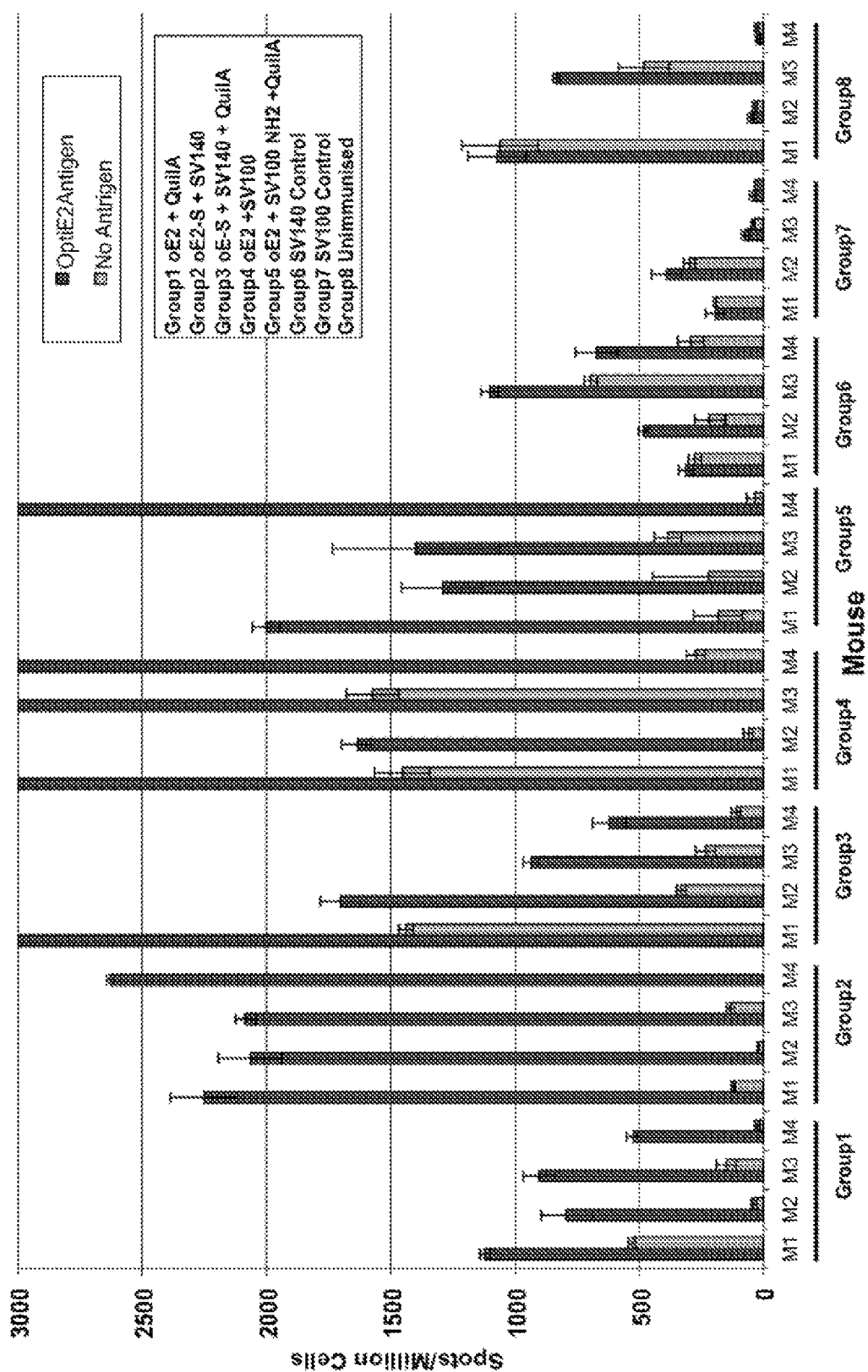
FIG. 21 is a graphical representation of the results of an ELISPOT assay of antigen specific IFN-γ secretion of murine splenocytes from immunised mice.

The details of the analytical results presented in FIG. 19 are as follows: (a) Evaluation of OptiE2 loaded nanoparticles, lane 1: OptiE2 protein; lane 2: OptiE2 loaded SV-10-x-100-A supernatant; lane 3: OptiE2 loaded SV-10-x-100-A nanoparticle pellet; lane 4: OptiE2 loaded SV-10-x-140 supernatant; lane 5: OptiE2 loaded SV-10-x-140 nanoparticle pellet (b) Desorption studies of OptiE2 loaded nanoparticles, lane 1: OptiE2 loaded SV-10-x-100-A supernatant desorbed in 0.1N HCL; lane 2: OptiE2 loaded SV-10-x-100-A nanoparticle pellet desorbed in 0.1N HCL; lane 3: OptiE2 loaded SV-10-x-100-A supernatant desorbed 0.1% SLS; lane 4: OptiE2 loaded SV-10-x-100-A nanoparticle pellet desorbed in 0.1% SLS; lane 5: OptiE2 loaded SV-10-x-100-A supernatant desorbed in citrate buffer (pH −4.0); lane 6: OptiE2 loaded SV-10-x-100-A nanoparticle pellet desorbed in citrate buffer (pH −4.0); lane 7: OptiE2 loaded SV-10-x-140 supernatant desorbed in 0.1N HCL; lane 8: OptiE2 loaded SV-10-x-140 nanoparticle pellet desorbed in 0.1N HCL; lane 9: OptiE2 loaded SV-10-x-140 supernatant desorbed 0.1% SLS; lane 10: OptiE2 loaded SV-10-x-140 nanoparticle pellet desorbed in 0.1% SLS; lane 11: OptiE2 loaded SV-10-x-140 supernatant desorbed in citrate buffer (pH −4.0); lane 12: OptiE2 loaded SV-10-x-140 nanoparticle pellet desorbed in citrate buffer (pH −4.0).

A very low amount of protein desorption from the vesicles was observed in the presence 0.1% SLS. The SV-10-x-140 and SV-10-x-100-A showcased similar adsorption and desorption characteristics. The SV-10-x-140 and SV-10-x-100-A have different pore sizes, therefore in order to investigate if the OptiE2 protein binds differently to these particles (internally or externally) and can have an effect on elicitation of immune responses when co-administered with a traditional adjuvant, Quil A, in vivo experiments were carried out with SV-10-x-140 and SV-10-x-100-A vesicles.

ELISA Data

Mice were immunised with vaccine formulations as described in Table 2. The total IgG responses of the immunised mice were analysed by anti-OptiE2-specific ELISA assays post three subcutaneous vaccine injections. The OptiE2 loaded HSV vaccine formulations were freshly prepared before the injection. PI sera samples from mice were collected at the start of the trial, and the subsequent sera samples were collected at two-week intervals following each injection over a 6 week period. All the mice remained in the normal weight range throughout the experiment. The ELISA result (FIG. 20) from the terminal bleeds suggest that the immunogenic composition treatment groups (OptiE2+SV-10-x-140, OptiE2+SV-10-x-140+Quil A, OptiE2+SV-10-x-100-A, OptiE2+SV-10-x-100-A+Quil A) and the positive control group (OptiE2+Quil A) showed an excellent antibody titre up to a dilution of 1:6400 with an average OD450 nm of 1.20. The treatment group administered with OptiE2 μlus HSV (SV) without any traditional adjuvant elicited an antibody response comparable to that seen for the positive control group. The group of mice injected with BVDV OptiE2 loaded unmodified or functionalised HSVs plus Quil A, showed almost similar responses. The co-administration of HSVs and traditional adjuvant did not result in a robust immune response, as the presence of Quil A in the vaccine formulation did not dramatically increase the response. Variation in the antibody response was observed between the four mice receiving OptiE2 μlus SV-10-x-100-A nanoformulation. The negative control groups receiving SV-10-x-140 and SV-10-x-100-A HSVs plus Quil A, showed a low background antibody response to OptiE2 epitope.

ELISPOT Assay

To determine the T cell mediated IFN-γ response to OptiE2 antigen an ELISPOT assay was used. Two weeks after the final immunisation, spleens from sacrificed mice were collected and harvested to obtain splenocyte cell populations. The mice receiving nanovaccine formulations OptiE2+SV-10-x-140, OptiE2+SV-10-x-140+Quil A, OptiE2+SV-10-x-100-A, and OptiE2+SV-10-x-100-A+Quil A showed excellent cell-mediated immune response to OptiE2 epitope. The results from the ELISPOT assay (FIG. 21 wherein M1 to M4 are the individual mice in each group and the black bars indicate the number of cells producing IFN-γ in response to the OptiE2 antigen) indicate that groups receiving antigen plus hollow silica vesicles looked more or less similar to the groups administered with antigen loaded HSVs plus traditional adjuvant. However, the groups receiving the nanovaccine formulations showed a better IFN-γ response compared to the positive control group (OptiE2+Quil A), highlighting the efficiency of silica vesicles as excellent adjuvants in their own right. In addition, the groups treated with antigen loaded HSVs elicited better T cell mediated response compared to the groups treated with antigen loaded HSVs plus traditional adjuvant. Co-administration of SVs plus traditional adjuvant did not increase the antibody response as well as the IFN-γ response significantly. The negative control groups, SV-10-x-140 μlus Quil A, SV-10-x-100-A plus Quil A and the immunised group produced an IFN-γ response. However, the response was not specific to the OptiE2 antigen as the unimmunised group too produced an IFN-γ response to the OptiE2 epitope.

Further Nanovaccine Experiments

The preceding experiments indicated clearly that the silica vesicles of the present invention with thin shell wall, large cavity and entrance size, improved OptiE2 protein adsorption and release. In addition, the OptiE2 (50 μg)/SV-140 (250 μg) formulation induced higher anti-OptiE2 IgG as well as IFN-γ responses compared to the positive control group OptiE2 (50 μg) plus Quil A (10 μg) and acted as self-adjuvants. While indicating commercially useful efficacy it was noted that to obtain a good level of antibody and cell-mediated immune responses the animals received administration of three nanovaccine injections. This success led the present inventors to develop an effective nanovaccine that could generate long-term immune responses using BVDV E2 as a model virus antigen.

General Discussion

Generally, the long term in vivo functionality of OptiE2 loaded silica vesicles (SV)-140 was tested in mice models by administering the positive control group with OptiE2 μlus Quil A (100 μg of OptiE2 μlus 10 μg of Quil A) and the nanovaccine treatment group with OptiE2/SV-140 (100 μg of OptiE2 adsorbed to 500 μg of SV-140). The mice were vaccinated with two injections and blood samples were collected at eight different time points for a period of six months to analyse the antibody responses. Spleens from the sacrificed mice, at two different time points post the final immunisation at 3 weeks (four mice) and 25 weeks (four mice), were collected to determine the IFN-γ response. The nanovaccine treatment group OptiE2/SV-140 generated BVDV specific antibody responses comparable to the conventional adjuvant Quil A at all the eight time points. In addition, at 25 weeks the cell-mediated response, which is essential to recognise and eliminate the invading pathogens, was higher [1500 spot forming units (SFU)/million cells] in all four mice immunised with OptiE2/SV-140 in comparison to OptiE2 μlus Quil A (473-1500 SFU/million cells). These experiments demonstrate the ability of SVs to induce long term humoral as well as cell mediated immune responses. Immunohistochemistry studies also showed higher response in mice injected with BVDV E2 SV formulation as compared to BVDV E2 Quil A. In addition, histopathology analyses was done on all the major organs of the animals at both 3 weeks and 25 weeks to make sure that they SV did not have a detrimental effect. All the animals used in the study remained healthy throughout the experimental period.

EXPERIMENTAL

Adsorption of OptiE2 on SV-140

Adsorption reactions used 2 mg of SV-140 with 500 μg of OptiE2 in sterile 50 mM Tris buffer (pH7.0) containing 0.2% Igepal CA630, in a 2 mL final volume. This particle-protein slurry was placed on a shaker at room temperature (RT) at 200 rpm. After 24 h a sample of particle-protein slurry (50 μL) was removed and centrifuged at 16.2 g for 1 minute. The amount of unbound OptiE2 protein was assessed by electrophoresis of the supernatants and the particles on SDS-PAGE gels.

Immunization Studies Conducted in Mice

C57BL/6J mice were purchased from and housed in the Biological Resource Facility, The University of Queensland, Brisbane, Australia under specific pathogen-free conditions. Eight week old female mice were housed in HEPA-filtered cages with eight animals per group in an environmentally controlled area with a cycle of 12 h of light and 12 h of darkness. Food and water were given ad libitum. Animals were closely monitored throughout the study. All the animals remained in good health for the duration of the study with no visible deleterious health effects.

Pre-immunisation blood samples were collected by retro-orbital bleeds using heparin coated hematocrit tubes (Hirschmann Laborgerate, Heilbronn, Germany). Pre-immunisation blood samples collected prior to the first immunisation were referred to as the pre-immune (PI) samples. Adsorption reactions were prepared aseptically as described above and the adsorbed OptiE2/SV pellet was washed in 1 mL of saline before preparing the final injectable doses. Quil A (Superfos Biosector, Vedback, Denmark) was resuspended at 2 mg/mL in sterile injectable water (Pfizer, Brooklyn, USA). The injectable doses were administered to investigate the difference between the immune responses produced by the OptiE2 plus Quil A, OptiE2/SV-140 and the unimmunised group. The positive control group of mice received 100 µg OptiE2 protein and 10 µg Quil A. The treatment group received injections of OptiE2 (100 µg) loaded SV-140 (500 µg) (Table 3 below). Dose volumes of 100 µL (in 0.9% saline, Pfizer) were administered by subcutaneous injection at the tail base using a sterile 27 gauge needle (Terumo, Tokyo, Japan). Two injections were administered at 3 week intervals to all the treatment groups except for the unimmunised group. Four mice from each group were sacrificed 21 days after the final immunisation. Blood samples from the remaining four mice were collected every 4 weeks for up to 25 weeks and at the end of the trial period animals were sacrificed. The animals were weighed and monitored for their health once a week. In addition, they were also observed for clinical signs and any signs of illness were converted to a numerical score as follows: 0=normal, 1-4=Moderate changes, animals need to be monitored daily, 5-10=Significant changes: monitor twice daily with the consultant the chief veterinary officer at the animal facility and >10=Euthanize.

TABLE 3

Immunisation groups in the further mice trial.
All doses were administered at the tail base.

| Group | Prototype Vaccine/Injection Dose |
|---|---|
| 1 | OptiE2 (100 µg) + QuilA (10 µg) |
| 2 | OptiE2 (100 µg)/SV-140 (500 µg) |
| 3 | Unimmunised |

Enzyme-Linked ImmunoSorbent Assay (ELISA) Protocol

Detection of OptiE2-specific antibody responses: ELISA for the detection of OptiE2-specific antibodies were performed by coating microtitre plates (96 well, Nunc, Maxisorb, Roskilde, Denmark) with OptiE2 antigen solution (2 ng/µL, 50 µL) in PBS overnight at 4° C. The coating solution was removed and the plates were washed once with PBS-T (1×PBS, 0.1% Tween-20, Sigma-Aldrich) and blocked with Bovine Serum Albumin (5%, Sigma-Aldrich) and skim milk (5%, Fonterra, Auckland, New Zealand) in 200 µL PBS for 1 h with gentle shaking at RT. Plates were washed three times with PBS-T.

Mouse sera samples were diluted from 1:100 to 1:6400 in 50 µL PBS and each dilution was added to the wells of the blocked plates followed by incubation for 2 h at RT. To detect mouse antibodies HRP conjugated polyclonal sheep anti-mouse IgG antibodies (Chemicon Australia, Melbourne, VIC, Australia) diluted in PBS to 1:50000 were added to each well and incubated for 1 h at RT with gentle shaking. Plates were washed three times in PBS-T. TMB substrate (100 µL, Life Technologies) was added to each well and incubated for 10 min at RT; 100 µL of 1N HCl was added to the wells to stop the chromogenic reaction. The plates were read at 450 nm on the BioTek microplate reader (Winooski, US).

Isolation of Murine Splenocytes and Enzyme-Linked Immunosorbent Spot (ELISPOT) Assay Spleens were aseptically removed following euthanasia from the four animals sacrificed at 3 weeks and the other four at 25 weeks after the final immunisation, the collected spleens were placed into 5 mL ice cold DMEM media (Life Technologies) supplemented with 10% foetal bovine serum (FBS, Life Technologies), 20 mM Hepes (pH 7.3), 1 M sodium pyruvate, 1 M Glutamax, 100 units/mL penicillin G, 100 µg/mL streptomycin, 0.25 µg/mL Fungizone. Spleens were gently disrupted and passed through a 100 µm nylon mesh (Becton Dickinson) using a syringe plunger. Cells were washed with 5 mL DMEM and centrifuged at 800 g for 5 min at 4° C. and then resuspended in 1 mL lysis buffer (0.15 M $NH_4Cl$, 10 mM $KHCO_3$, 0.1 mM $Na_2$-EDTA) for 5 min at RT. Repeat wash steps twice with DMEM (9 mL and 5 mL) each time. Cell pellets were resuspended in 2 mL DMEM and cell numbers determined by staining with 0.2% trypan blue. Cells from each mouse spleen were seeded at $1.0-1.5\times10^5$ cells/well in triplicate into Polyvinylidene fluoride (PVDF) ELISPOT plates precoated with monoclonal interferon-γ (IFN-γ) (Mabtech, Sweden) capture antibody. Cells were incubated in complete DMEM medium at 37° C. and 5% $CO_2$ for 40 h in the presence or absence of 1 µg/mL OptiE2 antigen or the polyclonal activator concavalin A (Con A, 1 µg/mL, Sigma Aldrich) as a positive control. IFN-γ ELISPOT assays were performed according to the manufacturer's specifications. The ELISPOT plates were read on an ELISPOT reader (Autoimmun Diagnostika, Strassburg, Germany).

Immunohistochemistry

Spleen sections were collected from the sacrificed mice at the time points 3 weeks and 25 weeks. A part of the spleen was dissected and frozen in OCT and 5 µm sections were cut using Hyrax C60 cryostat. The slides with cryosections were fixed in cold ethanol on ice for 8 min and then dried at RT for 20 min. The slides were then washed 3×5 min in PBS, left to dry at RT for 20 min and using a Dako pen circles were marked around the sections. The sections were then incubated overnight with the blocking buffer (1% BSA+5% FBS+PBS) at 4° C. Next day, to remove the block the slides were washed 3×5 min in PBS. The sections were then incubated with Alexa Fluor 488 Goat Anti-Mouse IgG at 1:500 for 1 h at RT in dark, the slides were then washed 3×5 min in PBS. To stain the nucleus the sections were then incubated with DAPI for 5 min and quickly washed in PBS. The sections were mounted with ProLong® Gold Antifade mounting medium and examined under microscope.

Histopathology

Heart, kidney, liver and injection sites from the sacrificed mice were collected and fixed in 10% formalin for 48 h. The organs were further processed and embedded in paraffin and 8 µm sections were cut using the Leica RM 2245 Rotary Microtome. The sections were then stained using the following haematoxylin and eosin staining procedure. Sections were first Dewaxed in xylene (3 changes of 2 min each), and then rehydrated in absolute alcohol (2 changes of 2 min each), in 90% for 2 min, in 70% for 2 min. Then washed in running tap water for 2 min and stained in haematoxylin for 3 min and again washed in running tap water for 2 min. Sections were then washed in 70% alcohol for 2 min and stained in eosin for 3 min. Sections were then washed in 95% alcohol for 2 min, then in absolute alcohol (3 changes of 2 min each). Finally, the sections were rapidly dehydrated and fixed in xylene (3 changes of 2 min each) and mounted in DePeX. The sections were then observed under microscope.

Results
Adsorption

Figure 22:
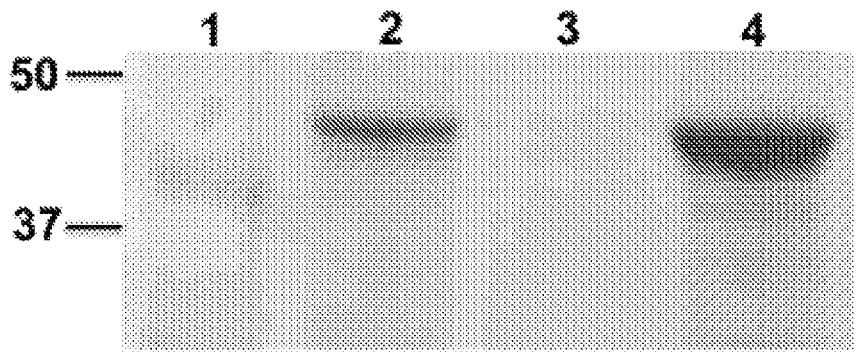
FIG. 22 is an image of an SDS-PAGE gel showing adsorption of oE2 on SV-140; Lane 1—marker, lane 2—oE2 protein, lane 3—oE2/SV-140 supernatant, lane 4—oE2/SV-140 pellet.

Adsorption tests were conducted by incubating 500 µg of OptiE2 protein with 2 mg of SV-140 for 24 h. The molecular weight of the expressed OptiE2 (referred to hereinafter as OptiE2 or oE2 which terms are used interchangeably) is 42 kDa. The protein and particle slurry was collected and separated into supernatant and particle samples and analysed by SDS-PAGE to determine the adsorption of protein. The gel analysis indicates that after 24 h of binding no protein was detected in the supernatant (FIG. 22-lane 3) and complete binding of OptiE2 to SV-140 was observed in the particle pellet (FIG. 22-lane 4).

ELISA Data

Figure 23:
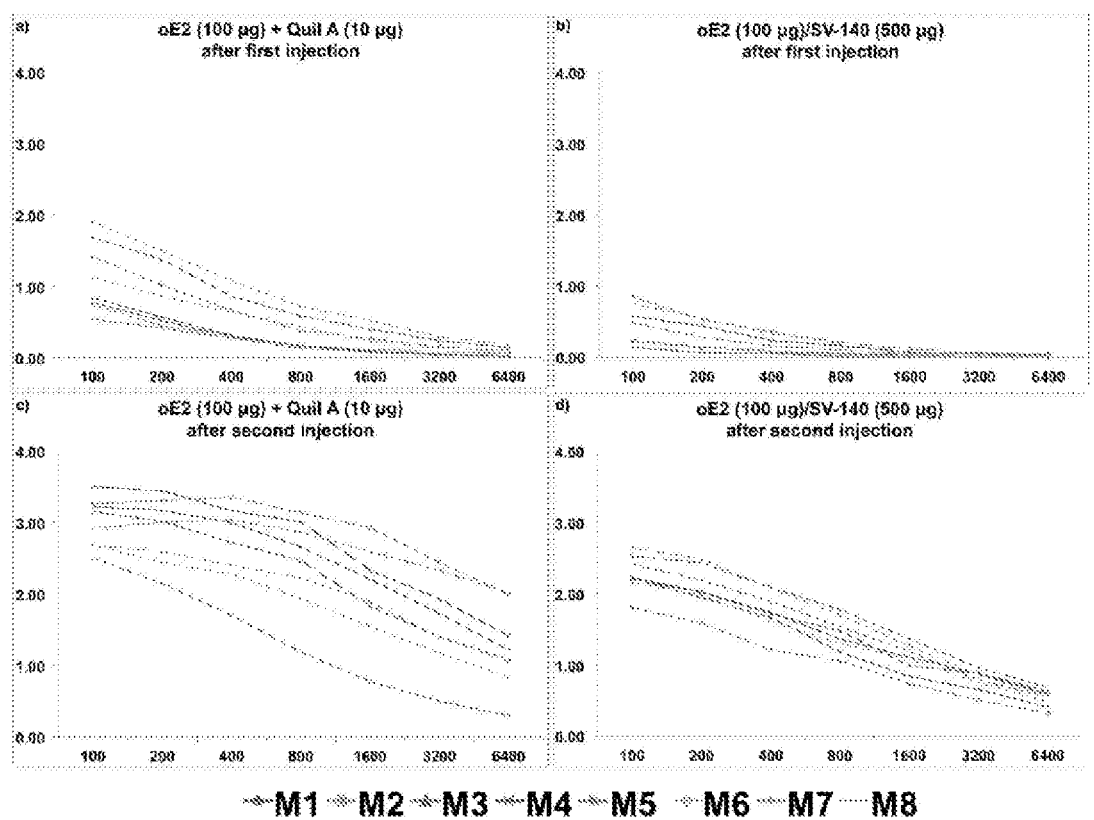
FIG. 23 is a graphical representation showing end point titer data of test sera bleeds for the eight animals after the first and second immunisation. All the mice were administered 100 µL dose at 3 week intervals to the tail base. Sera of individual animals were diluted from 1:100 to 1:6400. The individual graph line in the chart represents individual animals (M1 to M8) in each group.
Figure 25:
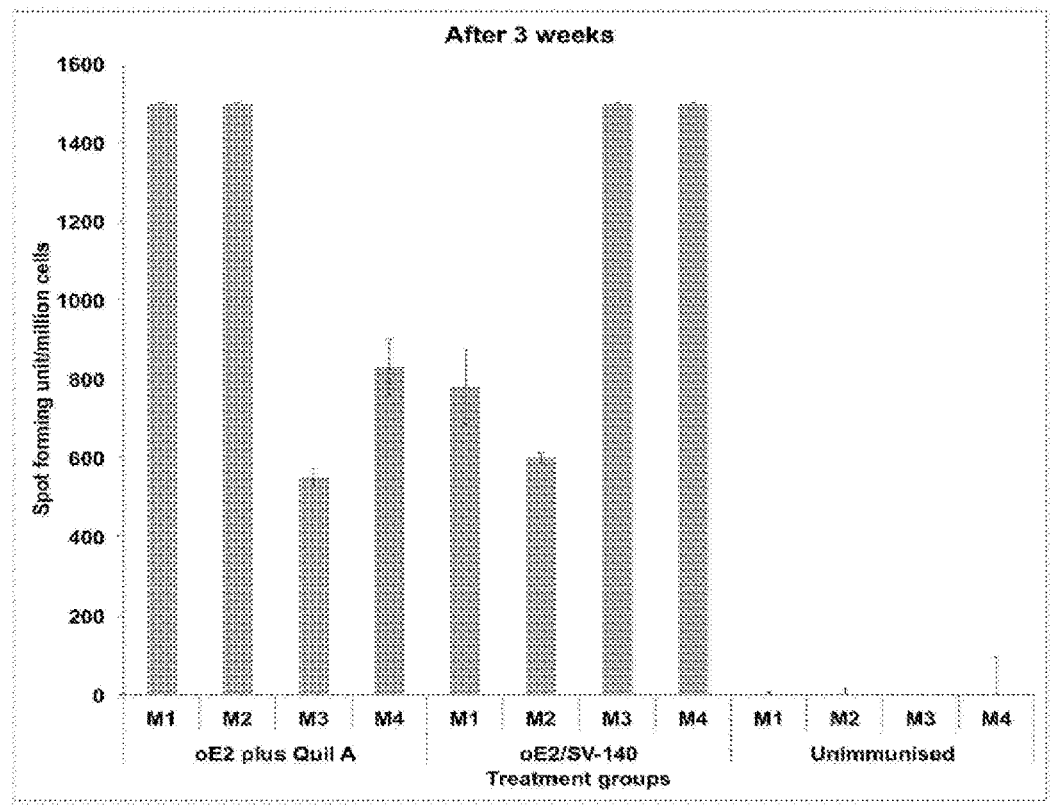
FIG. 25 is a graphical representation showing detection of antigen specific IFN-γ secretion by ELISPOT assay of murine splenocytes from immunised mice. M1 to M4 are the individual mice in each treatment group. The bars in the figure indicate the number of cells producing IFN-γ in response to the oE2 antigen.
Figure 26:
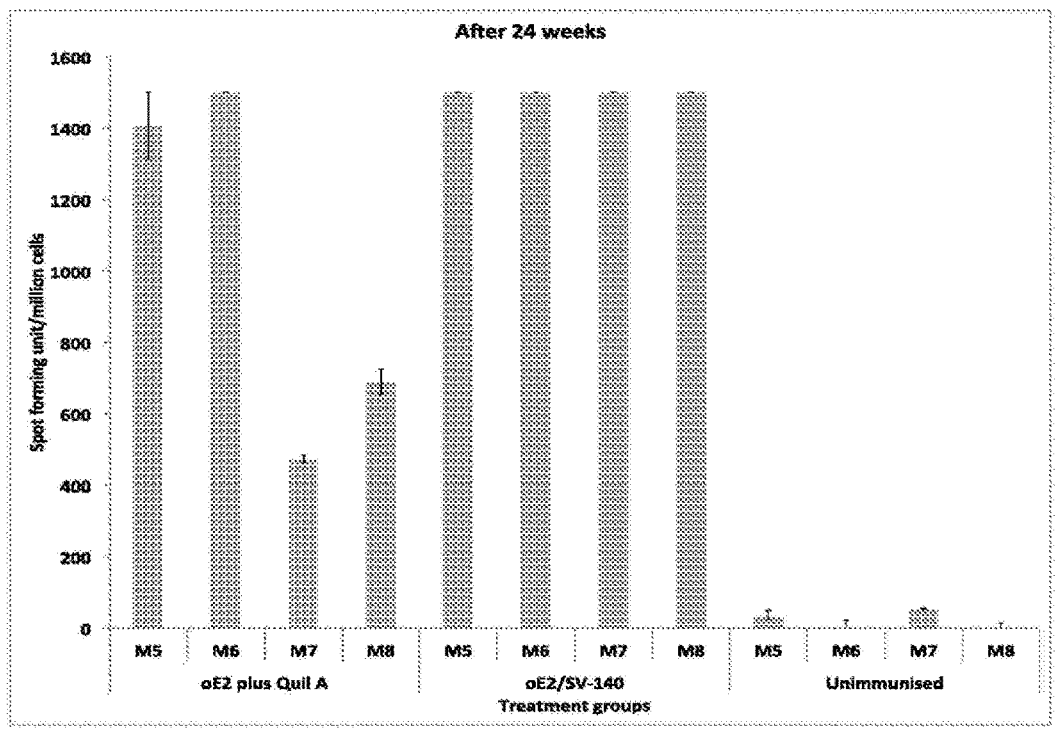
FIG. 26 is a graphical representation showing detection of antigen specific IFN-γ secretion by ELISPOT assay of murine splenocytes from immunised mice. M5 to M8 are the individual mice in each treatment group. The bars in the figure indicate the number of cells producing IFN-γ in response to the oE2 antigen.
Figure 27:
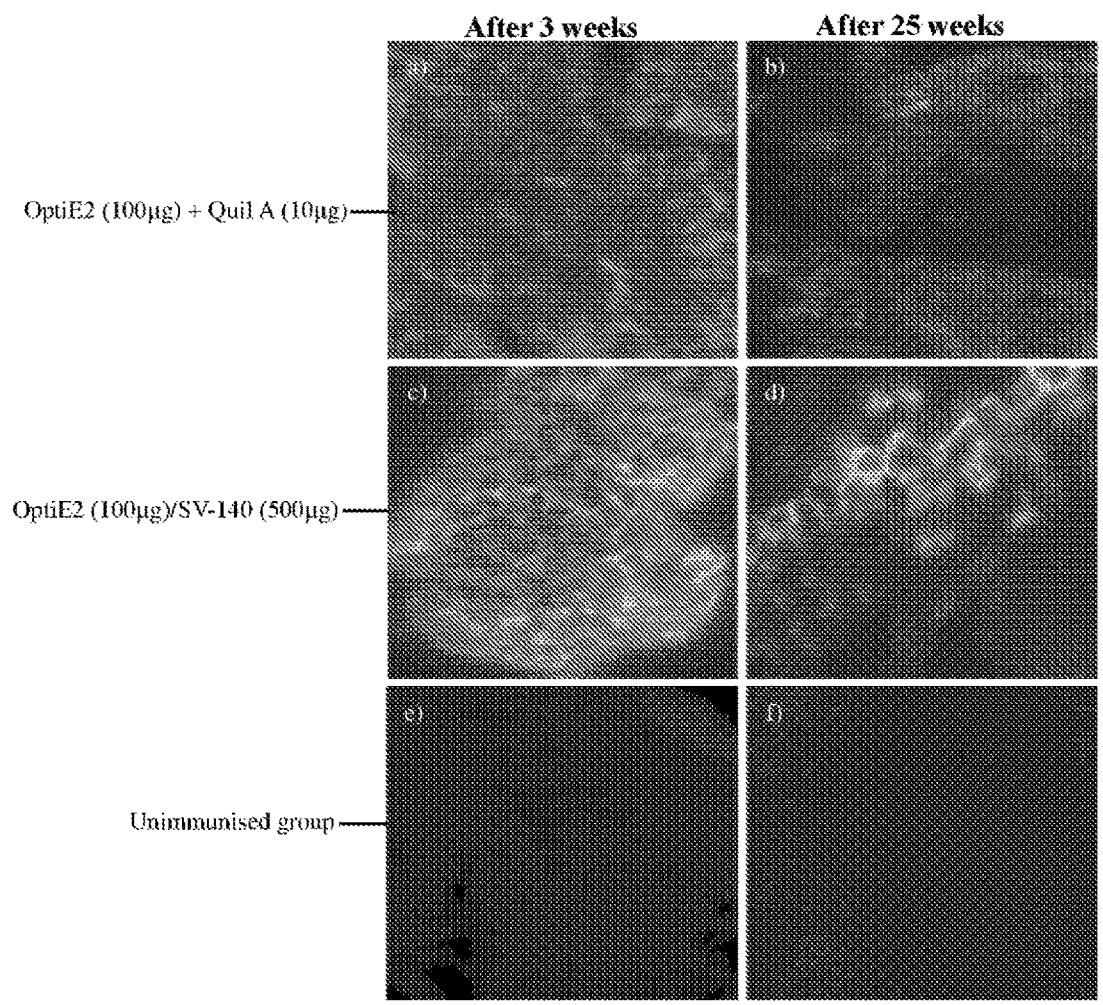
FIG. 27 is a series of images showing immunohistochemistry analyses to determine the induction of total IgG in the spleen sections of the immunised animals; oE2 µlus Quil A positive treatment group a) 3 weeks post the final immunisation, b) 25 weeks post the final immunisation; oE2/SV-140 nanovaccine treatment group c) 3 weeks post the final immunisation, d) 25 weeks post the final immunisation; unimmnised group e) 3 weeks post the final immunisation, f) 25 weeks post the final immunisation.
Figure 28:
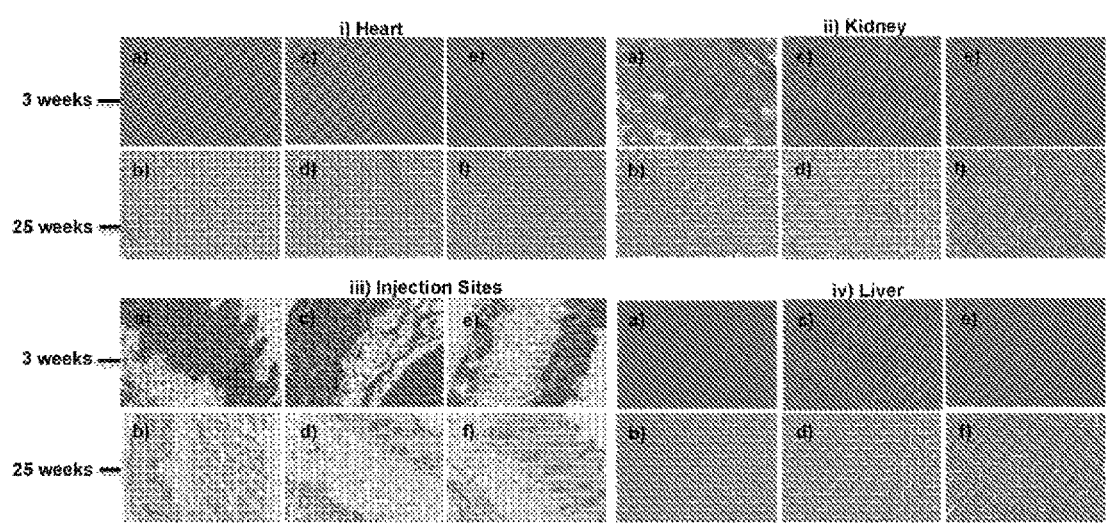
FIG. 28 is a series of images showing the results of a histopathology assay to determine the effects of nanovaccine immunisations; i) Heart, ii) Kidney, iii) Injection sites, iv) Liver samples collected 3 weeks post the final immunisation a) oE2 µlus Quil A, c) oE2/SV-140, e) unimmnised and samples collected 25 weeks post the final immunisation b) oE2 µlus Quil A, d) oE2/SV-140, f) unimmunised.

The mice were immunised with oE2 plus Quil A and oE2/SV-140 vaccine formulations (as set out in table 3) with two subcutaneous vaccine injections and sera samples were collected at three-week intervals after each injection over a 25-week period. The animals in all the treatment groups remained healthy and in the normal weight range throughout the trial period. The total IgG responses of the immunised mice were analysed by anti-oE2-specific ELISA assays. The ELISA result from the terminal bleeds at two time points 3 weeks and 25 weeks (shown in FIGS. 23 and 24), showed that both the nanovaccine treatment group injected with oE2/SV-140 and the positive control group oE2 plus Quil A showed a similar trend in reduction as expected with the antibody response. The negative control group receiving no vaccination showed no antibody response specific to oE2 epitope.

Generation of Cell-Mediated Immune Responses

Figure 29:
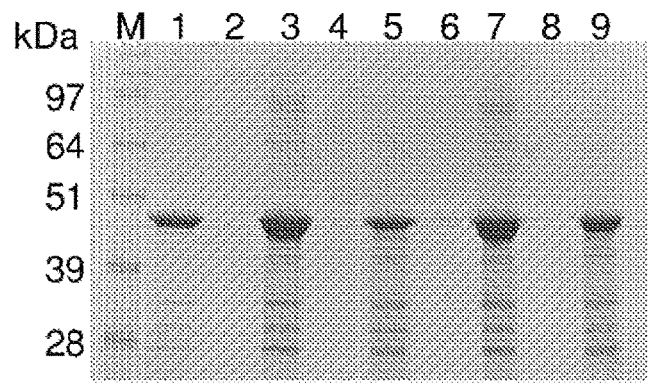
FIG. 29 is a gel image showing VirB9.2 adsorbed onto the 4 types of SV particles. The supernatants after adsorption show little protein remaining, indicating complete adsorption. The particle lanes show protein adsorbed. M SeeBlue 2 marker. 1; VirB9.2 protein. 2; SV100 adsorption supernatant. 3; SV100 particles. 4; SV100NH$_2$ adsorption supernatant. 5; SV100NH$_2$ particles. 6; SV140 adsorption supernatant. 7; SV140 particles. 8; SV140NH$_2$ adsorption supernatant. 9; SV140NH$_2$ particles.
Figure 30:
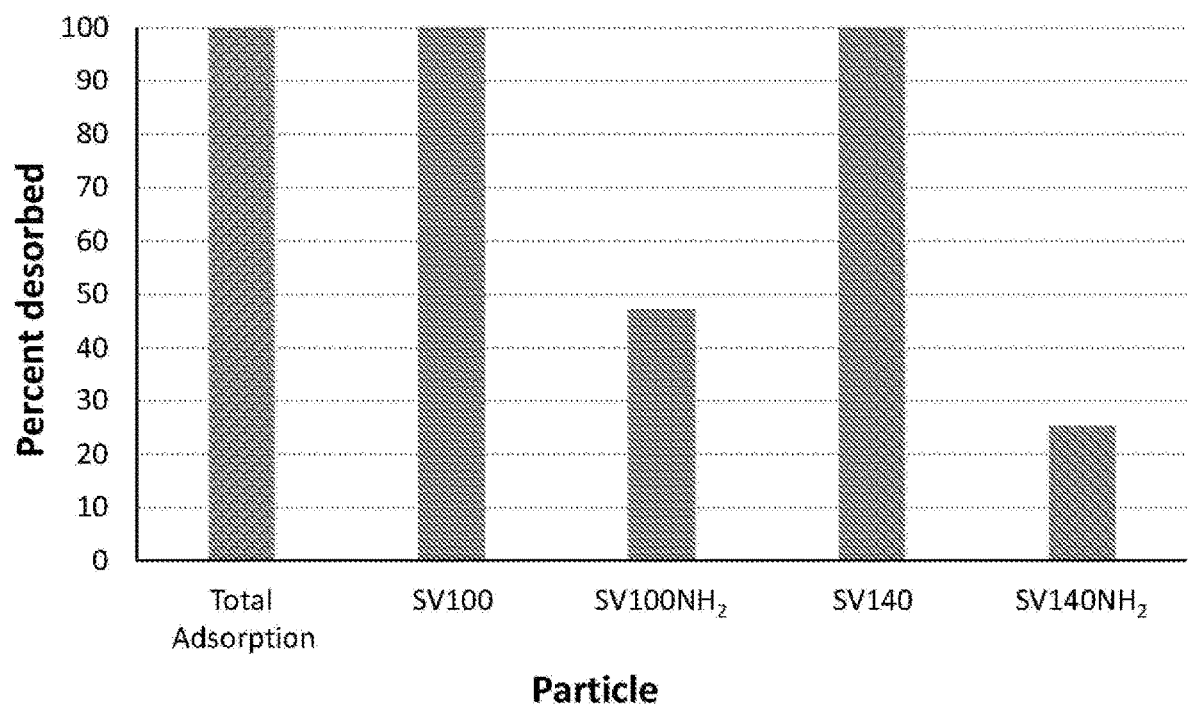
FIG. 30 is a graphical representation showing desorption of VirB9.2 from SV particles in 0.1% SLS, overnight at 37° C. SV100 and SV-140 show the best desorption. SV100 and SV140 show 100% desorption.
Figure 31:
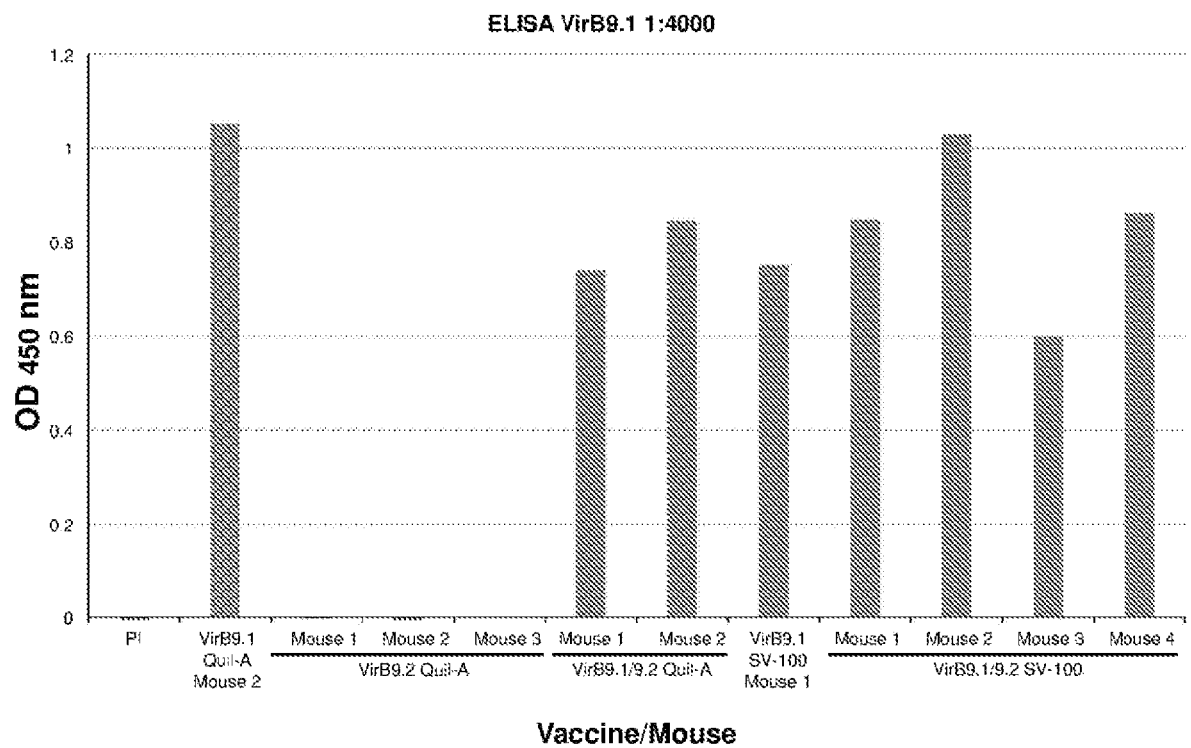
FIG. 31 is a graphical representation showing the humoral immune response against VirB9.1 protein 2 weeks after second immunisation at a dilution of 1:4000. Good response is seen from animals immunised with VirB9.1 with Quil-A as well as SV100. Mixed injection of two proteins with Quil A as well as mixed nanoformulation also gives a similar high antibody response specific to VirB9.1. No cross reaction seen from animals only immunised with VirB9.2 protein.
Figure 32:
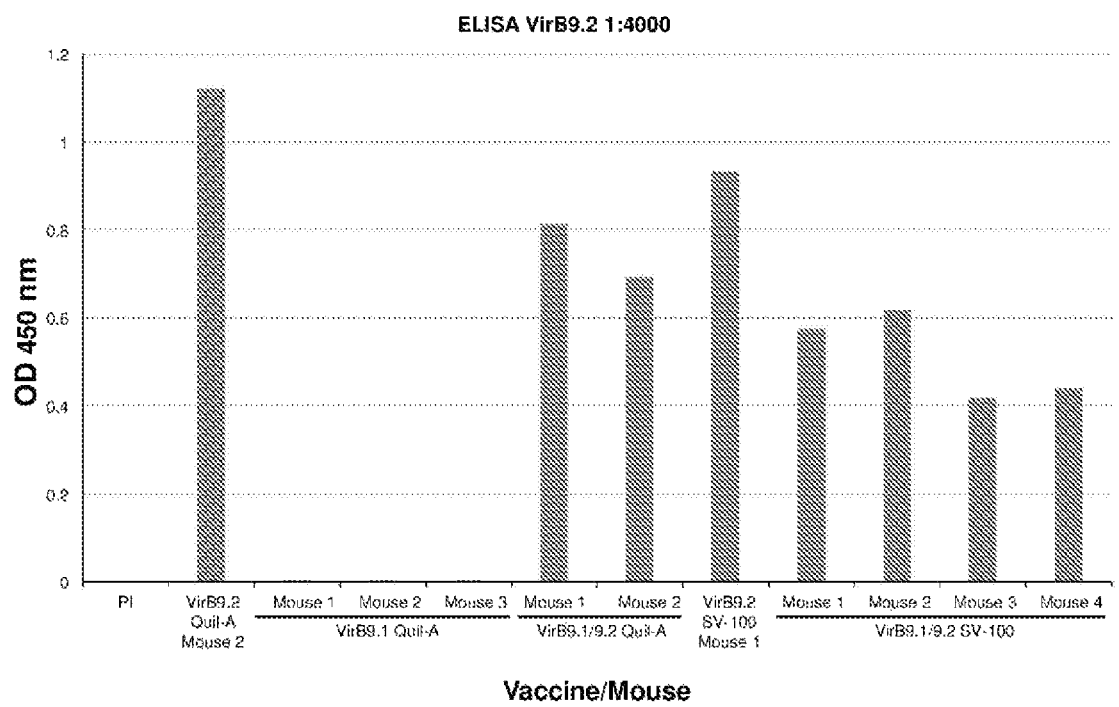
FIG. 32 is a graphical representation showing the humoral immune response against VirB9.2 protein after second immunisation. Good response is seen from animals immunised with VirB9.2 with Quil-A as well as SV100. Mixed injection of two proteins with Quil A as well as mixed nanoformulation also gives a similar high antibody response specific to VirB9.2. No cross reaction seen from animals only immunised with VirB9.1 protein.
Figure 33:
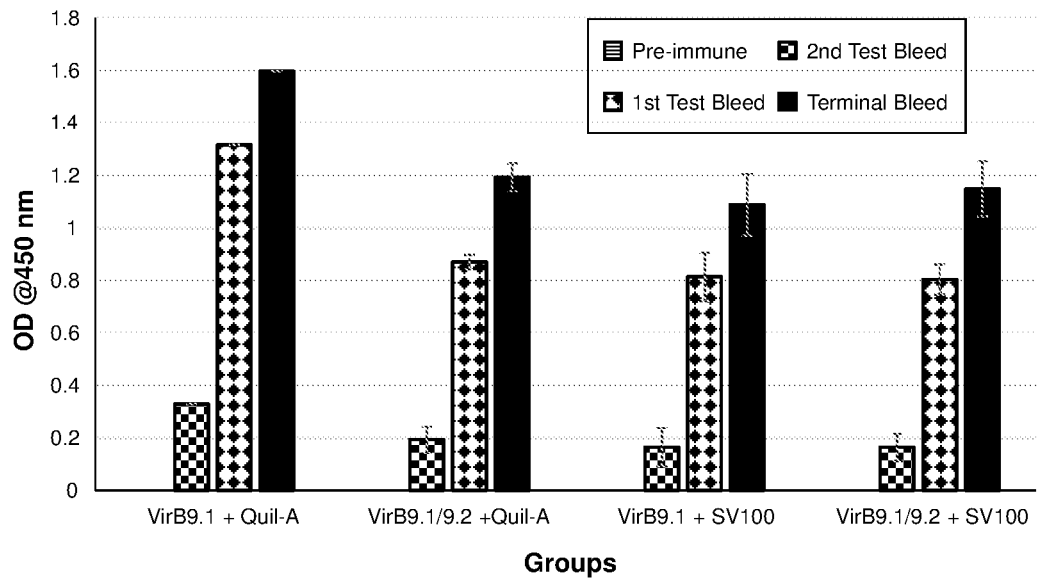
FIG. 33 is a graphical representation showing the humoral response against VirB9.1 protein, 1:4000 dilution. Average response from 5 mice over the course of the experiment, showing relative immune response for the test groups. Pre-immune test bleed was negative and the antibody response shows increasing trend with injections. The trend was observed for both single and mixed nano-formulation.
Figure 34A:
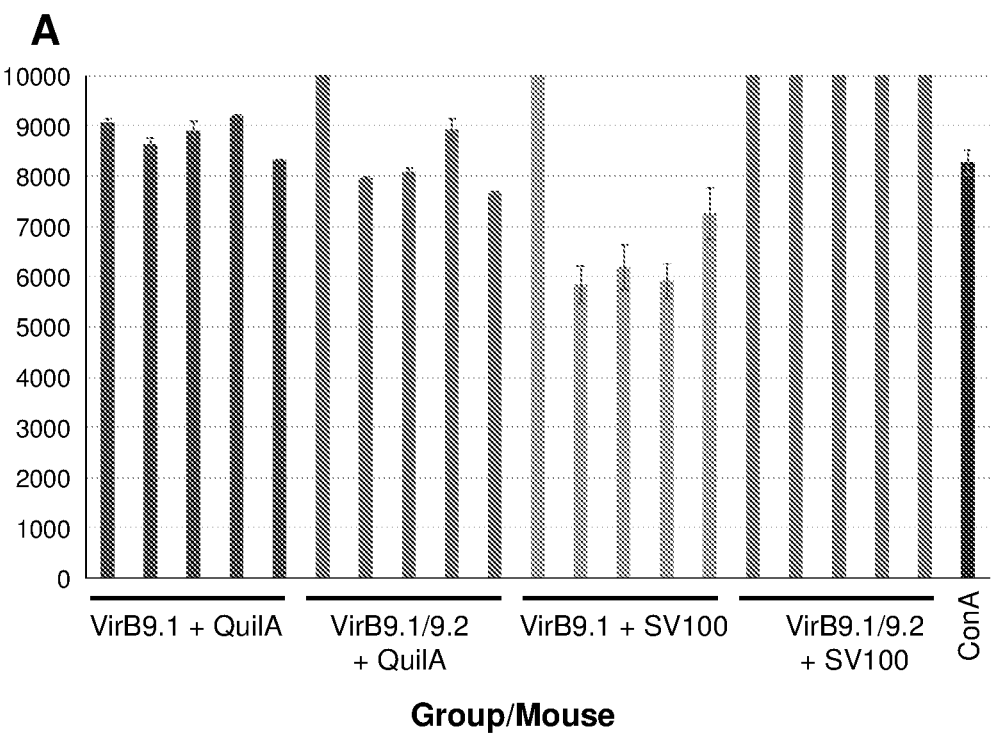
FIG. 34 is a graphical representation showing the cell mediated immune response against VirB9.1 protein. The antigen specific IFN-γ secretion by ELISPOT assay of murine splenocytes from 5 individual mice. (A) Mice injected with VirB9.1+Quil-A show comparable results to VirB9.1+SV100 and also to the multivalent injections VirB9.1/9.2+Quil-A and VirB9.1/9.2+SV100. ConA is the internal control. (B) There was minimal response of animals injected with VirB9.2+QuilA and VirB9.2+SV100 and (C) SV100 alone and unimmunised responses.

ELISPOT assays were used to determine the T-helper type 1 (Th1) cell mediated interferon-γ (IFN-γ) responses to oE2 antigen. Three weeks and twenty-five weeks post the final immunisation spleens from the sacrificed mice from each group were collected and harvested to obtain splenocyte cell populations. The mice receiving nanovaccine formulations oE2/SV-140 showed excellent cell-mediated immune responses to oE2 antigen even after twenty-five weeks post the final immunisation as indicated by the number of cells producing Spot Forming Units (SFU). At 3 weeks, spleen samples were collected from the four sacrificed mice (from the three treatment groups). The 6-week data shows that the cell-mediated response induced by oE2/SV-140 (599-1500 SFU/million cells) was comparable to the oE2 μlus Quil A (551-1500 SFU/million cells) as the two mice in each treatment group showed low response and the other two displayed high response (FIG. 25).

The four mice sacrificed at twenty-five weeks showed that the oE2/SV-140 induced a stronger cell mediated responses (1500 SFU/million cells) in comparison to the positive control group (473-1500 SFU/million cells) (FIG. 26). The ability of SV-140 vesicles to induce both antibody and cell mediated responses after 3 weeks as well as 25 weeks, highlights their potential as excellent self-adjuvants and vaccine delivery vehicles.

Immunohistochemistry Data

Immunohistochemistry studies were conducted on the mice spleen sections. The sections were stained with Alexa Fluor 488 Goat Anti-Mouse IgG and the nucleus with DAPI. The green color in the spleen section represents the presence of antibody response. The oE2/SV-140 (FIG. 27 *c* and *d*) not only produced antibody responses 3 weeks after the final immunisation but also after 25 weeks post the final immunisation. The IgG response appeared stronger at both the time points (3 weeks and 25 weeks) with oE2/SV-140 compared to the positive control oE2 μlus Quil A. The absence of the green color in the sections of the unimmunised treatment group confirms that the mice in the negative control group did not generate antibody responses.

Histopathology Data

Heart, kidney, liver and injection sites from the sacrificed mice were collected and fixed in 10% formalin; they were further processed and stained with hematoxylin and eosin stain. The histopathology results demonstrate that administration of oE2/SV-140 nanovaccine did not have a detrimental effect on the heart, kidney, liver and injection sites at both the time points 3 weeks and 25 weeks post the final immunisation as the sections of mice injected with the oE2/SV-140 looked similar to the negative treatment group (unimmunised) (FIG. 28 i, ii, iii (compare c and d to e and f)). The sections of the animals treated with oE2 μlus Quil A also looked similar to the unimmunised group. This shows that administration of 500 μg of 50 nm SV-140 was very well tolerated in the animals and it did not have any adverse effects on the major organs of the animals.

Conclusion on Nanovaccine Experiments Using BVDV E2

The oE2 adsorbed on the rationally designed SV-140 induced both anti-oE2 IgG as well as IFN-γ responses even after 25 weeks post the final immunisation, demonstrating the potential of SV as both efficient vaccine delivery vehicles and potent adjuvants. The animals were administered with two vaccine doses at three week intervals, the oE2 (100 μg) plus Quil A (10 μg) and the oE2 (100 μg)/SV-140 (500 μg) showed a similar trend of reduction for antibody responses. The oE2/SV-140 produced robust long-term cell-mediated responses in comparison to the positive control oE2 μlus Quil A. The immunohistochemistry results confirmed that the animals treated with oE2/SV-140 produced strong total IgG responses and the histopathology study revealed that injecting a higher dose of nanovaccine (500 μg) did not have a debilitating effect on the major organs of the animals. These results indicate the usefulness of SVs towards the development of a new platform technology for safer and more effective subunit vaccines with an ability to induce long-term humoral as well as cell mediated responses.

Nanovaccine Experiments on Anaplasma

Following on from the experiments relating to adsorbing BVDV-E2 onto silica vesicles (SV), specifically with SV-140, with a high adsorption rate of 200 μg/mg particle, it was decided to use the same approach with 2 different proteins, VirB9.1 (56 KDa) and VirB9.2 (44 kDa), from *Anaplasma* marginale, the causal organism of cattle tick fever. The proteins were expressed in an *Escherichia coli* system. VirB9.1 was expressed using a GST tag in Rosetta (DE3) pLysS cells, induced by 0.2 mM IPTG for 17 hours at 15° C. The resultant soluble protein was purified from bacterial cell lysate by chromatography using a GST affinity column and Superdex 200 10/300 GL size exclusion column, respectively. After purification, VirB9.1 fractions were collected, concentrated and dialysed into PBS for further work. VirB9.2 was expressed using pET-SUMO in BL21 (DE3) cells, induced by 1 mM IPTG for 5 hours at 37° C. The resultant protein was purified from the insoluble inclusion body fraction. After solubilisation, VirB9.2 was dialysed into PBS for further work.

Adsorption of VirB9.1 and VirB9.2 was conducted in 1×PBS buffer at 4° C. and room temperature, respectively. The adsorptions rates onto SV100 particles were 200 μg/mg for VirB9.1 and 400 μg/mg for VirB9.2. The adsorption ratios of VirB9.1 onto SV100-NH$_2$, SV140 andSV140-NH$_2$ were also approximately 200 μg/mg. VirB9.2 shows similar adsorption onto SV100-NH$_2$, SV140 & SV140-NH$_2$(FIG. 29). This data confirms the ability of SV particles to act as carriers of antigenically important proteins other than BVDV E2. Desorption of VirB9.2 from SV100 and SV140 was found to be better as compared to the amino-functionalised particles (FIG. 30). Based on these observations, SV100 loaded with VirB proteins were used in mice trial experiments. Both VirB9.1 and VirB9.2 were adsorbed onto SV100 particles for use in a mice trial to check their ability to induce immune responses. The proteins were adsorbed separately onto the particles and nano-formulations were prepared containing each individual protein and both proteins in combination (Table 4). The time-line for nanovaccine anaplasma mice trial is shown in FIG. 41.

TABLE 4

Mouse trial experimental groups.

| Group | Prototype Vaccine |
|---|---|
| 1 | VirB9.1 (50 μg) + Quil-A (10 μg) |
| 2 | VirB9.2 (50 μg) + Quil-A (10 μg) |
| 3 | VirB9.1 (50 μg) + VirB9.2 (50 μg) + Quil-A (10 μg) |
| 4 | VirB9.1 (50 μg) + SV100 (250 μg) |
| 5 | VirB9.2 (50 μg) + SV100 (125 μg) |
| 6 | VirB9.1 (50 μg + SV100 (250 μg) VirB9.2 (50 μg) + SV100 (125 μg) |
| 7 Control | SV100 alone (375 μg) |
| 8 Control | Unimmunised |

VirB9.1 and VirB9.2 have been shown to be linked proteins and immunisation of linked proteins can increase T-cell-dependent IgG responses (linked recognition), as well as presenting more than one immunogenic protein (Morse et al. 2012). The preliminary data for this experiment shows VirB9.1 and VirB9.2 adsorbed onto SV100 particles successfully induced humoral immunity (FIGS. 31 and 32).

The ELISA results from the Terminal sera (3 weeks after the last injection) for VirB9.1 also show a good antibody response (FIG. 33). The ELISA results for Terminal sera for VirB9.2 follow similar trends as for VirB9.1. Excellent cell mediated immune responses (FIGS. 34 and 35) obtained after three injections also showed that VirB9.1 and ViRB9.2 injected with SV 100 gave consistent responses comparable to Quil-A as the traditional adjuvant.

In the trial, 2 groups of mice were also injected with a combination of both VirB9.1 and VirB9.2 (Table 4). Group 3 (Table 4) uses the traditional adjuvant Quil-A, while Group 6 comprised injecting formulation containing separately adsorbed VirB9.1/9.2 combined after adsorption as a mixed nano-formulation. Animals immunised with the combined VirB9.1 and VirB9.2 nano-formulations showed good humoral (FIGS. 31 to 33) and cell mediated (FIGS. 34 and 35) immune responses comparable to the immune response of mice injected with the individual VirB/SV formulations. More importantly animals vaccinated individually with VirB9.1/SV showed little reactivity with VirB9.2 protein and vice versa in both ELISA (humoral responses, FIGS. 31 to 33) and ELISPOT assay (cell mediated responses, FIGS. 34*b* and 35*b*).

In addition to confirming the ability of SVs to act as an adjuvant and protein carrier in vivo, the immune responses from the combined immunisation showed that the individual proteins are processed independently by the immune system, indicating that SVs can be used to produce multivalent vaccines, which may be able to target multiple diseases in a single dose.

Adsorption Capacity of Model Therapeutical Proteins by Silica Vesicles and Protein Stability Tests Correlation of Protein Loading Amount and Entrance Size of Silica Vesicles The inventors have found the entrance size of the present silica vesicles (SVs) can be adjusted from <3.9 to 34 nm (diamond in FIG. 36) while the wall thickness is maintained at ~6 nm (circle in FIG. 36). After hydrophobic modification with $-C_{18}$ chains, the entrance size of SVs decreases 1-2 nm in all cases (square in FIG. 36). The relationship between loading amount of therapeutical proteins and entrance size of SVs has been investigated using both these series of SV. Cytochrome c (the upside down triangle in FIG. 36) and Ribonuclease A (RNase A indicated by the triangle) have been used as model therapeutical proteins and results have been discussed previously.

As shown in FIG. 36, both series of SV show a similar trend of adsorption capacity towards two model proteins as entrance size increases: when the entrance size of SV is equal to the wall thickness, the loading capacity reaches a maximum (563 mg/g for RNase A on hydrophobic modified SV and 840 mg/g for Cyto C on unmodified SV).

To further predict the positions of RNase A adsorbed on functionalized SV samples, the RNase A adsorption capacity per unit surface area (mg/$m^2$) was calculated (Table 5), dividing the adsorption capacity by BET surface area excluding the unusable micropore area for protein adsorption. Solid Stöber spheres with the same hydrophobic modification and ~50 nm particles size have also been used for RNase A adsorption in comparison with SV, which showed 89 mg/g loading amount of RNase A after 18 h. For modified Stöber spheres, it is clear that the adsorption of RNase A occurs on the external surface with a single layer adsorption behavior. Compared to 50 nm solid Stöber spheres, SV-10-50-Cis has a same size but weaker adsorption capacity of 0.64 mg/$m^2$, half of that of Stöber spheres (1.13 mg/$m^2$). Like in the case of solid Stöber spheres, RNase A can only be adsorbed on the outer surface of SV-10-50-$C_{18}$ because its entrance size is smaller than the protein size. However, its BET surface area excluding the micropore area consists of both the internal and external surface area of hollow SV-10-50-$C_{18}$ measured by nitrogen sorption, which is double of that of solid Stöber spheres, causing a lower adsorption capacity. SV-10-100-$C_{18}$ shows a capacity of 1.51 mg/$m^2$, which is slightly higher than that in solid Stöber spheres. The entrance size of SV-10-100-$O_{18}$ is <3.9 nm after hydrophobic modification. Although the exact entrance size cannot be determined from the nitrogen adsorption technique, it can be deduced that the entrance size is close to 3.9 nm considering that SV-10-100 has an entrance size of 6 nm and the entrance size decrease after modification is in the range of 1-2 nm. This entrance size is close to the protein size, thus RNase A can be loaded into the cavity, leading to a relatively high adsorption capacity. SV-10-120-$C_{18}$ and SV-10-140-$C_{18}$ with entrance sizes much larger than the size of RNase A show an adsorption capacity per unit area twice of that in Stöber spheres, indicating that RNase A is adsorbed not only on the surface of silica shell, but also inside the cavity through multi-layer adsorption.

TABLE 5

Calculated Ribonuclease A adsorption capacity of silica nanoparticles.

|  | Stöber sphere 50 nm | SV-10-50-$C_{18}$ | SV-10-50-100-$C_{18}$ | SV-10-50-120-$C_{18}$ | SV-10-50-140-$C_{18}$ |
|---|---|---|---|---|---|
| $S_{BET}$ (m$^2$ g$^{-1}$) | 90 | 536 | 265 | 227 | 152 |
| $S_{Micro}$ (m$^2$ g$^{-1}$) | 11 | 213 | 13 | 0 | 40 |
| $S_{BET-Micro}$ (m$^2$ g$^{-1}$) | 79 | 323 | 252 | 227 | 112 |
| $C_{RNase\ A}$ (mg g$^{-1}$) | 89 ± 1 | 206 ± 6 | 381 ± 2 | 563 ± 1 | 276 ± 8 |
| $C'_{RNase\ A}$ (mg m$^{-2}$) | 1.13 | 0.64 | 1.51 | 2.48 | 2.46 |

$S_{BET}$: BET surface area; $S_{Micro}$: t-Plot micropore area; $S_{BET-Micro}$: BET surface area − t-Plot micropore area; $C_{RNase\ A}$: RNase A adsorption capacity; $C'_{RNase\ A}$: RNase A adsorption capacity per m$^2$ ($C_{RNase\ A}/S_{BET-Micro}$).

Thermal Stability of RNase A Loaded in Hydrophobic Modified SV

Figure 37:
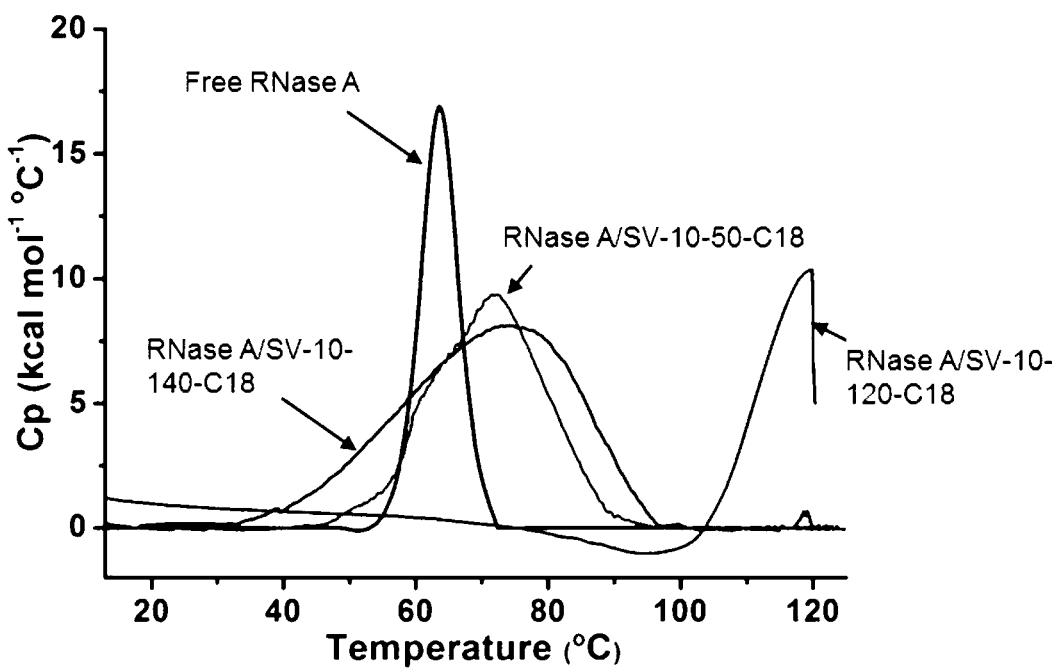
FIG. 37 is a graphical representation showing differential scanning calorimetry curves of free RNase A and RNase A loaded in hydrophobic modified silica vesicles dissolved or dispersed in 10 mM PBS solution (RNase A 0.5 mg/ml), the heating rate is 60° C./h.

The thermal unfolding of RNase A was measured by differential scanning calorimetry (DSC) in the range of 10–130° C. The DSC was carried out using a VP DSC microcalorimeter (MicroCal Company, USA) with a heating rate of 60° C./h. In a typical procedure, the RNase A/SV was suspended in 10 mM PBS solution with the RNase A concentration of 0.5 mg/ml. A reference suspension was also prepared using only SV the same concentration. The reference and sample suspension were injected in the corresponding cells for DSC measurements. The DSC curve of free RNase A was also obtained. FIG. 37 shows a series of DSC curves with the temperature of RNase A/SV suspension as the x axis and the apparent molar heat capacity (Cp) as the γ axis which is baseline-substrated and normalized by the concentration of RNase A. The DSC curve of free RNase A shows an endothermic peak which indicates thermal unfolding of RNase A. The midpoint temperature for the RNase A thermal unfolding ($T_m$) was also measured to be centred at 63.6° C., in accordance with literature reports. The $T_m$ of RNase A loaded in SV-10-120-$C_{18}$ increases to ~119° C., much higher than that of RNase A/SV-10-50-$C_{18}$ (71.9° C.) and RNase A/SV-10-140-$C_{18}$ (74.9, 118° C.). The DSC results show that RNase A loaded in the hydrophobic modified SV with the entrance size of ~6 nm shows the highest thermal stability in PBS compared to SV-10-50-$C_{18}$ that adsorbs RNase A on the outer surface and RNase A/SV-10-140-$C_{18}$ that possesses large entrance size.

Figure 38:
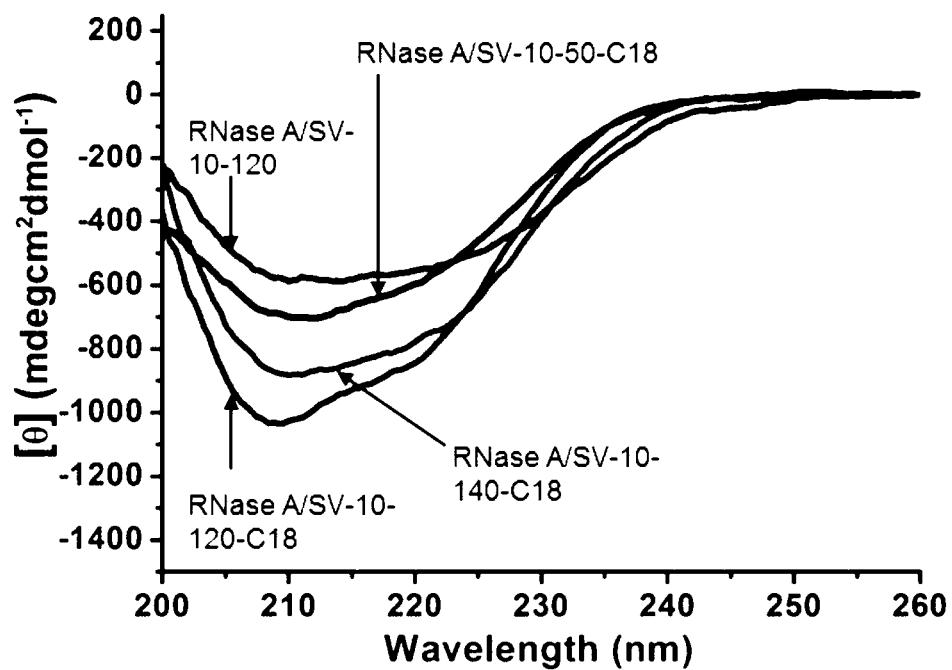
FIG. 38 is a graphical representation showing circular dichroism spectra of RNase A/silica vesicles treated with 0.01 M HCl (pH 2) at 65° C. for 40 min and neutralized to pH 7 with 0.01 M NaOH. Final RNase A concentration is mg/ml.

Activity of RNase A Loaded in Hydrophobic Modified SV after Acid and Heat Treatment The stability and activity of RNase A loaded in hydrophobic modified SV was further investigated with acid and heat treatment. In a treatment procedure, 50 μl 0.01 M HCl (pH 2) was added to ~1 mg RNase A loaded in SV. The mixture was kept in 65° C. for 40 min, then neutralized with 0.01 M NaOH solution (pH 12) until the pH reached 7. The final RNase A concentration was then diluted to 0.5 mg/ml. Free RNase A was also treated accordingly as a control group. In order to investigate the secondary structure change of RNase A after the treatments, circular dichroism (CD) spectra of RNase A/SV suspension was measure with SV suspensions as the reference. FIG. 38 shows that the intensity in CD spectra in the wavelength range of 200-230 nm is RNase A/SV-10-120-$C_{18}$>RNase A/SV-10-140-$C_{18}$>RNase A/SV-10-50-$C_{18}$>RNase A/SV-10-120. The higher intensity indicates more secondary structure is maintained after the treatment. Thus, RNase A loaded in SV-10-120-$C_{18}$ show the highest content of secondary structure after the acid and heat treatment.

Figure 39:
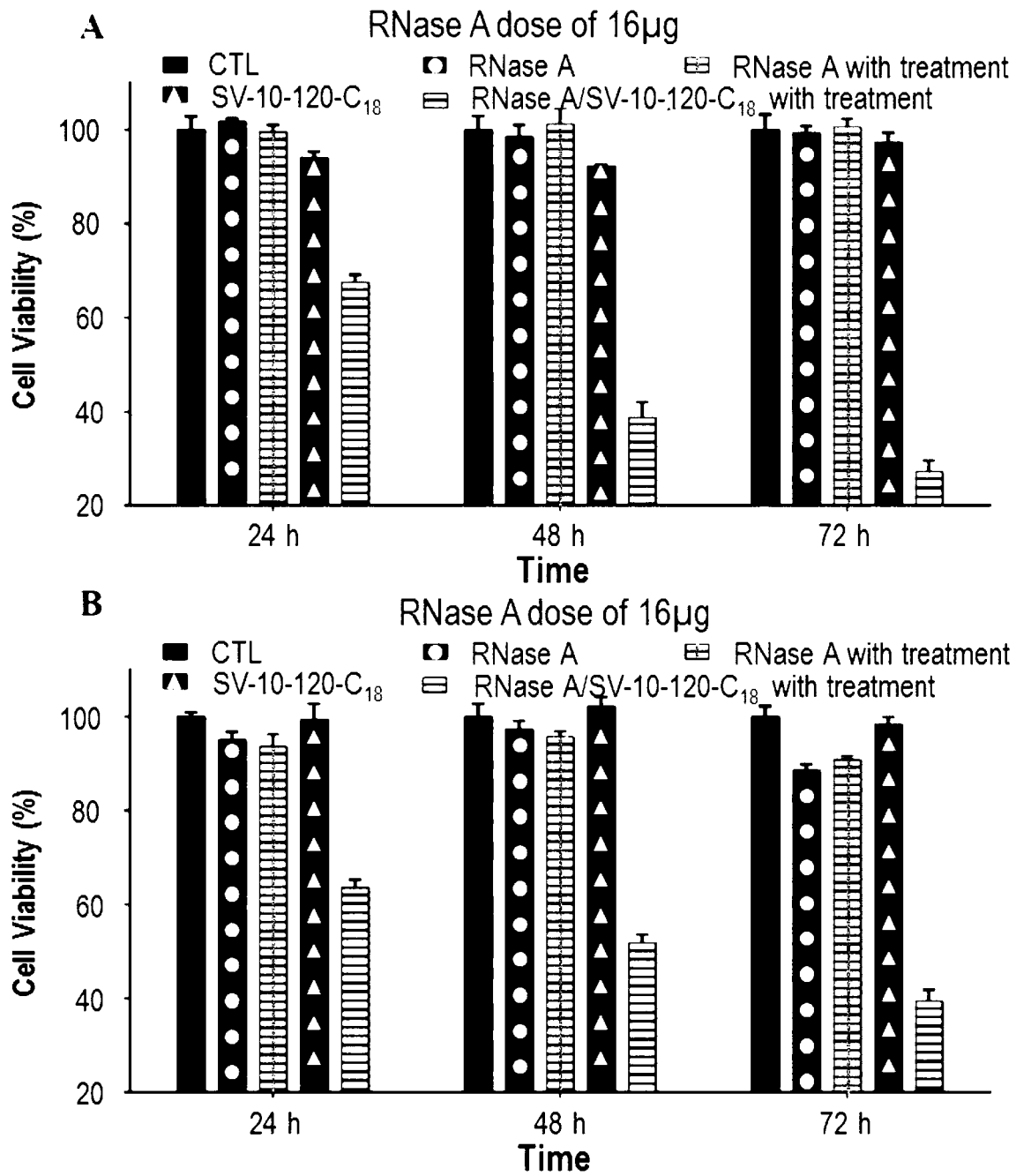
FIG. 39 is a graphical representation showing cell viability of (A) SCC25 and (B) HCT116 cells treated with RNase A at a dosage of 6 μg/ml after 24, 48 and 72 h. The free RNase A and RNase A loaded in silica vesicles were treated with 0.01 M HCl (pH 2) at 65° C. for 40 min and neutralized to pH 7 with 0.01 M NaOH before adding to the cells.

The RNase A/SV-10-120-$C_{18}$ after acid and heat treatment was then used for cellular delivery to further test the activity of RNase A. The procedure described previously was employed. As displayed in FIG. 39, SV-10-120-$C_{18}$ shows minimised cellular toxicity to both SCC25 and HCT116 cells even after 72 h, indicating the excellent biocompatibility of the functionalized SV samples. When SCC25 and HCT116 cells are treated with free RNase A, no inhibition can be seen, because the naked protein cannot enter into cells. RNase A delivered by SV-10-120-$C_{18}$ exhibits time-dependent cell toxicity, where the cell inhibition ability increases with the exposure time increasing from at the RNase A concentration of 16 μg/ml (FIG. 39A). The same trend can be observed in HCT116 cells with the cell inhibition of 33% at 24 h to 48% at 48 h and finally 69% at 72 h. The cell inhibition ability of RNase A/SV-10-120-$C_{18}$ confirms the stability and retained activity of RNase A after acid and heat treatment.

Figure 40:
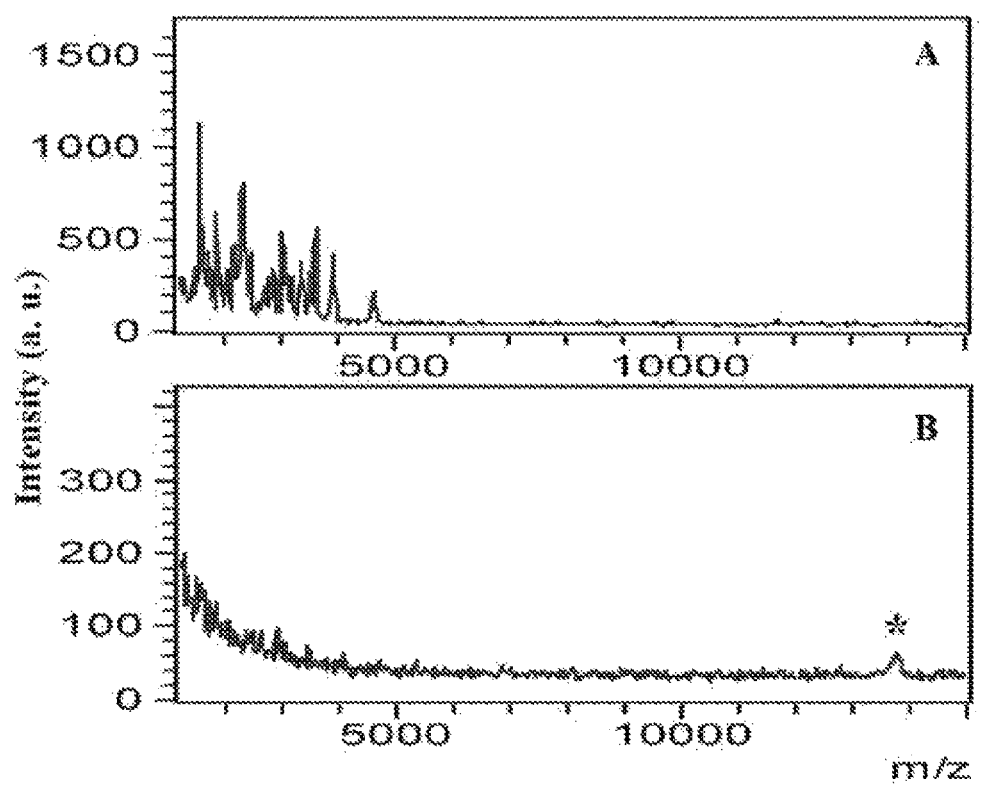
FIG. 40 is a graphical representation showing mass spectrometry of RNase A loaded in (A) SV-10-120 without modification and (B) SV-10-120-$C_{18}$ with hydrophobic modification after the treatment of trypsin digestion.
Figure 41:
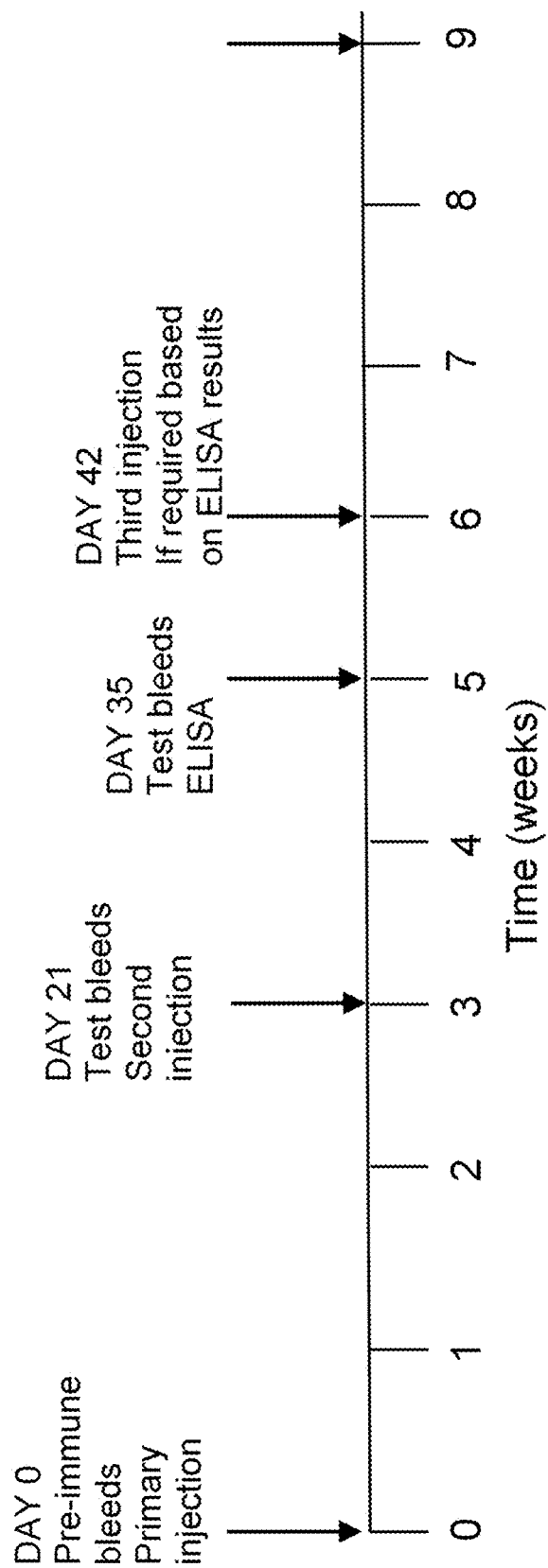
FIG. 41 shows the time-line for the nanovaccine anaplasma mice trial.

Most therapeutical proteins possess fragile structures that easily undergo denaturation or digestion by proteases. For example, proteins need to survive pepsin or trypsin digestion during oral delivery and plasmin in intravenous injections. In the present experiments, the RNase A/SV-10-120-$C_{18}$ was digested with trypsin and the amount of intact RNase remaining was quantitatively detected by mass spectromatry (MS). Firstly 1 mg of RNase A loaded in SV was treated with dithiothreitol at 60° C. for 30 mins. This process is to break the disulfide bonds in free RNase A. Secondly, the RNase A/SV was added to 1 mg/ml trypsin in PBS solutions (1:50) at 37° C. with shaking for ~12 h. The mixture was then centrifugated, and the supernatant was removed from the precipitate. The precipitate was spotted onto a MALDI MPT 384 μlate and mixed with 1 μl CHCA solution before the test. The samples were analyzed on a Bruker Autoflex TOF/TOF III Smart beam. The mass spectra were obtained in the LP-PepMix mode via an accumulation of 200 laser shots at 10 different sites under a laser intensity of 39% for data collection and calibrated. Three standard peptides, Angiotensin II (Mw=1046.5 Da), ACTH-Clip (Mw=2465.2 Da) and Somatostatin 28 (Mw 3147.5 Da) were used for calibration purposes to reduce variability. FIG. 40A shows the MS of RNase A/SV-10-120 which shows a series of peaks ranging from 1000-5000 in the mass-to-charge ratios. These peaks can all be attributed to the peptides digested from intact RNase A by trypsin. In comparison, the MS of RNase A/SV-10-120-01$_8$ shows a small peak at the mass-to-charge ratio of 13.7k which is the mass of intact RNase A. As a result, an amount of RNase A remains after the trypsin digestion process when adsorbed by hydrophobic modified SV, while without the modification RNase A loaded is completely digested.

The results presented herein show that SVs with the entrance size close to the protein size show the highest loading amount of the model therapeutical proteins. Using RNase A as an example, it is predicted that the location of RNase A loaded in SV-10-120-$C_{18}$ is not only on the outer surface but also in the SV cavity. Furthermore, these experiments suggest that SV-10-120-$C_{18}$ with an entrance size of ~6 nm and hydrophobic modifications shows protection toward RNase A from harsh conditions of heat or potential acid or tryspin digestion. The RNase A loaded in SV-10-120-$C_{18}$ still shows successful inhibition to cancer cells even after treatment with heating and strong acid. This finding is surprising and provides an important understanding not previously found in the art which will be crucial for designing effective protective nano-carriers for therapeutical protein delivery.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

The invention claimed is:

1. A method of producing silica vesicles comprising a porous silica based wall surrounding an internal cavity, wherein the silica based wall comprises spherical perforations, the method comprising step (a) followed by step (b) and/or step (c); then by step (d):
   (a) producing a silica formulation by adding a hydrolysable silica source to an aqueous acidic buffer solution having a pH of between 3 and 6 comprising a block copolymer surfactant, the silica formulation being maintained at a temperature of between 5° C. to 15° C., and continuously stirring the formulation for a first predetermined period of time until silica-block copolymer surfactant composite vesicles form; wherein the hydrolysable silica source is of the general formula $[(X_1)(X_2)Si(X_3)(X_4)]$, wherein each of $X_1$, $X_2$, $X_3$ and $X_4$ is independently selected from the group consisting of an optionally substituted $C_2$-$C_8$ alkoxy, an optionally substituted aryloxy, an optionally substituted $C_2$-$C_8$ alkyl, an optionally substituted aryl, and an optionally substituted $C_2$-$C_8$ alkenyl;
   (b) raising the temperature of the silica formulation containing the silica-block copolymer surfactant composite vesicles to be between 25° C. to 100° C. and agitating the mixture to form silica-block copolymer surfactant composite vesicles having spherical structures within the vesicle walls;
   (c) exposing the vesicles to a hydrothermal treatment; and
   (d) calcining the vesicles, to thereby produce the silica vesicles.

2. The method of claim 1 wherein the hydrolysable silica source is of the general formula $[(X_1)(X_2)Si(X_3)(X_4)]$, wherein each of $X_1$, $X_2$, $X_3$ and $X_4$ is independently an optionally substituted $C_2$-$C_8$ alkoxy.

3. The method of claim 1 wherein the block copolymer surfactant is an olefinic triblock copolymer.

4. The method of claim 1 wherein the block copolymer surfactant is a poly(ethylene oxide)-poly(alkylene oxide)-poly(ethylene oxide) block copolymer.

5. The method of claim 1 wherein in step (b), the temperature is raised to be between 30° C. to 85° C.

6. The method of claim 1 wherein step (a) is followed by step (b) which is followed by step (c) and then step (d).

7. The method of claim 1 wherein the hydrothermal treatment is carried out at a temperature which is between 90° C. to 200° C.

8. The method of claim 1 wherein the hydrothermal treatment is carried out at a pressure of greater than 0.7 bar and less than 10 bar.

9. The method of claim 1 in which the surface of the silica vesicles is hydrophobically modified following calcination.

* * * * *